US006045774A

United States Patent [19]
Hiatt et al.

[11] Patent Number: 6,045,774
[45] Date of Patent: Apr. 4, 2000

[54] J CHAIN POLYPEPTIDE TARGETING MOLECULE LINKED TO AN IMAGING AGENT

[75] Inventors: Andrew C. Hiatt, San Diego; Mich B. Hein, Fallbrook; John H. Fitchen, La Jolla, all of Calif.

[73] Assignee: EPIcyte Pharmaceutical Inc., San Diego, Calif.

[21] Appl. No.: 08/782,480

[22] Filed: Jan. 10, 1997

[51] Int. Cl.$^7$ .......................... A61K 49/00; A61K 38/43; C12N 11/02; C07K 1/00
[52] U.S. Cl. ...................... 424/9.1; 424/9.34; 424/9.341; 424/94.1; 435/4; 435/174; 435/177; 530/402; 530/810
[58] Field of Search ................................ 435/4, 174, 177; 424/1.11, 1.49, 1.53, 1.69, 9.1, 9.34, 9.341, 9.351, 94.1; 530/402, 810

[56] References Cited

U.S. PATENT DOCUMENTS

| | | | |
|---|---|---|---|
| 4,837,167 | 6/1989 | Schoemaker et al. | 436/513 |
| 5,169,933 | 12/1992 | Anderson et al. | 530/391.3 |
| 5,240,833 | 8/1993 | Nudelman et al. | 435/70.21 |
| 5,484,707 | 1/1996 | Goldblum et al. | 435/7.92 |
| 5,512,443 | 4/1996 | Schlom et al. | 435/7.23 |
| 5,731,168 | 3/1998 | Carter et al. | 435/69.1 |

FOREIGN PATENT DOCUMENTS

| | | |
|---|---|---|
| 58134032 | 8/1983 | Japan . |
| WO 98/30592 | 7/1998 | WIPO . |

OTHER PUBLICATIONS

Tamer et al., "Comparative Studies of Transcytosis and Assembly of Secretory IgA in Madin–Darby Canine Kidney Cells Expressing Human Polymeric Ig Receptor", *The Journal of Immunology* 155:707–714, 1995.

Henneberg et al., "Antibrain Antibodies in Alcoholic Patients," *Alcohol & Alcoholism* 28(2): 181–187, 1993.

Hammond, "Ultrastructural Characteristics of Surface IgM Reactive Malignant Lymphoid Cells," *Experimental Research* 59: 359–370, 1970.

Valnes and Brandtzaeg, "Comparison of Paired Immunofluorescence and Paired Immunoenzyme Staining Methods Based on Primary Antisera from the Same Species," *The Journal of Histochemistry and Cytochemistry* 30(6): 518–524, 1982.

Brown and Koshland, "Evidence for a long–range conformational change induced by antigen binding to IgM antibody," *Proc. Natl. Acad. Sci. USA* 74(12): 5682–5686, 1977.

Brandtzaeg and Baklien, "Immunohistochemical studies of the immunoglobulin–producing cell systems of the human intestinal mucosa," *Acta histochemica, Suppl.* 21: 105–119, 1980.

Ferkol et al., "Gene Transfer into Respiratory Epithelial Cells by Targeting the Polymeric Immunoglobulin Receptor," *J. Clin. Invest.* 92: 2394–2400, 1993.

Terskikh et al., "Dimeric Recombinant IgA Directed Against Carcino–Embryonic Antigen, A Novel Tool For Carcinoma Localization," *Molecular Immunology* 31(17): 1313–1319, 1994.

Hendrickson et al., "Altered Hepatic Transport of Immunoglobulin A in Mice Lacking the J Chain," *J. Exp. Med.* 182: 1905–1911, 1995.

Max and Korsmeyer, "Human J Chain Gene. Structure and Expression in B Lymphoid Cells," *Journal of Experimental Medicine* 161: 832–849, 1985.

Frutiger et al., "Disulfide Bond Assignment in Human J Chain and Its Covalent Pairing with Immunoglobulin M," *Biochemistry* 31: 12643–12647, 1992.

Kulseth and Rogne, "Cloning and Characterization of the Bovine Immunoglobulin J Chain cDNA and Its Promoter Region," *DNA and Cell Biology* 13(1):37–42, 1994.

Rifai and Mannik, "Clearance Kinetics and Fate of Mouse IgA Immune Complexes Prepared with Monomeric or Dimeric IgA," *Journal of Immunology* 130(4): 1826–1832, 1983.

Burns et al., "Protective Effect of Rotavirus VP6–Specific IgA Monoclonal Antibodies That Lack Neutralizing Activity," *Science* 272: 104–107, 1996.

Mazanec et al., "Intracellular Neutralization of Influenza Virus by Immunoglobulin A Anti–Hemagglutinin Monoclonal Antibodies," *Journal of Virology* 69(2): 1339–1343, 1995.

Kaetzel et al., "The polymeric immunoglobulin receptor (secretory component) mediates transport of immune complexes across epithelial cells: A local defense function for IgA," *Proc. Natl. Acad. Sci.* 88:8796–8800, 1991.

Kaetzel et al., "Epithelial Transcytosis of Monomeric IgA and IgG Cross–linked Through Antigen to Polymeric IgA. A Role for Monomeric Antibodies in the Mucosal Immune System," *Journal of Immunology* 152: 72–76, 1994.

Sheldrake et al., "Selective Transport of Serum–Derived IgA Into Mucosal Secretions," *Journal of Immunology* 132(1): 363–368, 1984.

(List continued on next page.)

*Primary Examiner*—David M. Naff
*Attorney, Agent, or Firm*—Seed IP Law Group PLLC

[57] ABSTRACT

Targeting molecules for use in delivering imaging agents to epithelial tissue are disclosed. Upon delivery, the imaging agent(s) may remain within an epithelial cell or may undergo transepithelial transport via transcytosis. The targeting molecules may be used, for example, for diagnostic techniques. The targeting molecule is a polypeptide, which may be produced by recombinant methods, that forms a closed covalent loop, contains at least three peptide domains having β-sheet character which are separated by domains lacking β-sheet character, specifically binds to a basolateral factor attached to a basolateral domain of an epithelial surface causing uptake of a linked imaging agent into cells of the epithelial surface, and is not a full length dimeric Iga. Preferably, the polypeptide is a J chain polypeptide, or a J chain polypeptide linked to an immunoglobulin heavy chain without an immunoglobulin light chain.

37 Claims, 1 Drawing Sheet

OTHER PUBLICATIONS

Mestecky et al., "The Role of the Liver in Catabolism of Mouse and Human IgA," *Immunological Investigations* 18(1–4): 313–324, 1989.

Youngman et al., "Inhibition of IFN–γ Activity in Supernatants from Stimulated Human Intestinal Mononuclear Cells Prevents Up–Regulation of the Polymeric Ig Receptor in an Intestinal Epithelial Cell Line," *Journal of Immunology 153*: 675–681, 1994.

Rifai et al., "Clearance Kinetics and Fate of Macromolecular IgA in Patients with IgA Nephopathy," *Laboratory Investigation 61*(4): 381–388, 1989.

Emancipator and Lamm, "IgA Nephropathy: Overproduction of Decreased Clearance of Immune Complexes?" *Laboratory Investigation 61*(4): 365–367, 1989.

Nagura et al., "Translocation of Dimeric IgA Through Neoplastic Colon Cells In Vitro," *Journal of Immunology 123*(5): 2359–2368, 1979.

Mannik and Arend, "Fate of Preformed Immune Complexes in Rabbits and Rhesus Monkeys," *Journal of Experimental Medicine 134*(3 pt. 2): 19s–31s, 1971.

SEQUENCE COMPARISON OF J CHAIN PROTEINS AND DEDUCED J CHAIN SEQUENCES
FROM SIX ORGANISMS

```
              10         20         30         40         50         60
-1--------X----------X----------X----------X----------X----------X
QEDERIVLVDNKCKCARITSRIIRSSEDPNEDIVERNIRIIVPLNNRENISDPTSPLRTRF
-DENERIV---------------P-A---SQ------V-------S----------M--K-
  D--ATI-A----M-T-V-----P-T---------------V----------------RN-
    ---ST-------Q-V--------DPDN-S----------------T------------E-
     EQEYI-AN-----VK-S--FVP-T-R-G-E-L----Q-TI-TSS-MX----Y-----Q-
            ---M-T-V-A--RGTR----------Y---N---K--G----------NQ- 70         80         90        100        110        120
---------X----------X----------X----------X----------X----------X
VYHLSDLCKKCDPTEVELDNQIVTATQSNICDEDSAT ETCYTY     DRNKCYTAVVPL
------------T-----ED-V---S------S-A   ------    -------NR-K-
------V-------V----ED-V---------N--DGVP----M-   -------TM---
K-N-AN---------I-----VF--S-----PD-DYS ------    -------TL--I
--N-W-I-Q----VQL-IGGIP-L-S-PXXSKP-dE             ---TE-NF
-----PS------    YEDGV----ET---YP-QGVPQS-RD-CPEL-------VL--P 130        140
---------X----------X----------X---
VYGGETKMVETALTPDACYPD         HUMAN
S-R-Q-----------S----         BOVINE
R-H------QA-----S----         MOUSE
THR-V-R--KAT----S----         RABBIT
K       KKVP----S--EYSE       BULL FROG
G-T------QN---------          EARTH WORM
```

J CHAIN POLYPEPTIDE TARGETING MOLECULE LINKED TO AN IMAGING AGENT

TECHNICAL FIELD

The present invention relates generally to the targeting of diagnostic compounds to specific cells and tissues. The invention is more particularly related to targeting molecules for use in delivering compounds to epithelial tissue. Such targeting molecules may be used in a variety of diagnostic procedures.

BACKGROUND OF THE INVENTION

To improve the diagnosis of cancer and other disorders, some researchers have used the systemic administration of imaging agents (e.g., proton relaxation agents as well as fluorescent chromophores) for contrast enhancement in techniques such as magnetic resonance imaging (MRI) and laser phototherapy. For example, tumor location using radio-labeled antibodies and handheld probes for intraoperative tumor detection has been attempted (Arnold et al., *Surgery* 112:624–631, 1992). Introduction of fluorescein conjugated antibodies for endoscopic tumor location ("photo-immunodiagnosis") in animals and in humans has also been attempted (Folli et al., *Cancer Res.* 54:2643–2450, 1994; Pelegrin et al., *Cancer* 67:2529–2535, 1994). In addition, fluorochrome-conjugated antibodies have been used to study antibody circulation in tumor microvasculature and biodistribution in tumors.

While such techniques show promise, their use has been limited by a lack of agents or conjugates that show specific localization to particular cell types. For example, localization to cell populations that are frequent sites of neoplastic development would aid in the diagnosis of incipient tumors. Further selectivity for neoplastic cells or macroscopic tumors would greatly aid in their localization and excision.

The ability to target imaging compounds to epithelial cells would enhance a variety of diagnoses, since such cells give rise to a wide spectrum of tumors, as well as viral and bacterial infections. Targeting of imaging compounds to epithelial cells would ideally delineate normal tissue from neoplastic lesions and potentially identify other types of lesions such as infections. Refinement of cell type specificity to be selective for the abnormal cells would further aid in localizing and treating those cells. However, no techniques are currently available for such targeting of imaging agents.

Accordingly, there remains a need in the art for systems for delivering imaging agents to target cells, particularly epithelial cells and cells or tissues bounded by epithelial cells. The present invention fulfills these needs and further provides other related advantages.

SUMMARY OF THE INVENTION

Briefly stated, the present invention provides targeting molecules for the specific delivery of imaging agents to epithelial cells and tissues. In several aspects, the present invention provides a targeting molecule linked to at least one imaging agent. In one such aspect, the targeting molecule comprises a polypeptide that (a) forms a closed covalent loop; and (b) contains at least three peptide domains having β-sheet character, each of the domains being separated by domains lacking β-sheet character; wherein the polypeptide is not a full length dimeric IgA. In specific embodiments, the polypeptide further contains one or more of the following additional domains: a fourth peptide domain having β-sheet character, separated from other domains having β-sheet character by a domain lacking β-sheet character; a linear N-terminal domain; and a C-terminal domain, which may comprise a linear peptide having β-sheet character and/or a covalently closed loop.

Within other such aspects, the targeting molecule comprises a sequence recited in any one of SEQ ID NO:1–SEQ ID NO:8 and SEQ ID NO:13.

In a further related aspect, the present invention provides a targeting molecule capable of specifically binding to a basolateral factor associated with an epithelial surface and causing the internalization of an imaging agent linked thereto, wherein the targeting molecule is not full length dimeric IgA.

Within another such aspect, the targeting molecule comprises a polypeptide that: (a) forms a closed covalent loop; and (b) contains at least three peptide domains having β-sheet character, each of the domains being separated by domains lacking β-sheet character; wherein the targeting molecule is linked to at least one imaging agent by a substrate for an intracellular or extracellular enzyme associated with an epithelial barrier, or by a side chain of an amino acid in an antibody combining site.

Within yet another such aspect, the targeting molecule comprises a polypeptide that: (a) forms a closed covalent loop; and (b) contains at least three peptide domains having β-sheet character, each of the domains being separated by domains lacking β-sheet character; wherein the imaging agent is not naturally associated with the targeting molecule, and wherein the imaging agent is not iodine.

Within another aspect, the present invention provides a pharmaceutical composition comprising a targeting molecule linked to at least one imaging agent as described above in combination with a pharmaceutically acceptable carrier.

In further aspects, methods are provided for diagnosing a disease in a patient, comprising (a) administering to a patient a pharmaceutical composition as described above; and (b) detecting the presence of imaging agent within the patient.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 1 is a comparison of native J chain sequences reported for human (top line), mouse (second line), rabbit (third line), cow (fourth line), bull frog (fifth line) and earth worm (sixth line). For each non-human sequence, amino acid residues that are identical to those in the human sequence are indicated by a dash. Residues that differ from the human sequence are indicated using standard one letter abbreviations.

DETAILED DESCRIPTION OF THE INVENTION

As noted above, the present invention is generally directed to targeting molecules (TMs) for use in the delivery of imaging agents to epithelial cells. Upon delivery to an epithelial cell, extracellular enzymes at the basolateral surface may release an imaging agent from a TM in, for example, a region of a lesion. An imaging agent may remain within the target cell or may undergo transepithelial transport via transcytosis. For example, the agent and TM may be transported across the basolateral surface and remain within the epithelial cell, or the agent may remain within the cell while the TM undergoes transepithelial transport. Alternatively, both the agent and TM may undergo transcytosis. For example, an agent linked to a TM may pass through an epithelial cell surface to access an adjacent cell, tissue or compartment (e.g., lumen of the small intestine, bronchial airway, vaginal cavity).

Prior to setting forth the present invention in detail, definitions of certain terms used herein are provided.

Epithelial Surface (or Epithelial Barrier)

A surface lining the exterior of the body, an internal closed cavity of the body or body tubes that communicate with the exterior environment. Epithelial surfaces include the genitourinary, respiratory, alimentary, ocular conjunctiva, nasal, oral and pharyngeal cavities, as well as the ducts and secretory portions of glands and receptors of sensory organs. The term "epithelial surface" as used herein is synonymous with "epithelial barrier." One side of an epithelial surface is free of adherence to cellular and extracellular components, other than coating substances and secretions. The other side of the surface is normally adjacent to the basement membrane and is exposed to interstitial fluids and components of the underlying tissues. Epithelial surfaces are typically formed from cells in close apposition to one another, the contact between plasma membranes of adjacent cells characterized by a tight junction (zonula occludens) which delimits the outside and inside domains of an epithelial surface. An experimental epithelial-like surface can be generated in vitro with autonomously replicating cell lines (e.g., MDCK, ATCC No. CCL 34; HEC-1A, ATCC No. HTB 112), which form epithelial-like surfaces in culture, have tight junctions and articulate one free (apical) and one adherent (basolateral) domain.

Apical Domain

The outside of an epithelial surface which is adjacent to the environment external to the body or to the volume of a body cavity or body tube. The outside of the cells, as delimited by the zonula occludens, is composed of the coating substances, secretions and cell membranes facing the outside of the epithelial surface.

Luminal Compartment

The inner space of a body tube, cavity or duct lined by an epithelial surface and adjacent to the apical domain.

Basolateral Domain

The inside of the epithelial surface which is delimited from the apical domain by the zonula occludens. The basolateral domain is adjacent to the basement membrane and is exposed to interstitial fluids and components of the tissues underlying epithelial surfaces. The basolateral domain is the inner side of cells of an epidermal surface.

Basolateral Membrane

The portion of the plasma membrane of a cell of an epithelial surface which is within the basolateral domain.

Basolateral Factor

A component of the basolateral domain which is a naturally occurring element of a basolateral membrane in vivo. A "basolateral factor associated with an epithelial surface" refers to a basolateral factor attached by covalent or non-covalent bonds to the basolateral domain, or a component of the membrane proper in a basolateral domain.

Internalization

The process of uptake into a cell compartment that is bounded by a plasma membrane.

Specific Binding

A TM specifically binds to a basolateral domain if it specifically interacts at the basolateral domain of an epithelial surface. Both quantitative and qualitative assays may be used to distinguish specific binding from binding which is not specific within the context of the subject invention. A quantitative measurement of binding affinity ($k_{aff}$) may be used to identify components that bind specifically. In general, a $k_{aff}$ of $10^4$ $M^{-1}$ or higher constitutes specific binding between two binding components. The binding affinity for the cognate components of a binding interaction can be estimated experimentally by a variety of methods that are well known in the art, including equilibrium dialysis assays, precipitation radioimmunoassays, assays with immobilized ligands, assays with isolated cells or membranes, ELISAs, or by other direct or indirect measurements or binding (e.g., plasmon resonance).

Qualitative specificity of binding is demonstrated by differential, or asymmetric distribution of binding of a factor among two or more chemical, spatial or temporal domains. This differential distribution can be observed visually, or by chemical or physical means, and generally reflects approximately a 3 to 1 or greater differential in signal intensity between basolateral and non-basolateral domains. Such qualitative specificity may result from substantial differences in the affinity of binding of an agent to one of several domains, or to the number or availability of cognate binding sites on a domain. The qualitative specificity of binding of an agent among several domains can be observed in a competition experiment. In such an experiment a TM is allowed to distribute among domains, and at equilibrium is observed to preferentially bind to one domain over another.

Targeting Molecule (TM)

A molecule capable of specifically binding to a cognate factor on epithelial surfaces, which is not uniformly distributed.

Imaging Agent

Any substance administered to illuminate a physiological function within a patient, while leaving other physiological functions generally unaffected.

Linked

An imaging agent is linked to a TM if it is attached covalently, by ionic interaction and/or by hydrophobic interactions, or by other means such that under physiological conditions of pH, ionic strength and osmotic potential the linked entities are associated with each other at equilibrium.

TMs as described herein are generally capable of specifically binding to a factor preferentially distributed on an epithelial surface, such as a basolateral factor. Through binding to such a factor, TMs are capable of causing the internalization of an imaging agent linked to the TM. TMs as described herein have a distinct three-dimensional structure. In general, TMs comprise a polypeptide that forms a closed covalent loop which is referred to herein as the "core." All subunits of the polypeptide may, but need not, be connected by identical chemical bonds. In a preferred embodiment, the polypeptide comprises amino and/or imino acids covalently joined by peptide bonds and one or more cystine disulfide bridges.

The core of a TM typically contains at least three peptide domains having β-sheet character, interspersed among regions lacking β-sheet character. In this regard, a "peptide domain" is a portion of a polypeptide comprising at least three amino acid residues. A peptide domain is said to have β-sheet character if the peptide backbone has an extended conformation with side-chain groups in a near planar and alternating arrangement such that hydrogen bonding can occur between carbonyl and NH groups of the backbone of adjacent β-strands. Furthermore, TMs generally contain at least one cysteine residue not present within an intramolecular cystine. Such cysteine(s) may be used for linking one or more imaging agents to the TM, although other means of linking imaging agents are also contemplated.

One or more of a variety of other structures may, but need not, be additionally present within a TM. For example, a second peptide loop may be present within the core sequence. Additional N-terminal and/or C-terminal sequences may be present. If present, N-terminal sequences are usually linear. A preferred N-terminal sequence is a short (about 1–20 amino acid residues) peptide domain. C terminal sequences may be linear and/or may form one or more loops. Such sequences may, but need not, possess domains having β-sheet character. These and/or other protein domains may be added to the core by genetic means or chemically, using covalent bonds or noncovalent interactions.

In a preferred embodiment, a TM comprises all or a portion of a native J chain sequence, or a variant thereof. J chain is a 15 kD protein that, in vivo, links IgM or IgA monomers to form pentameric IgM or dimeric IgA (see Max and Korsmeyer, *J. Exp. Med.* 161:832–849, 1985). To date, sequences of J chains from six organisms have been deduced (see FIG. 1 and SEQ ID NO:1–SEQ ID NO:6; Kulseth and Rogne, *DNA and Cell Biol.* 13:37–42, 1994; Matsuuchi et al., *Proc. Natl. Acad. Sci. USA* 83:456–460, 1986; Max and Korsmeyer, *J. Exp. Med.* 161:832–849, 1985; Hughes et al., *Biochem J.* 271:641–647, 1990; Mikoryak et al., *J. Immunol.* 140:4279–4285, 1988; Takahashi et al., *Proc. Natl. Acad. Sci. USA* 93:1886–1891, 1996). A TM may comprise a native J chain from one of these organisms, or from any other organism.

Alternatively, a TM may comprise a portion or variant of a native J chain sequence. A variant is a polypeptide that differs from a native a sequence only in one or more substitutions and/or modifications. Portions and variants of the native J chain sequence contemplated by the present invention are those that substantially retain the ability of the native J chain to specifically bind to a basolateral factor associated with an epithelial surface, and cause the internalization of a linked imaging agent. Such portions and variants may be identified using, for example, the representative assays described herein.

Within the context of the TM compositions provided herein, the TM is not full length dimeric IgA. More specifically, the TM does not contain all of the components present within a naturally-occurring IgA (i.e., a heavy chain containing contiguous variable, $C_H1\alpha$, $C_H2\alpha$ and $C_H3\alpha$ domains and a light chain containing contiguous variable and $C_L$ domains). Such a TM may, of course, contain one or more portions of an IgA molecule, including an IgM.

As noted above, specific binding may be evaluated using quantitative and/or qualitative methods. In one representative quantitative assay, secretory component (SC) isolated from human milk by standard immunoaffinity chromatography methods (Underdown, B. J., DeRose, J., Koczekan, K., Socken, D., Weicker, J., *Immunochemistry* 14:111–120, 1977) is immobilized on a CM5 sensor chip with a BIACORE apparatus (Pharmacia, Piscataway, N.J.) by primary amine coupling. The sensor chip is activated by injection of 30 μL of 0.05M N-hydroxysuccinimide and N-ethyl-N-(3-diethylaminopropyl)carbodiimide, followed by injection of 25 μL of human SC (15 μg/mL) in 10 mM sodium acetate, pH 5.0. Unreacted carbodiimide is then quenched with 30 μL ethanolanine. All reagents are delivered at a flow rate of 5 μL per minute. To evaluate the kinetics of binding and desorption, serial two fold dilutions of TMs at concentrations between 100 μM and 100 nM are injected in binding buffer: 25 mM Tris, pH 7.2, 100 mM NaCl, 10 mM $MgCl_2$ at a flow rate of 20 μL per minute. Between dilutions, the surface is regenerated by injecting 50 μL of 25 mM Tris, pH 7.2, 200 mM NaCl, 2M urea, followed by injecting 50 μL of binding buffer. Association and dissociation constants are derived from sensograms using BIAevaluation 2.1 software to derive simple association($k_a$) and dissociation constants ($k_d$). The $K_{aff}$ is estimated as $k_a/k_d$.

In one representative qualitative assay, monolayers of HEC-1A cells can be used to measure qualitative binding of TMs. The procedure is based on previously published protocols (see Ball et al., *In Vitro Cell Biol.* 31: 96, 1995). HEC-1A cells are cultured on 24 mm filter transwells (Costar, #3412, 0.4 μm) for one week until cells are confluent. Monolayer-covered filter transwells are washed twice on both surfaces with cold PBS (4° C.). One ml of cold MEM-BSA containing 1.0 μg of biotinylated ligand is added to the apical chamber and 1.5 ml cold MEM-BSA buffer (MEM-BSA (4° C.): minimum essential medium with hank's salts, and 25 mM HEPES buffer without L-glutamine (Life Technologies, Gaithersburg, Md. Cat. No. 12370) containing 0.5% BSA, which is treated at 56° C. for 30 min to inactivate endogenous protease and filter sterilized) containing 1.5 μg of biotinylated ligand is added to the basolateral chamber. The cultures are kept at 4° C. for 2 hours to achieve maximum binding in the absence of internalization. The medium is removed from both chambers, and the filters are washed twice with cold PBS. Filters are then remove from the transwell supports with a scalpel and incubated with a streptavidin-fluorescein conjugate (#21223, Pierce Chemical Company, Rockford, Ill.), 0.1 μg/mL in cold PBS, then washed 3 times with cold PBS. 1 cm square pieces of filter are then cut from the 24 mm filter and mounted on microscope slides and observed microscopically under epifluorescence illumination(excitation 490 nm, emission 520 nm). Under these conditions the apical membranes show little or no fluorescence, while basolateral membranes demonstrate bright fluorescence (i.e., greater than a 3 to 1 differential in signal intensity) indicating specific binding to the basolateral domain. Similar assays can be employed with isolated epithelial tissues from gastrointestinal, oral or bronchial epithelial tissue layers.

Once bound to the basolateral domain of an epithelial cell, a TM may be internalized within a cell of an epithelium-like monolayer. Suitable cells for evaluating internalization include MDCK cells expressing the human polyimmunoglobulin receptor (pIgR) (see Tamer et al., *J. Immunol* 155:707–714, 1995) and HEC1-A cells. One assay in which internalization can be observed employs a HEC1-A cell line grown to confluent monolayers on permeable membrane supports (such as Costar, Cambridge, Mass., #3412). Briefly, 100 ng to 10 μg of a TM (e.g., fluorescein labeled) may be added to 1.5 mL of assay buffer in the basolateral compartment of cell monolayers and incubated at a temperature that allows binding and internalization of TMs, but that inhibits transcytosis (e.g., 90 minutes at 16° C.). The medium from both compartments is then removed and the filter membranes washed (e.g., twice at 4° C. with PBS). The membrane is immersed in a fixation solution of, for example, 3% (w/v) paraformaldehyde, 1% (w/v) glutaraldehyde, 5% (w/v) sucrose, 100 mM Na phosphate pH 7.4 on ice for 30 minutes. The membranes may be removed from the plastic insert by cutting around the periphery with a scalpel and cut into 5 mm square sections. These wholemount sections may be placed on microscope slides and observed microscopically under epifluorescence illumination (excitation 490 nm, emission 520 nm) or by fluorescence confocal microscopy. Internalized TM is indicated by the presence of bright green-yellow fluorescence in intracellular vesicles.

Substitutions and modifications that result in a variant that retains the qualitative binding specificity for a basolateral factor (i.e., at least a 3 to 1 differential in signal intensity between basolateral and non-basolateral domains) are considered to be conservative. Preferred conservative substitutions and modifications include alterations in a sequence that render it, at least in part, consistent with the J chains of one or more other species. A TM may also, or alternatively, contain other sequences that confer properties not present in a native J chain. Other preferred modifications include the addition of one or more protein domains at the N- and/or C-terminus and/or altering the order of domains present within a native J chain sequence. A variant may contain any combination of such substitution(s) and/or modification(s), provided that the ability of the variant to specifically bind to an epithelial basolateral factor and cause internalization of the linked imaging agent is not substantially reduced.

A native J chain typically has 6 domains. The first (N-terminal) domain is a short linear (i.e., as contrasted to a loop) peptide that serves (in vivo) as the junction between the signal peptide and the core TM molecule. Domain 1 typically contains 1–20 amino acid residues, and the first amino acid is generally D, E or Q. In FIG. 1, Domain 1 contains the amino acids up to and including residue number 11. Domain 1 is not essential for TM function, and variants that do not contain this domain are within the scope of the present invention.

Domain 2 typically contains 90 amino acids, and possesses substantial β-sheet character. This β-sheet region contains peptides of varying length lacking β-strand character (e.g., residues 26–31, 49–53), the peptides usually containing polar and/or charged amino acids. In a TM, Domain 2 is a covalently closed peptide loop, called the core, which is typically formed by an intramolecular cystine composed of the initial and ultimate residues of Domain 2 (residues 12 and 101 of FIG. 1). Within Domain 2, there may be another cystine bond that defines Domain 3, a peptide loop that is nested within the core. It has been found, within the context of the present invention, that the core (with or without Domain 3) is sufficient to provide TM function. Accordingly, a preferred TM contains Domain 2 (i.e., residues 12–70 and 92–101 of FIG. 1), or a portion or variant thereof that substantially retains TM function.

Within Domain 2, the second cysteine is generally separated from the initial cysteine of Domain 2 by a single amino acid residue (see, for instance, FIG. 1). Between the second and third cysteines of Domain 2 is a region of primarily β-sheet character. These two cysteines (2 and 3) when present, typically do not form cystines within the core. The fourth cysteine is typically separated from the third cysteine by two basic amino acid residues and initiates Domain 3. Domain 3 ends with the fifth cysteine which is oxidized by the fourth cysteine. The resulting cystine forms a covalent peptide loop defining Domain 3 contained completely within Domain 2. Cysteine 6 is the ultimate residue of Domain 2, and is oxidized to cystine by the initial residue of Domain 2.

Within the core is a canonical peptide sequence for N-linked glycosylation (e.g., NIS). When produced by eukaryotic cells, carbohydrate moieties can be covalently attached to an N residue of a TM at this site.

When present, Domain 3 is typically a peptide 21 amino acids in length. This domain is delimited by amino and carboxy terminal cysteine residues which form an intramolecular cystine bond that is contained completely within the core.

Domains 4–6 are carboxy terminal domains in native J chains which may, but need not, be present within a TM. Domain 4 is typically a peptide of seven amino acids. In native J chains, this peptide contains no cysteine residues and connects the core to Domain 5. Domain 5 is, when present, typically a peptide of 26 amino acids delimited by amino and carboxy terminal cysteine residues which form an intramolecular cystine bond resulting in a covalently closed loop. In native J chains, the amino and carboxy terminal portions of Domain 5 have substantial β-sheet character and are separated by a short 3–6 residue peptide with low β-sheet propensity. Domain 6 is typically a short peptide of five amino acids or less which serves as the carboxy terminus of a TM. Domains 4–6 are not essential for TM function.

As noted above, numerous variants of native J chain sequences may be employed within TMs as described herein. For example, a TM core, as described above, can serve as a molecular scaffolding for the attachment and/or substitution of Domains and/or additional molecular components. Possible variants include:

- TMs in which Domain 1 comprises a peptide of about 13 amino acids, the middle third of which has substantial β-sheet character (e.g., DQEDERIVLVDNK; SEQ ID NO:37);
- TMs in which the asparagine residue at position 48 is changed to histidine (e.g., AAT to CAC);
- TMs in which Domain 1 comprises a three amino acid peptide DNK;
- TMs in which Domain 1 contains a peptide with a sequence specific for recognition and cleavage by a protease which can be used to release distal portion of the TM from a proximal colinear peptide or protein (e.g., a peptide recognized by the tobacco etch virus protease Nia: ENLYFQS; SEQ ID NO:38);
- TMs in which Domain 1 contains a peptide sequence which specifies the intracellular targeting of the contiguous peptide (e.g., a nuclear targeting peptide);
- TMs in which one or both of the native cysteine residues 2 or 3 within Domain 2 are removed or replaced to eliminate the possibility of intermolecular crosslinking (e.g., substitutions of S, T, A, V or M residues for the native C);
- TMs in which a portion of Domain 3 is deleted, such that there is a peptide bond between the amino acid distal to the end of the third β-sheet of Domain 3 and the initial residue of the ultimate peptide of Domain 3;
- TMs in which other peptides that form loop structures or other antiparallel peptide domains are included in place of Domain 3, or between its defining cysteines, to provide functionalities or recognition domains to the TM (e.g., viral capsid protein loops);
- TMs in which Domain 4 is truncated to form a TM without Domains 5 and 6;
- TMs in which Domain 4 is replaced as described above for Domain 3 to introduce a new functionality, specificity and/or structure to the TM;
- TMs in which Domain 4 contains a proteolytic site specific for a cellular compartment which would result in cleavage of the TM into two molecules in a cellular compartment;
- TMs in which the loop structure of Domain 5 is replaced with a peptide sequence to provide functionalities or recognition domains to the TM (e.g., single chain antibody variable region or viral capsid protein loop);
- TMs in which Domain 6 is terminated in a peptide sequence or is replaced with a peptide sequence that would target the contiguous TM protein to an intracellular target (e.g., KDEL, SEQ ID NO:44, or HDEL, SEQ ID NO:86, for retention in the endomembrane system);

TMs that additionally comprise one or more immunoglobulin-derived sequences (e.g., domains of the Ig heavy chain classes: alpha3, alpha2, alpha1, mu4, mu3, mu2, mu1) linked via one or more disulfide and/or peptide bonds. Such sequences may serve as attachment sites for one or more biological agents.

The above list of representative variants is provided solely for illustrative purposes. Those of ordinary skill in the art will recognize that the modifications recited above may be combined within a single TM and that many other variants may be employed in the context of the present invention.

TMs may generally be prepared using any of a variety of well known purification, chemical and/or recombinant methods. Naturally-occurring TMs (e.g., human J chain) may be purified from suitable biological materials, as described herein. All or part of a TM can be synthesized in living cells, with the sequence and content defined by the universal genetic code, a subset of the genetic code or a modified genetic code specific for the living cells. Any of a variety of expression vectors known to those of ordinary skill in the art may be employed to achieve expression in any appropriate host cell. Suitable host cells include insect cells, yeast cells, mammalian cells, plant cells, algae, bacteria and other animal cells (e.g., hybridoma, CHO, myeloma).

An example of a synthetic gene encoding a targeting molecule is provided in SEQ ID NO:7. Such synthetic genes may be ligated into, for example, a polyhedrin-based baculovirus transfer vector such as pMelBac A, pMelBac B or pMelBac C (Invitrogen, San Diego, Calif.) between suitable restriction sites (e.g., the BamHI and SalI sites) and introduced into insect cells such as High Five, Sf9 or Sf21 in a cotransfection event using Bac-N-Blu AcMNPV DNA (Invitrogen, San Diego, Calif.) according to standard methods. Other suitable vectors and host cells will be readily apparent to those of ordinary skill in the art.

Synthetic polypeptide TMs or portions thereof having fewer than about 100 amino acids, and generally fewer than about 50 amino acids, may be generated using synthetic techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is readily available from suppliers such as Applied BioSystems, Inc., Foster City, Calif., and may be operated according to the manufacturer's instructions.

Linkage of a TM to one or more imaging agents may be achieved by any means known to those in the art, such as genetic fusion, covalent chemical attachment, noncovalent attachment (e.g., adsorption) or a combination of such means. Selection of a method for linking a TM to an imaging agent will vary depending, in part, on the chemical nature of the agent and depending on whether the agent is to function at the basolateral surface, within the epithelial cell, or undergo transcytosis. Linkage by genetic fusion may be performed using standard recombinant DNA techniques to generate a nucleic acid molecule that encodes a single fusion peptide containing both the imaging agent(s) and the TM. Optionally, a TM may also be linked to one or more linker sequences and/or sequences for intracellular targeting (e.g., KDEL, protease cleavage sites, etc.). Such sequences may be linked to a TM by genetic fusion using standard recombinant DNA techniques to generate a nucleic acid molecule encoding the TM and the desired additional sequences. The recombinant nucleic acid molecule is then introduced into an appropriate vector and expressed in suitable host cells. Techniques for generating such a recombinant molecule and expressing a fusion peptide are well known to those of ordinary skill in the art (see, e.g., Sambrook et al., *Molecular Cloning: A Laboratory Manual,* 2d ed., Cold Spring Harbor Laboratory, Cold Spring Harbor, N.Y., 1989). Any imaging agent having a known polypeptide sequence may be linked to a TM by genetic fusion.

Linkage may also be achieved by covalent attachment, using any of a variety of appropriate methods. For example, the TM and imaging agent(s) may be linked using bifunctional reagents (linkers) that are capable of reacting with both the TM and the imaging agent(s) and forming a bridge between the two. For delivery of agents that will remain within the epithelial cell, linkers that are cleaved within the target cell may be particularly useful. Covalent attachment of linkers may be accomplished through bonding to amino acid side chains present in the antigen combining site of an antibody linked to a TM. Briefly, attachment of linkers to these residues can occur as a result of the antibody recognition process itself when the linker is recognized as antigen and compatible reactive residues are present on the linker-antigen and in the binding domain of the antibody. Such reactive antibodies typically have antigen combining sites containing amino acid residues with side chains which can act as nucleophiles (e.g., aspartate, glutamate, glutamine, lysine and/or asparagine).

Any of a variety of molecules may serve as linkers within the present invention. Polynucleotide and/or peptide linkers may be used. Such molecules may then be digested by, for example, intestinal nucleases and proteases (e.g., enterokinase, trypsin) respectively to release the imaging agent. Preferred linkers include substrates for intracellular proteases associated with an epithelial barrier (i.e., proteases resident in or on epithelial cells or surfaces, or in the extracellular fluids exposed to the apical or basolateral domains). Numerous proteases are present in or associated with epithelial cells. For example, linkers can be derived from the sequences of the extracellular matrix (ECM) proteins which are acted on by specific secreted proteases. Some secreted proteases are especially active in the extracellular fluids adjacent to cancerous epithelial cells which are becoming metastatic (e.g., gelatinase A, gelatinase B, matrilysin, stromelysin-1, stromelysin-2, stromelysin-3, collagenase-3, membrane-type matrix metalloproteinase). These proteases degrade ECM components with which the basolateral domain of epithelial cells associate (e.g., the basement membrane). This degradation is prerequisite to cellular release from the epithelial surface and thus to subsequent intravasation and metastasis. Proteolytic cleavage sites of these proteases can be identified by evaluation of the amino acid sequence of the cleavage products and comparison of these sequences to the sequences of the ECM substrate. These cleavage sites are particularly useful in scissile linkers which allow efficient cleavage from TM of imaging agents in epithelial regions where these proteases are active, delivering an imaging agent to the basolateral domain. Imaging agents linked to TM with such linkers associate with basolateral factors in other epithelial regions, but are transported through the epithelial barrier and do not remain associated with the basolateral domain.

Processing of secreted proteins requires proteolytic scission of a portion of the newly synthesized protein (referred to as the pre-protein) prior to secretion from the cellular endomembrane system. Further processing, which may be required to liberate an active enzyme from the cell, for example, can result from additional proteolysis wherein the substrate may be referred to as the pro-protein or pro-enzyme. The specific proteolytic cleavage sites of these pro-proteins can be identified by comparison of the amino acid sequence of the final secreted protein with the sequence of the newly synthesized protein. These cleavage sites identify the substrate recognition sequences of particular intracellular proteases. One such protease recognition site, specific to epithelial cells, is the amino acid sequence from residues 585–600 of the human polyimmunoglobulin receptor (pIgR (SEQ ID NO:45); numbering according to Piskurich et al., *J. Immunol.* 154:1735–1747, 1995). Another such protease recognition site, which identifies proteases abundant in cancer cells, comprises residues 30–40 of procathepsin E (SEQ ID NO:39). Since cancer cells secrete abundant quantities of proteases, the intracellular proteases which are responsible for their processing are also in abundance.

These protease recognition sites are extremely useful in the design of scissile linkers enabling the delivery of imaging agents to the intracellular environment of epithelial cells or to the epithelial barrier in general. Delivery of such compounds to epithelial cells can be accomplished by using residues 585–600 of human pIgR (SEQ ID NO:45) or residues 30–40 of procathepsin E (SEQ ID NO:39) as part of the scissile linker joining the imaging agent to TM. Alternatively, scissile linkers may be designed from other cancer cell specific or epithelial barrier specific processing proteases which may be identified by the comparison of newly synthesized and secreted proteins or similar techniques. Other types of proteases that can be used to cleave scissile bonds can be found in the mammalian duodenum, for example. The enterokinase recognition sequence, $(Asp)_4$-lys, can be used as a scissile linker for delivery of imaging agents to the duodenum by TM mediated transcytosis across the duodenum epithelial barrier.

Scissile peptide linkers are generally from about 5 to about 50 amino acid residues in length. They can be covalently linked to TM or to adducts attached to TM by genetic fusion techniques (i.e., in frame with the 5' or 3' sequence of TM codons or adduct codons) or by any of a variety of chemical procedures enabling the joining of various functional groups (e.g., $NH_2$, COOH, SH).

Other substrates for intracellular proteases associated with an epithelial barrier include, but are not limited to, substrates for a phospholipase or glycosidase. Proteolytic cleavage releases the imaging agent with a small fragment of linker (e.g., VQYT (SEQ ID NO:40) from procathepsin, EKAVAD (SEQ ID NO:41) from pIgR). Alternatively, a linker may comprise repeating positively charged lysine residues that will bind negatively charged nucleic acid molecules for release in the cell. Peptide linkers may be particularly useful for peptide imaging agents.

Carbohydrates may be covalently attached to native carbohydrate or to the polypeptide backbone of a TM, and employed as linkers. Suitable carbohydrates include, but are not limited to, lactose (which may degraded by a lactase residing in, for example, the small intestine), sucrose (digested by a sucrase) and α-limit dextrin (digested by a dextrinase). Enzymes responsible for cleaving carbohydrate linkers can be found attached to the brush border membranes of the luminal surface of the epithelial barrier. Sucrase-isomaltase, for example, will cleave 1,4-α bonds of maltose, maltotriose and maltopentose. An intestinal brush border specific linker would therefore be comprised of any polymer of maltose linked by 1,4-α bonds. When attached to TM, the linker would pass through the epithelial barrier by transcytosis and would only be cleaved by sucrase-isomaltase resident on the apical surface of the epithelial barrier.

Lipids may also, or alternatively, be covalently attached to the polypeptide backbone for use as linkers. A monoglyceride employed in this manner may then be digested by intestinal lipase to release an imaging agent linked to glycerol or a fatty acid. Phospholipids may be attached to a TM via a peptide linkage to the phosphatidylserine polar head group or by an ether or ester linkage to one of the hydroxyl groups of the head group of phosphatidyl inositol. The non-polar head group (diacylglycerol) may be substituted entirely by the imaging agent in active or inactive form. Other suitable linker moieties will be apparent to those of ordinary skill in the art.

Linkage may also be performed by forming a covalent bond directly between a TM and an imaging agent. Regardless of whether a linker is employed, any of a variety of standard methods may be used to form a covalent linkage. For peptide imaging agents and linkers, such a covalent bond may be a disulfide bond between cysteine residues of the TM and the imaging agent. Briefly, such bonds may be formed during the process of secretion from the endomembrane system of higher organisms. In such cases, the peptide biological agent(s) and TM must contain appropriate signals specifying synthesis on endomembranes. Such signals are well known to those of ordinary skill in the art. Alternatively, free amino or sulfhydryl groups of a TM may be covalently linked to a reactive group of an imaging agent, using standard techniques. For example, reaction of free amino groups of a TM with the NHS moiety of NHS-cyanine will result in covalent attachment. Alternatively, cyanine dyes can be derivatized to contain sulfhydryl reactive components (e.g., sulfo-MBS (Pierce Chemical Co., Rockford, Ill.; or by reaction with SPDP [N-succinimidyl-3-[2-pyridylthio] propionate]), which can be used for attachment to free sulfhydryls of a TM.

Reactive antibodies may covalently attach directly to an imaging agent or a linker. Antibodies raised against antigens containing reactive groups or transition state analogs for specific reactions may contain residues in the combining site capable of forming covalent interactions with the antigen or with similar molecules. An example of such a reaction occurs between a lysine residue in the combining site of the monoclonal antibody 38C2 which reacts to form a vinylogous amide linkage with diketone and other closely related molecules (Wagner et al., *Science* 270:1797–1800, 1995). A TM containing a reactive antibody or the combining site of a reactive antibody can be used to form covalent bonds with linkers of lipid, peptide, carbohydrate, nucleic acid or other compositions. TMs containing imaging agents attached to TM via covalent bonds in the combining site can be expected to have normal conformations and functions in the antibody domain. The absence of modifications to antibody structure outside the antigen combining site may minimize the potential for altering the recognition of such molecules as foreign when introduced into the body. Further, antibodies of human origin with reactive site tethered imaging agents could be expected to have half-lives in serum and other body compartments similar to those of native antibodies and have low propensity to stimulate antibody responses against the TM.

As noted above, any diagnostic imaging agent may be linked to a TM. Imaging agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a calorimetric or fluorometric reaction. In general, such agents may be attached using a variety of techniques as described above, and may be present in any orientation.

In one preferred embodiment, a targeting molecule as described above is linked to a imaging agent that is not naturally associated with the targeting molecule. Within the context of this embodiment, the imaging agent is not iodine.

An imaging agent linked to a TM is generally administered to a patient in the form of a pharmaceutical composition. To prepare a pharmaceutical composition, one or more TM-imaging agent complexes are mixed with a suitable pharmaceutical carrier or vehicle. Pharmaceutical carriers or vehicles include any such carriers known to those skilled in the art to be suitable for the particular mode of administration.

The compositions of the present invention may be prepared for administration by a variety of different routes, including orally, parenterally, intravenously, intradermally, subcutaneously or topically, in liquid, semi-liquid or solid form and are formulated in a manner suitable for each route of administration. Preferred modes of administration depend upon the indication treated.

Solutions or suspensions used for oral, parenteral, intradermal, subcutaneous or topical application can include one or more of the following components: a sterile diluent, saline solution (e.g., phosphate buffered saline), fixed oil, polyethylene glycol, glycerin, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of toxicity such as sodium chloride or dextrose. In addition, other pharmaceutically active ingredients and/or suitable excipients such as salts, buffers, stabilizers and the like may, but need not, be present within the composition. Liposomal suspensions may also be suitable as pharmaceutically acceptable carriers. These may be prepared according to methods known to those skilled in the art.

A TM may be prepared with carriers that protect it against rapid elimination from the body, such as time release formulations or coatings. Such carriers include controlled release formulations, such as, but not limited to, implants and microencapsulated delivery systems, and biodegradable, biocompatible polymers, such as ethylene vinyl acetate, polyanhydrides, polyglycolic acid, polyorthoesters, polylactic acid and others.

A pharmaceutical composition is generally formulated and administered to exert a useful effect while minimizing undesirable side effects. The number and degree of acceptable side effects depends upon the condition to be diagnosed. For example, certain toxic and undesirable side effects are tolerated when diagnosing life-threatening illnesses, such as tumors, that would not be tolerated when diagnosing disorders of lesser consequence. The concentration of imaging agent in the composition will depend on absorption, inactivation and excretion rates thereof, the dosage schedule and the amount administered, as well as other factors known to those of skill in the art.

The composition may be administered one time, or may be divided into a number of smaller doses to be administered at intervals of time. The precise dosage and duration of administration is a function of the disease being diagnosed and may be determined empirically using known testing protocols or by extrapolation from in vivo or in vitro test data. For any particular subject, specific dosage regimens may be adjusted over time according to the individual need of the patient.

The following Examples are offered by way of illustration and not by way of limitation.

EXAMPLES

Example 1

Preparation of Targeting Molecules

This Example illustrates the preparation of representative targeting molecules.

A. Purification of Representative TMs from Biological Sources

Preparation of Dimeric IgA (dIgA)

Ten ml of human IgA myeloma plasma (International Enzymes, Inc.; Fallbrook, Calif.) is mixed with an equal volume of PBS, and 20 ml of saturated ammonium sulfate ($H_2O$) is added dropwise with stirring. After overnight incubation at 4° C., the precipitate is pelleted by centrifugation at 17,000×g for 15 minutes, and the supernatant fraction is discarded. The pellet is resuspended in 2 ml PBS. The resulting fraction is clarified by centrifugation at 13,500×g for 5 minutes and passage through a 0.45 µm filter (Nylon 66, 13 mm diameter, Micron Separations, Inc., Westborough, Mass.). Two ml (about half) of the clarified fraction is applied to a Sephacryl® S-200 column (1.6×51 cm; 0.25 ml/min PBS+0.1% sodium azide) (Pharmacia, Piscataway, N.J.), and 2 ml fractions are collected. Those fractions found to have the highest concentrations of dIgA (by SDS-PAGE analysis of 10 µl of each fraction) are lyophilized, resuspended in 200 µl deionized $H_2O$, and applied to a Superose® 6 column (1.0×30 cm; 0.25 ml/min PBS+0.1% sodium azide) (Pharmacia, Piscataway, N.J.). One ml fractions are collected and analyzed by SDS-PAGE. Fraction 13 is found to contain dIgA at over 90% purity.

Preparation of J Chain by Mild Reduction of dIgA

A 1 ml sample containing less than 10 mg of dIgA is prepared as described above and dialyzed against buffer containing 100 mM sodium phosphate pH 6.0 and 5 mM EDTA. Six mg 2-mercaptoethylamine HCl are added to yield a final concentration of 0.05M, and the sample is incubated at 37° C. for 90 minutes. The reduced protein is passed over a desalting column equilibrated in PBS+1 mM EDTA. The protein-containing fractions are detected by assay with BCA reagent. J chain is then further purified by gel filtration and ion exchange chromatography.

Preparation of Secretory IgA (sIgA)

One hundred ml of human breast milk (Lee Scientific, Inc.; St. Louis, Mo.) is mixed with 100 ml PBS and centrifuged at 17,000×g for 1 hour at 4° C. The clear layer below the fat is transferred to clean centrifuge bottles and centrifuged at 17,000×g for 30 minutes at 4° C. The pH of the sample is adjusted to 4.2 with 2% acetic acid. After incubation at 4° C. for 1 hour, the sample is centrifuged at 17,000×g for 1 hour at 4° C., and the supernatant fraction is transferred to new tubes and adjusted to pH 7 with 0.1M NaOH. An equal volume of saturated ammonium sulfate is added, with stirring, and the sample is incubated at 4° C. overnight. The precipitated material is pelleted by centrifugation (17,000×g, 90 minutes, 4° C.), resuspended in approximately 7 ml PBS, and dialyzed extensively against PBS at 4° C.

Of the resulting approximately 25 ml, 1.1 ml is further purified. Undissolved solids are removed by centrifugation (13,500×g, 10 minutes) and an equal volume of 0.05M ZnSO$_4$ is added to the clarified supernatant fraction. The pH is adjusted to 6.85 by addition of approximately 40 µl 1M NaOH. After allowing the material to sit for 5 minutes at room temperature, the sample is centrifuged at 13,500×g for 10 minutes at room temperature. One and a half ml of the supernatant is mixed with 1.5 ml of saturated ammonium sulfate and allowed to stand at 4° C. for 1 hour. Precipitating material is pelleted by centrifugation (13,500×g, 10 minutes, room temperature) and is found to be greater than 90% sIgA by SDS-PAGE analysis.

Preparation of a Molecule Consisting of Nicked J-chain Crosslinked to Two Alpha-chain-derived Peptides (CNBr Cleavage Fragment)

A pellet containing sIgA prepared as described above ("Preparation of sIgA") is resuspended in 375 µl deionized H$_2$O. The sample is transferred to a glass vial and the vial is filled almost to the rim with 875 µl formic acid. Approximately 20 mg solid CNBr is added and a Teflon septum is used to seal the vial. The reaction is allowed to proceed at 4° C. overnight.

The sample is then dialyzed against deionized H$_2$O (two changes) and against PBS at 4° C., and lyophilized, resuspended with 200 µl H$_2$O, and applied to a Superose® 6 column (1.0×30 cm, 0.25 ml/min PBS+0.1% sodium azide). One ml fractions are collected. The fractions containing J chain are identified by immunoblotting of SDS-PAGE-separated proteins from aliquots of each fraction.

The fraction with the highest concentration of J chain is passed through a PD-10 column (Pharmacia, Uppsala, Sweden) equilibrated in 50 mM Tris-Cl pH 8.1, and applied to a 20 PI Poros anion exchange column (4.6 mm×100 mm; PerSeptive Biosystems, Inc., Framingham, Mass.). The column is washed with 10 ml of 50 mM Tris-Cl pH 8.1, and eluted with a linear 0–1.0M NaCl gradient in 50 mM Tris-Cl pH 8.1 (15 ml gradient). Elution of proteins from the column is monitored as absorbance at 280 nm and the J chain-containing fractions are identified by immunoblotting of SDS-PAGE-separated aliquots.

Alternative Methods for J Chain Purification

A variety of sources are suitable as starting material for isolation of human J chain. Polymeric IgA from sera of patients with IgA multiple myeloma, secretory IgA or IgM from sera of patients with Waldenstroms macroglobulinemia, as well as secretory IgA from human breast milk can be used as starting material for purification of J chain. Although the differences in the molecular weights of J chain (16,000) and L chains (22,500) should be large enough to allow satisfactory separation of these two chains by gel filtration, the unique conformation of J chain and its ability to dimerize often results in co-elution of J chain with L chain. Isolation procedures take advantage of J chain's negative charge (due to the high content of aspartic and glutamic acid residue) further increased by S-sulfitolysis or alkylation of reduced cysteine residues with iodoacetic acid. J chain can be subsequently separated from H and L chains by DEAE- or CM-cellulose chromatography using a linear salt gradient or by preparative electrophoresis in the presence or absence of dissociating agents.

Purification on DFAE-cellulose, which Results in the Isolation of Immunochemically and Physicochemically Homogeneous J Chain As a starting material, the J chain-containing L chain fraction of polymeric IgA, S-IgA, or IgM, obtained by partial oxidative sulfitolysis and subsequent gel filtration on Sephadex® G-200 in 5M guanidine-HCl can be used. Alternatively, S-sulfonated IgA or S-IGA can be directly applied on DEAE-cellulose. However, it is usually necessary to perform an additional separation using gel filtration on Sephadex® G-200 in 5M guanidine-HCl to remove contaminating H chains.

Starting materials consist of the following reagents: L chain fraction of serum polymeric IgA or IgM, or colostral S-IgA; 0.01M disodium phosphate in deionized 8M urea solution and the same buffer with 0.7M NaCl; DEAE-cellulose equilibrated in 0.01M disodium phosphate containing 8M urea; Sephadex® G-25 column in 1% NH$_4$HCO$_3$ solution.

Lyophilized L chain fraction is dissolved in 0.01M disodium phosphate in 8M urea, and applied on a DEAE-cellulose column equilibrated in the same phosphate solution. The column is thoroughly washed with this buffer. Absorbed proteins are eluted with a linear gradient of 0.01M disodium phosphate in 8M urea and 0.01M disodium phosphate with 0.7 M NaCl. Two fractions are obtained, the later fraction containing J chain.

The J chain-containing fraction is desalted on a Sephadex® G-25 column in 1% NH$_4$HCO$_3$ adjusted to neutrality by bubbling with CO$_2$. The purity of J chain can be assessed by alkaline-urea gel-electrophoresis or immunoelectrophoresis with anti- L, H, and J chain reagents.

B. Direct Synthesis of TM Polypeptides

Manual syntheses are performed with BOC-L-amino acids purchased from Biosearch-Milligen (Bedford, Mass.). Machine-assisted syntheses are performed with BOC-L-amino acids from Peptide Institute (Osaka, Japan) and Peptides International (Louisville, Ky.). BOC-D-amino acids are from Peptide Institute. BOC-L-His(DNP) and BOC-L-Aba are from Bachem Bioscience (Philadelphia, Pa.). Boc-amino acid-(4-carboxamidomethyl)-benzyl-ester-copoly(styrene-divinylbenzene)resins [Boc-amino acid-OCH2-Pam-resins] are obtained from Applied Biosystems (Foster City, Calif.) and 4-methylbenzhydrylamine (4MeBHA) resin is from Peninsula Laboratories, Inc. (Belmont, Calif.). Diisopropylcarbodiimide (DIC) is from Aldrich, and 2-(IH-benzotriazol-t-yl)-1,1,3,3-tetramethyluroniumhexafluorophosphate (HBTU) is obtained from Richelieu Biotechnologies (Quebec, Canada). For manual syntheses NN-diisopropylethylamine (DIEA), NN-dimethylformamide (DMF), dichloromethane (DCM) (all peptide synthesis grade) and 1-hydroxybenzotriazole (HOBT) are purchased from Auspep (Melbourne, Australia). For machine-assisted syntheses, DIEA and DCM are from ABI, and DMF is from Auspep. Trifluoroacetic acid (TFA) is from Halocarbon (New Jersey). Acetonitrile (HPLC grade) is obtained from Waters Millipore (Milford, Mass.). HF is purchased from Mallinckrodt (St. Louis, Mo.). Other reagents and solvents are ACS analytical reagent grade. Screw-cap glass peptide synthesis reaction vessels (20 mL) with a #2 sintered glass filter frit are obtained from Embel Scientific Glassware (Queensland, Australia). A shaker for manual solid phase peptide synthesis is obtained from Milligen (Bedford, Mass.). An all-Kel F apparatus (Toho; from Peptide Institute, Osaka) is used for HF cleavage. Argon, helium and nitrogen (all ultrapure grade) are from Parsons (San Diego, Calif.).

Chain Assembly

Syntheses are carried out on Boc-amino acid-OCH2-Pam-resins, or on 4-MeBHA-resin. Boc amino acids are used with the following side chain protection: Arg(Tos); Asp (OBzl) (manual synthesis) and Asp(OcHxl); Cys(Bzl) (machine-assisted synthesis); Asn, unprotected (manual synthesis) and Asn(Xan) (machine-assisted synthesis); Glu (OcHxl); His(DNP); Lys(2CIZ); Thr(Bzl); Trp(InFormyl); and Tyr(BrZ). Gln and Met are used side chain unprotected.

Manual Protocol

Syntheses are carried out on a 0.2 mmol scale. The $N^{\alpha}$-Boc group is removed by treatment with 100% TFA for 2×1 minute followed by a 30 second flow with DMF. Boc amino acids (0.8 mmol) are coupled, without prior neutralization of the peptide-resin salt, as active esters preformed in DMF with either HOBt/DIC (30 minute activation), or HBTU/DIEA (2 minute activation) as activating agents. For couplings with active esters formed by HOBt/DIC, neutralization is performed in situ by adding 1.5 equivalents of DIEA relative to the amount of TFA $O^-.^+NH_3$-peptide-resin salt to the activated Boc-amino acid/resin mixture. For couplings with active esters formed from HBTU/DIEA, an additional 2 equivalents DIEA relative to the amount of TFA $O^-.^+NH_3$-peptide-resin salt are added to the activation mixture. Coupling times are 10 minutes throughout without any double coupling. Samples (3–5 mg) of peptide-resin are removed after the coupling step for determination of residual free oc-amino groups by the quantitative ninhydrin method. Coupling yields are typically >99.9%. All operations are performed manually in a 20 mL glass reaction vessel with a Teflon-lined screw cap. The peptide-resin is agitated by gentle inversion on a shaker during the NII-deprotection and coupling steps.

Deprotection and Cleavage

His(DNP)-containing peptides are treated with a solution of 20% mercaptoethanol/10% DIEA in DMF for 2×30 minutes in order to remove the DNP group, prior to the removal of the Boc group. The $N^{\alpha}$-Boc group is removed from the peptide-resin by treatment with neat TFA (2×1 minute). The peptide-resin is washed with DMF and neutralized with 10% DIEA in DMF (1×1 minute). After removal of the DNP and Boc group, the peptide-resin is treated with a solution of ethanolamine in water/DMF for 2×30 minutes to remove the formyl group of Trp(InFormyl).

The partially-deprotected peptide-resin is dried under reduced pressure after washing with DMF and DCM. Side chain protecting groups are removed and simultaneously the peptide is cleaved from the resin by treatment with HF/p-cresol (9:1 v/v, 0° C., 1 hour) or HF/p-cresol/thiocresol (9:0.5:0.5 by vol., 0° C., 1 hour). The HF is removed under reduced pressure at 0° C. and the crude peptide precipitated and washed with ice-cold diethyl ether, then dissolved in either 20% or 50% aqueous acetic acid, diluted with $H_2O$ and lyophilized.

Peptide joining

Joining of peptide segments of TM produced by the synthetic procedures described above is carried out by chemical ligation of unprotected peptides. These procedures can yield a free sulfhydryl at the junctional peptide bond or can yield a disulfide bond. Alternatively, cysteine residues at specified positions are replaced by L-aminobutyric acid.

In one procedure, the synthetic segment peptide 1, which contains a thioester at the $\alpha$-carboxyl group, undergoes nucleophilic attack by the side chain of the Cys residue at the amino terminal of peptide 2. The initial thioester ligation product undergoes rapid intramolecular reaction because of the favorable geometric arrangement (involving a five-membered ring) of the $\alpha$-amino group of peptide 2, to yield a product with the native peptide bond of a cysteine moiety at the ligation site. Both reacting peptide segments are in completely unprotected form, and the target peptide is obtained in final form without further manipulation. Additional cysteine residues in either peptide 1 or peptide 2 are left in their reduced state.

In another procedure, unprotected peptide segments containing terminal cysteine moieties are ligated via nucleophilic attack of a deprotonated $\alpha$-thioacid group on a bromoacetyl moiety to form two monomers each with a short N- or C-terminal extension containing an unprotected sulfhydryl group. After derivatization of the cysteamine-containing monomer with 2,2'-dipyridyl disulfide, the desired disulfide-linked heterodimer is formed by thiolysis of the S-(2-pyridyisulfenyl)cysteamine derivative.

These procedures are used to derive a variety of TM configurations, such as the representative TMs provided below:

TABLE I

Direct Synthesis of TM Polypeptides

| Segments | Chemistry | Strategy to form Closed Covalent Loop | Representative Attachment Sites |
|---|---|---|---|
| A. TM Core | | | |
| 1. 12–71 | N—cysteine | 71 to 91 via disulfide | sulfhydryls at 14 |
|  | C—glyNH$_2$CH$_2$CH$_2$SH | linker; 12 to 101 via | and 68 |
| 2. 91–101 | N—glyCOCH$_2$SH | renaturation and | |
|  | C—cysteine | oxidation to disulfide | |
| B. TM Core | | | |
| 1. 31–71 | N—BrCH$_2$Co | 71 to 91 via disulfide | sulfhydryls at 14 |
|  | C—glyNH$_2$CH$_2$CH$_2$SH | linker; 30 to 31 via | and 68 |
| 2. 91–30 | N—glyCOCH$_2$CH | thioester; 12 to 101 | |
|  | C—thioacid | exists as peptide | |
|  |  | bonds (serine—glycine— | |
|  |  | alanine in place of cys | |
|  |  | to cys disulfide) | |

TABLE I-continued

Direct Synthesis of TM Polypeptides

| Segments | Chemistry | Strategy to form Closed Covalent Loop | Representative Attachment Sites |
|---|---|---|---|
| C. TM Extended | | | |
| 1. 1–67 | N—NH$^{3+}$ C—thioester | 67 to 68 via native chemical ligation; 118 to 119 via thioester; 71 to 91, 12 to 101 and 108 to 133 via renaturation and oxidation to form disulfides | sulfhydryls at 14 and 68 |
| 2. 68–118 | N—cysteine C—thioacid | | |
| 3. 119–136 | N—BrCH$_2$CO C—COO$^-$ | | |
| D. TM Core Variations | | | |
| 1. serin 68 serine 14 | Same as A or B | Same as A or B | sulfhydryl at 14; sulfhydryl at 68; free amines or free carboxyls |
| 2. serine 68 + serine 14 | " | " | |
| E. TM Extended Variations | | | |
| 1. 1–70 | N—NH$^{3+}$ C—thioester | 67 to 68 via native chemical ligation; 118 to 119 via thioester; 71 to 91, 12 to 101 and 108 to 133 via renaturation and oxidation to form disulfides; serines at 14 and 68 | reactive group at 136 for attachment of bromoacetylated peptide linker |
| 17–118 | N—cysteine C—thioacid | | |
| 119–136 | N—BrCH$_2$Co C—glyNH$_2$CH$_2$CH$_2$SH | | |
| 2. 1–70 | N—BrCH$_2$Co C—thioester | 67 to 68 via native chemical ligation; 118 to 119 via thioester; 71–91, 12 to 101 and 108 to 133 via renaturation and oxidation to form disulfides; serines at 14 and 68 | reactive group at 1 for attachment of sulfhydryl peptide linker |
| 71–118 | N—cysteine C—thioacid | | |
| 119–136 | N—BrCH$_2$CO C—COO$^-$ | | |

"Extended" = a TM comprising the 88 residues of the core, plus an additional 48 residues derived from native J chain; "Core" = residues 12–101 of native J chain; residues are indicated according to the numbering in FIG. 1

C. Synthesis and Expression of DNAs Encoding TM

DNA chains can be synthesized by the phosphoramidite method, which is well known in the art, whereby individual building block nucleotides are assembled to create a desired sequence. Automated DNA synthesis of TM DNAs involves the synthesis and joining of individual oligonucleotides encoding portions of TMs to form the entire desired sequence. Synthetic DNA can be purchased from a number of commercial sources.

Transgenic expression of TMs requires ligation of the synthetic coding DNA into a vector for transformation of the appropriate organism. Techniques of ligation into vectors are well described in the literature. For example, in order to enable the introduction and expression of TMs in insect cells, the synthetic TM DNA is ligated into the pFastBac1 vector (GibcoBRL) to form the pFastBac1-TM recombinant. The recombinant vector is then used to transform *E. coli* bacteria containing a helper plasmid and a baculovirus shuttle vector. High molecular weight shuttle vector DNA containing transposed TM coding sequences is then isolated and used for transfection of insect cells. Recombinant baculovirus are harvested from transfected cells and used for subsequent infection of insect cell cultures for protein expression.

A TM can be synthesized by expressing in cells a DNA molecule encoding the TM. The DNA can be included in an extrachromosomal DNA element or integrated into the chromosomal DNA of the cell expressing the TM. Alternatively, the TM DNA can be included as part of the genome of a DNA or RNA virus which directs the expression of the TM in the cell in which it is resident. An example of a DNA sequence encoding TM is shown in SEQ ID NO:7. This DNA sequence and the amino acid sequence encoded by this TM DNA are also shown in Table II.

One method of synthesizing such a TM gene involves the sequential assembly of oligonucleotides encoding portions of the TM gene into a complete TM gene. The final assembly of the TM gene can occur in a DNA expression vector suitable for expression in a cellular system, or the TM gene can be constructed in a convenient cloning vector and subsequently moved into a DNA expression vector suitable for expression in a cellular system. An advantage of the sequential assembly of the TM gene from partial coding regions is the ability to generate modified versions of the TM gene by using alternative sequences for one or more of its individual portions during the assembly of the TM gene. Alternatively, the restriction endonuclease sites encoded in the TM gene can be used after the assembly of part or all of the TM gene to replace portions of the TM coding sequence to generate alternative TM coding sequences, as described by Sambrook et al., *Molecular Cloning: A Laboratory Manual*, 2d ed., Cold Spring Harbor Laboratory, Cold Spring Harbor, N.Y., 1989. The TM gene can be divided into several partial coding regions: D1 encoding amino acids approximately −2 to 20; C2 encoding amino acids approximately 19 to 66; L3 encoding amino acids approximately 65 to 102; and T4 encoding amino acids approximately 102 to 142 of the sequence recited in Table II. Unless otherwise indicated, references to amino acid residue numbers in the following section are to the residue indicated in Table II.

Assembly of a Synthetic Gene Encoding TM Core Polypeptide

A TM Core gene sequence may be defined by the combination of C2, D1.1 (a modified version of D1, and L3Δ (a modified version of L3). One version of TM Core may be generated from the oligonucleotides 1.1, 2.1, 3, 4, 5, 6, 7, 8, 9L3Δ and 10L3Δ (SEQ ID NOs:48, 49, 54–56, 58, 60, 61, 63, 64) listed in Table III and encodes a polypeptide of sequence:

DQKCKCARITSRIIRSSEDPNEDI-VERNIRIIVPLNNRENISDPTSPLRTRFV YHLS DLCKKD-EDSATETC (Table VIII and SEQ ID NO:18).

A gene containing D1.1, C2, and L3Δ or alternate coding sequences that differ only in conservative substitutions or modifications is a complete TM Core gene.

allowing the oligonucleotides to form base-paired DNA duplexes. After incubating for 30 minutes at room temperature, 1 nanomole of each oligonucleotide pairs, ([e.g., (3&4), (5&6), and (7&8)], are combined in a single microcentrifuge tube. The tube containing these DNA duplexes is incubated at 55° C. for 15 minutes in a heating block, removed from the heating block and equilibrated to room temperature, allowing overlapping complementary regions of the DNA duplexes to anneal, forming a DNA duplex encoding the partial TM DNA C2.

One nanomole of the oligonucleotide duplex is then mixed with 0.1 picomole of pMelBac XP which has previously been restricted with endonucleases Xba I and Bgl II. pMelBac XP is a DNA vector for cloning and subsequent expression in insect cells of synthetic TM genes, derived from pMelBac B (Invitrogen, San Diego, Calif.). The sequence of the secretion signal and multiple cloning site is (SEQ ID NO:42 and SEQ ID NO:43):

```
met lys phe leu val asn val ala leu val phe met val tyr
atg aaa ttc tta gtc aac gtt gcc ctt ttt atg gtc gta tac ile ser tyr ile tyr ala asp pro ser ser ser ala
att tct tac atc tat gcg gat ccg agc tcg agt gct cta ga tct gca gct ggt acc atg gaa ttc gaa gct tgg agt cga ctc tgc tga
```

Assembly of C2

In one example, de novo synthesis of a TM gene (including the TM core) may be initiated by assembly of a partial gene, called C2, encoding amino acids 19–66 of the TM. The sequence of C2 DNA and the peptide sequence encoded by the C2 DNA are shown in Table IV and SEQ ID NO:9. C2 is generated by annealing oligonucleotides 3, 4, 5, 6, 7 and 8 of Table III (SEQ ID NOs:54–56, 58, 60, 61) into a DNA fragment encoding approximately 48 amino acids of the TM Core polypeptide. Oligonucleotide pairs 3&4, 5&6, and 7&8 are first annealed pairwise into overlapping DNA duplexes, and the 3 double stranded DNAs are then annealed together to form a double stranded DNA complex composed of the 6 individual oligonucleotides. Oligonucleotides 1 and 8 have overhanging unpaired ends compatible with the unpaired ends of DNA restricted with the enzymes Xba I and Bgl II, respectively. C2 is annealed into the vector pMelBac XP, at the Xba I and Bgl II restriction endonuclease sites of the multiple cloning region and the DNA fragments enzymatically ligated to form the vector pTMC ( Method 1).

Method 1

Synthesis of C2 DNA from Oligonucleotides and Insertion into pMelBac XP to Form pTMC Individual oligonucleotides 3, 4, 5, 6, 7, and 8 (SEQ ID NOs:54–56, 58, 60, 61) are separately dissolved in TE buffer (Sambrook et al., *Molecular Cloning: A Laboratory Manual*, 2d ed., Cold Spring Harbor Laboratory, Cold Spring Harbor, N.Y., 1989) at a concentration of 1 mM (1 nanomole/microliter). Two nanomoles of each oligonucleotide are combined with the same amount of its pair (e.g., (3&4), (5&6) or (7&8)) in 10 μL of annealing buffer (10 mM Tris pH 8.0, 100 mM NaCl, 1 mM EDTA) in a microcentrifuge tube, and the tubes immersed in 50 mL boiling water for 5 minutes. The entire boiling water bath, including microcentrifuge tubes, is then removed from the heat source and allowed to cool to room temperature (approximately 24° C.), The mixture of vector DNA and synthetic gene fragment is then heated to 35° C. for 15 minutes, then 1/10 volume of Ligation Stock Buffer is added, DNA ligase is added and the reaction mixture incubated at 12° C. for 12 hours to ligate the phosphodiester bonds among oligonucleotides and vector DNA, as described in Sambrook et al., *Molecular Cloning. A Laboratory Manual*, 2d ed., Cold Spring Harbor Laboratory, Cold Spring Harbor, N.Y., 1989. DNA is then used for transfection of competent *E. coli* cells by standard methods (see Sambrook et al., supra). Plasmid DNA is isolated from these cells and is evaluated by restriction endonuclease digestion or DNA sequencing to evaluate the success of synthetic DNA assembly and cloning. The resulting plasmid, pTMC is then used as a framework for successive addition of synthetic TM sequences.

Assembly of D1.1 and Insertion into the TM Synthetic Gene

A fragment of the TM DNA proximal to C2, called D1.1, encodes amino acids 9 to 20 of the TM. The DNA sequence and primary amino acid peptide sequence of D1.1 are shown in Table V, SEQ ID NO:10 and SEQ ID NO:20. D1.1 encodes the proximal amino acids of the TM Core polypeptide (residues 12 to 20) as well as a short peptide of three amino acids which serve to join the TM Core with a leader peptide (appropriate for the expression system employed for synthesis of TM). D1.1 is generated by annealing oligonucleotides 1.1 (SEQ ID NO:48) and 2.1 (SEQ ID NO:51) into a DNA duplex as described in Method 1. Oligonucleotides 1.1 and 2.1 have overhanging unpaired ends compatible with the unpaired ends of BamHI (or Bgl II) and Xba I, respectively. D1.1 is annealed into pTMC at the BamHI and Xba I restriction endonuclease sites of the multiple cloning region and the DNA fragments enzymatically ligated, in a manner similar to that described in Method 1 for pTMC, to form the vector pTMD1.1C.

Assembly of L3Δ and insertion into the TM Synthetic Gene

A fragment of the TM DNA distal to C2, called L3Δ, encodes a contiguous polypeptide of amino acids 66–70 and 92–101 of the TM provided in Table II. The DNA sequence and peptide sequence of L3 are shown in Table VI, SEQ ID NO:11 and SEQ ID NO:21. L3Δ is generated by annealing oligonucleotides 9L3Δ and 10L3Δ into a DNA duplex as described in Method 1 to generate the distal portion of the TM Core DNA encoding approximately 14 amino acids. Oligonucleotides 9L3Δ and 10L3Δ have overhanging unpaired ends compatible with the unpaired ends of Bgl II and EcoRI, respectively. L3Δ is ligated into the vector pTMD1.1C at the Bgl II and EcoRI restriction endonuclease sites and the DNA fragments enzymatically ligated, in a manner similar to that described in Method 1 for pTMC, to form the vector pTMCore.

A TM may also be synthesized as described above, except that L3 (discussed below) is used in place of L3Δ. The sequence of such a TM is provided in Table IX and SEQ ID NO:13.

Assembly of a Synthetic Gene Encoding a Full Length TM Polypeptide

A full length TM gene sequence may be defined by the combination of D1, C2, L3 and T4. One example of a full length TM gene (SEQ ID NO:7) is generated from the oligonucleotides 1, 2, 3, 4, 5, 6, 7, 8, 9, 10, 11, 12, 13, 14, 15, and 16 listed in Table III (SEQ ID NOs:46, 47, 54–56, 58, 60–62 and 73–79). A gene containing D1, C2, L3, and T4 or coding sequences that differ only in conservative substitutions or modifications is a full length TM gene.

Assembly of D1 and Insertion into the TM Synthetic Gene

A fragment of the TM DNA proximal to C2, called D1, encodes amino acids −2 to 20 of the TM. The DNA sequence and peptide sequence of D1 are shown in Table V.A, SEQ ID NO:15 and SEQ ID NO:25. D1 encodes the proximal amino acids of the TM Core polypeptide (residues 12 to 20) as well as a peptide of 13 amino acids which serves to join the TM Core with a leader peptide (appropriate for the expression system employed for synthesis of TM). D1 is generated by annealing oligonucleotides 1 and 2 (Table III; SEQ ID NO:46 and SEQ ID NO:47, respectively). Oligonucleotides 1 and 2 have overhanging unpaired ends compatible with the unpaired ends of BamHI (or Bgl II) and Xba I, respectively. D1 is annealed into pTMC at the BamHI and Xba I restriction endonuclease sites of the multiple cloning region and the DNA fragments enzymatically ligated, in a manner similar to that described in Method 1 for pTMC, to form the vector pTMDC.

Assembly of L3 and Insertion into the TM Synthetic Gene

A fragment of the TM DNA distal to C2, called L3, encodes amino acids 66–101 of TM. The DNA sequence and peptide sequence of L3 are shown in Table VI.A, SEQ ID NO:15 and SEQ ID NO:25. L3 is generated by annealing oligonucleotides 9, 10, 11, and 12 (Table III; SEQ ID NOs:62, 73–75) into a DNA duplex to generate the distal portion of the TM Core DNA encoding approximately 35 amino acids. Oligonucleotide pairs 9&10 and 11&12 are first annealed together to form a double stranded DNA complex composed of the 4 individual oligonucleotides. Oligonucleotides 9 and 12 have overhanging unpaired ends compatible with the unpaired ends of Bgl II and Pst I, respectively. L3 is annealed into the vector pTMDC at the Bgl II and PstI restriction endonuclease sites and the DNA fragments enzymatically ligated, in a manner similar to that described in Method 1 for pTMC, to form the vector pTMDCL.

Assembly of T4 and Insertion into the TM Synthetic Gene

A fragment of the TM DNA distal to L3, called T4, encodes amino acids 102–141 of the TM. The DNA sequence and peptide sequence of L4 are shown in Table VII, SEQ ID NO: 12 and SEQ ID NO:22. L3 is generated by annealing oligonucleotides 13, 14, 15, and 16 (Table III; SEQ ID NOs:76–79) into a DNA fragment which is the distal portion of the full length TM DNA encoding approximately 36 amino acids. Oligonucleotide pairs 13&14 and 15&16 are first annealed pairwise into overlapping DNA duplexes, and the two double stranded DNAs are subsequently annealed together to form a double stranded DNA complex composed of the 4 individual oligonucleotides. Oligonucleotides 13 and 16 have overhanging unpaired ends compatible with the unpaired ends of Pst I and EcoRI, respectively. T4 is annealed into the vector pTMDCL at the Pst I and Eco RI restriction endonuclease sites and the DNA fragments enzymatically ligated, in a manner similar to that described in Method 1 for pTMC, to form the vector pTM.

Assembly of Synthetic Genes Encoding Modified TM Polypeptides

Other versions of TM genes, in which the peptide sequence is altered from the full length TM or TM Core, can be synthesized by using alternative oligonucleotides to 1, 2, 3, 4, 5, 6, 7, 8, 9, 10, 11, 12, 13, 14, 15, or 16 listed in Table III (SEQ ID NOs:46, 47, 54–56, 58, 60–62, 73–79). These alternative oligonucleotides can be employed during synthesis of a partial TM gene, or can be used to generate DNA fragments which can replace coding sequences in an assembled TM gene or TM gene fragment by removing DNA fragments with restriction endonucleases, and replacing the original sequence with an alternative coding sequence. In addition, DNA sequences encoding polypeptides unrelated to TM can be inserted into the TM coding sequences at various positions.

Assembly of a Synthetic Gene Encoding an Aglycosylated TM Polypeptide

In one example oligonucleotides 5 and 6 are replaced during the assembly of C2 with oligonucleotides 5.1dg (SEQ ID NO:57) and 6.1dg (SEQ ID NO:59), shown in Table III, to form a new fragment called C2Δglyco. This oligonucleotide substitution results in an altered C2 DNA sequence so that the asparagine encoded at residue 48 is changed to a histidine. With the exception of the oligonucleotides 5.1 dg and 6.1dg, C2Δglyco is created in the same manner as C2. C2Δglyco can be used in the synthesis of a variety TM sequences in a manner similar to that described for TM Core and full length TM sequences.

Assembly of a Synthetic Gene Encoding a TM Polypeptide with a Modified L3 Domain In another example, TM amino acid residues 71–91 are replaced with the three amino acid peptide: ser-asp-ile. In this example oligonucleotides 9.2Δ3 (SEQ ID NO:67) and 10.2Δ3 (SEQ ID NO:68), shown in Table III, are first annealed into a DNA duplex and subsequently annealed into the vector pTMDC at the Bgl II and Eco RI restriction endonuclease sites. The annealed DNA fragments are then enzymatically ligated to form the vector pTMLΔ3.

Assembly of Synthetic Genes Encoding a TM Polypeptide with Cysteine Residue 68 Replaced In other examples, the oligonucleotide pairs 9.3Δ3ser&10.3Δ3ser (SEQ ID NO:69 and SEQ ID NO:70) or 9.3Δ3val&10.3Δ3val (SEQ ID NO:71 and SEQ ID NO:72) are annealed into DNA duplexes and digested with the enzyme ClaI and subsequently annealed into pTMLΔ3 which has been digested with restriction enzymes ClaI and PstI. These two oligonucleotide pairs, when inserted into pTM1Δ3, result in a TMΔ3 molecule with the cysteine at position 68 replaced by serine or valine, respectively.

Assembly of Synthetic Genes Encoding a TM Polypeptide with Cysteine Residue 14 Replaced In another example the oligonucleotide pairs 1.2ser&2.2ser (SEQ ID NO:50 and SEQ ID NO:51) or 1.2val&2.2val (SEQ ID NO:52 and SEQ ID NO:53) can be annealed to generate an alternative domain to D1 with the cysteine residue 14 replaced with serine or valine, respectively. These oligonucleotide pairs are then annealed, in the same manner as described above for D1, into pTMC at the BamHI and Xba I restriction endonuclease sites of the multiple cloning region and the DNA fragments enzymatically ligated to form alternatives to the vector pTMD1C.

Assembly of a Synthetic Gene Encoding a TM Core Polypeptide Containing an Endomembrane Retention Signal In a further example TM core is synthesized with the endomembrane retention signal KDEL (SEQ ID NO:44) as the carboxyterminal amino acid residues. In this example oligonucleotides 9L3ΔKDEL (SEQ ID NO:65) and 10L3ΔKDEL (SEQ ID NO:66) are substituted for oligonucleotides 9L3Δ and 10L3Δ during synthesis of TM core described above to form the vector pTMLΔ3KDEL.

Assembly of a Synthetic gene encoding a Full Length TM Polypeptide Containing an Endomembrane Retention Signal In another example TM is synthesized with the endomembrane retention signal KDEL (SEQ ID NO:44) as the carboxyterminal amino acid residues. In this example oligonucleotides 15KDEL (SEQ ID NO:80) and 16KDEL (SEQ ID NO:81) are substituted for oligonucleotides 15 and 16 as described above for synthesis of T4. The substitution of these two oligonucleotides results in the formation of coding sequence T4KDEL which when substituted for T4 in the above described synthesis of pTM results in the formation of the vector pTMKDEL.

Assembly of a Synthetic Gene Encoding a TM Polypeptide Containing an Additional Amino Terminal Sequence In one example a TM gene is synthesized with the polyimmunoglobulin receptor sequence from residues 585–600 (AIQDPRLFAEEKAVAD; SEQ ID NO:45) included as part of the amino terminal domain. The oligonucleotides P1 (SEQ ID NO:82) and P2 (SEQ ID NO:83) encode this polyimmunoglobulin receptor sequence and amino acid residues of D1. P1 and P2 have overhanging unpaired ends compatible with the unpaired ends of Bam HI and XbaI, respectively. The oligonucleotides P1 and P2 are annealed into a DNA duplex which can be used in place of D1.1 or D1 in the synthesis of a TM expression vectors as described above.

Assembly of a Synthetic Gene Encoding a TM Polypeptide in which a Component of TM is Replaced by Another Peptide Domain TpS2

In this Example, a TM gene is synthesized with a peptide replacing TM Domains 4, 5 and 6. This peptide, referred to as TpS2, encodes an enterokinase cleavable peptide between the terminal residue of Domain 2 and the coding sequence for the trefoil peptide pS2 (as reported in Suemori et al., *Proc. Natl. Acad. Sci.* 88:11017–11021, 1991). The DNA sequence and peptide sequence of TpS2 are shown in Table X. TpS2 is generated by annealing oligonucleotides Tp1, Tp2, Tp3, Tp4, Tp5 and Tp6 (Table III; SEQ ID NOs:87–92) into a DNA fragment which encodes approximately 64 amino acids. Oligonucleotide pairs Tp1 & Tp2, Tp3 & Tp4 and Tp5 & Tp6 are first annealed pairwise into overlapping DNA duplexes, and the two double stranded DNAs are subsequently annealed together to form a double stranded DNA complex composed of the 6 individual oligonucleotides. Oligonucleotides Tp1 and Tp6 have overhanging unpaired ends compatible with the unpaired ends of PstI and EcoRI restriction sites, respectively. TpS2 is annealed into the vector pTMDCL at the PstI and EcoRI restriction endonuclease sites and the DNA fragments enzymatically ligated, in a manner similar to that described in Method 1 for pTMC, to form a vector pTMpSp2, which encodes a TM with the trefoil peptide pS2 included as a replacement for TM Domains 4, 5 and 6.

D. Isolation and Expression of cDNA Encoding Human J Chain

Two human small intestine cDNA libraries (Clontech Laboratories, Palo Alto Calif.; cat #HL1133a and dHL1133b) are screened using a synthetic DNA complementary to the 5' end of the human J chain messenger RNA. The probes are labeled with [$^{32}$P] using polynucleotide kinase in standard reactions. The library screening is performed as described by the manufacturer (Clontech). Hybridization is carried out according to Church and Gilbert, *Proc. Natl. Acad. Sci. USA* 81:1991–1995, 1984. After autoradiography, positive plaques are isolated and the phage are disrupted by boiling for 10 minutes. The DNA inserts are amplified by PCR in a total volume of 50 μL containing standard PCR buffer, 25 pmoles of primers complementary to the 5' and 3' ends of the human J chain cDNA, 200 μM of each dNTP, and 1.0 unit of Taq polymerase. The DNA is denatured for 3 minutes at 94° C. prior to 35 cycles of amplification. Each cycle consisted of 1 min at 94° C., 1 min at 62° C., and 1 min at 72° C. The PCR fragments are cloned into pUC19 and sequenced. Full length cDNA inserts are then subcloned into the appropriate insect expression vector (pMelBacXP) utilizing restriction sites placed in the two PCR primers.

TABLE II

DNA Sequence and Primary Amino Acid Structure of a Representative Full Length TM Molecule

| | | | | | | | | | | | | | | | | | |
|---|---|---|---|---|---|---|---|---|---|---|---|---|---|---|---|---|---|
| −2 | −1 | 1 | 2 | 3 | 4 | 5 | 6 | 7 | 8 | 9 | 10 | 11 | 12 | 13 | 14 | 15 | 16 |
| *asp* | *gln* | *glu* | *asp* | *glu* | *arg* | *ile* | *val* | *leu* | *val* | *asp* | *asn* | *lys* | *cys* | *lys* | *cys* | *ala* | *arg* |
| gat | cag | gaa | gat | gaa | cgt | att | gtt | ctg | gtt | gac | aac | aag | tgc | aag | tgt | gct | cgt |
| cta | gtc | ctt | cta | ctt | gca | taa | caa | gac | caa | ctg | ttg | ttc | acg | ttc | aca | cga | gca |
| 17 | 18 | 19 | 20 | 21 | 22 | 23 | 24 | 25 | 26 | 27 | 28 | 29 | 30 | 31 | 32 | 33 | 34 |
| *ile* | *thr* | *ser* | *arg* | *ile* | *ile* | *arg* | *ser* | *ser* | *glu* | *asp* | *pro* | *asn* | *glu* | *asp* | *ile* | *val* | *glu* |
| att | act | tct | aga | atc | atc | cgt | agc | tca | gag | gac | cca | aat | gaa | gat | ata | gtc | gaa |
| taa | tga | aga | tct | tag | tag | gca | tcg | agt | ctc | ctg | ggt | tta | ctt | cta | tat | cag | ctt |
| 35 | 36 | 37 | 38 | 39 | 40 | 41 | 42 | 43 | 44 | 45 | 46 | 47 | 48 | 49 | 50 | 51 | 52 |
| *arg* | *asn* | *ile* | *arg* | *ile* | *ile* | *val* | *pro* | *leu* | *asn* | *asn* | *arg* | *glu* | *asn* | *ile* | *ser* | *asp* | *pro* |
| cgt | aac | atc | cgt | atc | atc | gtc | cca | ctg | aat | aac | cgg | gag | aat | atc | tca | gat | cct |
| gca | ttg | tag | gca | tag | tag | cag | ggt | gac | tta | ttg | gcc | ctc | tta | tag | agt | cta | gga |

TABLE II-continued

DNA Sequence and Primary Amino Acid Structure of a Representative Full Length TM Molecule

```
 53   54   55   56   57   58   59   60   61   62   63   64   65   66   67   68   69   70
thr  ser  pro  leu  arg  thr  arg  phe  val  tyr  his  leu  ser  asp  leu  cys  lys  lys
aca  agt  ccg  ttg  cgc  aca  cgc  ttc  gta  tac  cac  ctg  tca  gat  ctg  tgt  aag  aag
tgt  tca  ggc  aac  gcg  tgt  gcg  aag  cat  atg  gtg  gac  agt  cta  gac  aca  ttc  ttc 71   72   73   74   75   76   77   78   79   80   81   82   83   84   85   86   87   88
cys  asp  pro  thr  glu  val  glu  leu  asp  asn  gln  ile  val  thr  ala  thr  gln  ser
tgt  gat  cca  aca  gag  gta  gag  ctg  gac  aat  cag  ata  gtc  act  gcg  act  caa  agc
aca  cta  ggt  tgt  ctc  cat  ctc  gac  ctg  tta  gtc  tat  cag  tga  cgc  tga  gtt  tcg 89   90   91   92   93   94   95   96   97   99  100  101  102  103  104  109  110  111
asn  ile  cys  asp  glu  asp  ser  ala  thr  glu  thr  cys  ser  thr  tyr  asp  arg  asn
aac  att  tgc  gat  gag  gac  agc  gct  aca  gaa  acc  tgc  agc  acc  tac  gat  agg  aac
ttg  taa  acg  cta  ctc  ctg  tcg  cga  tgt  ctt  tgg  acg  tcg  tgg  atg  cta  tcc  ttg 112  113  114  115  116  117  118  119  120  121  122  123  124  125  126  127  128  129
lys  cys  tyr  thr  ala  val  val  pro  leu  val  tyr  gly  gly  glu  thr  lys  met  val
aaa  tgc  tac  acg  gcc  gtg  gtt  ccg  ctc  gtg  tat  ggt  gga  gag  aca  aaa  atg  gtg
ttt  acg  atg  tgc  cgg  cac  caa  ggc  gag  cac  ata  cca  cct  ctc  tgt  ttt  tac  cac 130  131  132  133  134  135  136  137  138  139  140  141
glu  thr  ala  leu  thr  pro  asp  ala  cys  tyr  pro  asp  OPA
gaa  act  gcc  ctt  acg  ccc  gat  gca  tgc  tat  ccg  gac  tga  attc
ctt  tga  cgg  gaa  tgc  ggg  cta  cgt  acg  ata  ggc  ctg  act  taag
```

TABLE III

Oligonucleotides for Construction of Representative Partial TM Genes

| OLIGO | SEQUENCE |
|---|---|
| 1: | gat cag gaa gat gaa cgt att gtt ctg gtt gac aac aag tgc aag tgt gct cgt att act t |
| 2: | cta gaa gta ata cga gca cac ttg cac ttg ttg tca acc aga aca ata cgt tca tct tcc t |
| 1.1: | gat cag aag tgc aag tgt gct cgt att act t |
| 2.1: | ct aga agt aat acg agc aca ctt gca ctt ct |
| 1.2ser: | gat cag gaa gat gaa cgt att gtt ctg gtt gac aac aag tgc aag tcc gct cgt att act t |
| 2.2ser: | cta gaa gta ata cga gcg gac ttg cac ttg ttg tca acc aga aca ata cgt tca tct tcc t |
| 1.2val: | gat cag gaa gat gaa cgt att gtt ctg gtt gac aac aag tgc aag gtt gct cgt att act t |
| 2.2val: | cta gaa gta ata cga gca acc ttg cac ttg ttg tca acc aga aca ata cgt tca tct tcc t |
| 3: | cta gaa tca tcc gta gct cag agg acc caa atg aag ata tag tcg aa |
| 4 | gat acg gat gtt acg ttc gac tat atc ttc att tgg gtc ctc tga gct acg gat gat t |
| 5: | cgt aac atc cgt atc atc gtc cca ctg aat aac cgg gag aat atc tca g |
| 5.1dg: | cgt aac atc cgt atc atc gtc cca ctg aat aac cgg gag cac atc tca g |
| 6: | acg gac ttg tag gat ctg aga tat tct ccc ggt tat tca gtg gga cga t |
| 6.1dg: | acg gac ttg tag gat ctg aga tgt gct ccc ggt tat tca gtg gga cga t |
| 7: | atc cta caa gtc cgt tgc gca cac gct tcg tat acc acc tgt ca |
| 8: | gat ctg aca ggt ggt ata cga agc gtg tgc gca |
| 9: | gat ctg tgt aag aag tgt gat cca aca gag gta gag ctg gac aat cag ata gtc act gca |
| 9L3Δ: | gat ctg tgt aag aag gat gag gac agc gct aca gaa acc tgc tg |
| 10L3Δ: | aat tca gca ggt ttc tgt agc gct gtc ctc atc ctt ctt aca ca |
| 9L3ΔKDEL: | gat ctg tgt aag aag gat gag gac agc gct aca gaa acc tgc tac gag aag gat gag ctg tg |
| 10L3ΔKDEL: | aat tca cag ctc atc ctt cgc gtc gca ggt ttc tgt agc gct gtc ctc atc ctt ctt aca ca |
| 9.2Δ3: | gat ctg tgt aag aag tct gat atc gat gaa gat tcc gct aca gaa acc tgc agc aca tg |
| 10.2Δ3: | aat tca tgt gct gca ggt ttc tgt agc gga atc ttc atc gat atc aga ctt ctt aca ca |
| 9.3Δ3/ser68: | gat ctg tct aag aag tct gat atc gat gaa gat tac aga ttc ttc aga cta tag cta ctt cta a |
| 10.3Δ3/ser68: | aat ctt cat cga tat cag act tct tag aca |
| 9.3Δ3/val68: | gat ctg gtt aag aag tct gat atc gat gaa gat tac caa ttc ttc aga cta tag cta ctt cta a |
| 10.3Δ3/val68: | aat ctt cat cga tat cag act tct taa cca |
| 10: | att gtc cag ctc tac ctc tgt tgg atc aca ctt ctt aca ca |

TABLE III-continued

Oligonucleotides for Construction of Representative Partial TM Genes

| OLIGO | SEQUENCE |
|---|---|
| 11: | act caa agc aac att tgc gat gag gac agc gct aca gaa acc tgc a |
| 12: | ggt ttc tgt agc gct ctg ctc atc gca aat gtt gct ttg agt cgc agt gac tat ctg |
| 13: | gc acc tac gat agg aac aaa tgc tac acg gcc gtg gtt ccg ctc gtg tat ggt gga gag |
| 14: | gag cgg aac cac ggc cgt gta gca ttt gtt cct atc gta ggt gct gca |
| 15: | aca aaa atg gtg gaa act gcc ctt acg ccc gat gca tgc tat ccg gac tg |
| 16: | aat tca gtc cgg ata gca tgc atc ggg cgt aag ggc agt ttc cac cat ttt tgt ctc tcc acc ata cac |
| 15KDEL: | aca aaa atg gtg gaa act gcc ctt acg ccc gat gca tgc tat ccg gac aag gat gaa ttg tg |
| 16KDEL: | aat tca caa ttc atc ctt gtc cgg ata gca tgc atc ggg cgt aag ggc agt ttc cac cat ttt tgt ctc tcc acc ata cac |
| P1: | gat cag gtc gct gcc atc caa gac ccg agg ctg ttc gcc gaa gag aag gcc gtc gct gac tcc aag tgc aag tgt gct cgt att act t |
| P2: | ct aga agt aat acg agc aca ctt gca ctt gga gtc agc gac ggc ctt ctc ttc ggc gaa cag cct cgg gtc ttg gat ggc agc gac ct |
| Tp1: | gc gat gac gac gat aag gcc caa acg gag acc tgt act gtt gcg cct cgt gaa cgg caa aac tgc gga ttc ccg gaa |
| Tp2: | gtt ttg ccg ttc acg agg cgc aac agt aca ggt ctc cgt ttg ggc ctt atc gtc gtc atc gct tca |
| Tp3: | gta aca ccc tct cag tgc gct aat aaa ggc tgc tgt ttt gat gac acg gta cgg ggc gtt ccg tgg tgc ttc |
| Tp4: | gcc ccg tac cgt gtc atc aaa aca gca gcc ttt att agc gca ctg aga ggg tgt tac ttc cgg aac tcc gca |
| Tp5: | tac ccc aat aca att gac gtt ccg cct gaa gaa gag tgc gag ccg taa g |
| Tp6: | aattc tta cgg ctc gca ctc ttc ttc agg cgg caa gtc aat gtt att ggg gta gaa gca cca cgg aac |

TABLE IV

Peptide and cDNA sequence of Domain C2 of TM (TM aa residues 19–65)

```
 19  20  21  22  23  24  25  26  27  28  29  30  31  32  33  34  35  36
ser arg ile ser ile arg ser ser glu asp pro asn glu asp ile val glu arg asn
>>>>>>>>>>>>>>>>>>> oligo #3 >>>>>>>>>>>>>>>>>>>>>>>>>>>>>/>>>>>>>
  ct aga atc atc cgt agc tca gag gac cca aat gaa gat ata gtc gaa cgt aac
      t tag tag gca tcg agt ctc ctg ggt tta ctt cta tat cag ctt gca ttg
         <<<<<<<<<<<<<<<<<<< oligo #4 <<<<<<<<<<<<<<<<<<<<<<<<<<<<

37  38  39  40  41  42  43  44  45  46  47  48  49  50  51  52  53  54
ile arg ile ile val pro leu asn asn arg glu asn ile ser asp pro thr ser
>>>>>>>>>>>>>>>>>> oligo #5 >>>>>>>>>>>>>>>>>>>>>>>>/>>>>>>>>>>>>>>>
atc cgt atc atc gtc cca ctg aat aac cgg gag aat atc tca gat cct aca agt
tag gca tag tag cag ggt gac tta ttg gcc ctc tta tag agt cta gga tgt tca
<<<<<<< oligo #6 <<<<<<<<<<<<<<<<<<<<<<<<<<<<<<<<<<<<<<<<<<<<<

55  56  57  58  59  60  61  62  63  64  65  66        amino acid number
pro leu arg thr arg phe val tyr his leu ser asp leu   amino acid
>>>>>>>>>> oligo #7 >>>>>>>>>>>>>>>>>>>>>>>           coding strand oligo
ccg ttg cgc aca cgc ttc gta tac cac ctg tca           coding strand
ggc aac gcg tgt gcg aag cat atg gtg gac agt cta g     noncoding strand
<<<</<<<<< oligo #8 <<<<<<<<<<<<<<<<<<<<<<<<<         noncoding strand
                                                      oligo
```

TABLE V

DNA sequence and primary amino acid structure of
Domain D1.1 of TM (TM aa residues 9-20)

```
 9   10  11  12  13  14  15  16  17  18  19  20
asp gln lys cys lys cys ala arg ile thr ser arg
>>>>>>>>>>>> oligo D1.1>>>>>>>>>>>>>>>>>>
gat cag aag tgc aag tgt gct cgt att act t
    tc  ttc acg ttc aca cga gca taa tga aga tc
    <<<<<<<<<<<<<< oligo D2.1<<<<<<<<<<<<<<
```

TABLE V.A

DNA sequence and primary amino acid structure of Domain D1 of TM
(TM aa residues -2–20)

```
 -2  -1   1   2   3   4   5   6   7   8   9  10  11  12  13  14  15
asp gln glu asp glu arg ile val leu val asp asn lys cys lys cys ala
gat cag gaa gat gaa cgt att gtt ctg gtt gac aac aag tgc aag tgt gct
    tc  ctt cta ctt gca taa caa gac caa ctg ttg ttc acg ttc aca cga 16  17  18  19  20
arg ile thr ser arg
cgt att act t
gca taa tga aga tc
```

TABLE VI

Peptide and DNA sequence of Domain L3Δ of TM
(TM aa residues 66-70 and 92-101)

```
 66  67  68  69  70  92  93  94  95  96  97  99 100 101
asp leu cys lys lys asp glu asp ser ala thr glu thr cys OPA
gat ctg tgt aag aag gat gaa gat tcc gct aca gaa acc tgc tg
    ac  aca ttc ttc cta ctt ctc agg cga tgt ctt tgg acg act taa
```

TABLE VI.A

Peptide and DNA sequence of Domain L3 of TM
(TM aa residues 66-101)

```
66  67  68  69  70  71  72  73  74  75  76  77  78  79  80  81
asp leu cys lys lys cys asp pro thr glu val glu leu asp asn gln
gat ctg tgt aag aag tgt gat cca aca gag gta gag ctg gac aat cag
cta gac aca ttc ttc aca cta ggt tgt ctc cat ctc gac ctg tta gtc 82  83  84  85  86  87  88  89  90  91  92  93  94  95  96  97
ile val thr ala thr gln ser asn ile cys asp glu asp ser ala thr
ata gtc act gcg act caa agc aac att tgc gat gag gac agc gct aca
tat cag tga cgc tga gtt tcg ttg taa acg cta ctc ctg tcg cga tgt 100
glu thr cys
gaa acc tgc
ctt tgg acg
```

TABLE VII

Peptide and cDNA sequence of Domain L4 of TM
DNA and Primary Amino Acid Sequence of T4 Fragment
(TM aa residues 102-141)

```
  102 103 104 109 110 111 112 113 114 115 116 117 118 119 120 121
  ser thr tyr asp arg asn lys cys tyr thr ala val val pro leu val
   gc acc tac gat agg aac aaa tgc tac acg gcc gtg gtt ccg ctc gtg
  acg tcg tgg atg cta tcc ttg ttt acg atg tgc cgg cac caa ggc gag cac
```

TABLE VII-continued

Peptide and cDNA sequence of Domain L4 of TM
DNA and Primary Amino Acid Sequence of T4 Fragment
(TM aa residues 102–141)

```
122 123 124 125 126 127 128 129 130 131 132 133 134 135 136 137 138
tyr gly gly glu thr lys met val glu thr ala leu thr pro asp ala cys
tat ggt gga gag aca aaa atg gtg gaa act gcc ctt acg ccc gat gca tgc
ata cca cct ctc tgt ttt tac cac ctt tga cgg gaa tgc ggg cta cgt acg 139 140 141
tyr pro asp OPA
tac cct gac tg
atg gga ctg act taa
```

TABLE VIII

DNA Sequence and Primary Amino Acid Sequence of a Representative
TM Core Element

```
 9   10  11  12  13  14  15  16  17  18  19
asp gln lys cys lys cys ala arg ile thr ser
gat cag aag tgc aag tgt gct cgt att act tct
cta gtc ttc acg ttc aca cga gca taa tga aga 20  21  22  23  24  25  26  27  28  29  30  31  32  33  34  35  36
arg ile ile arg ser ser glu asp pro asn glu asp ile val glu arg asn
aga atc atc cgt agc tca gag gac cca aat gaa gat ata gtc gaa cgt aac
tct tag tag gca tcg agt ctc ctg ggt tta ctt cta tat cag ctt gca ttg 37  38  39  40  41  42  43  44  45  46  47  48  49  50  51  52  53
ile arg ile ile val pro leu asn asn arg glu asn ile ser asp pro thr
atc cgt atc atc gtc cca ctg aat aac cgg gag aat atc tca gat cct aca
tag gca tag tag cag ggt gac tta ttg gcc ctc tta tag agt cta gga tgt 54  55  56  57  58  59  60  61  62  63  64  65  66  67  68  69  70
ser pro leu arg thr arg phe val tyr his leu ser asp leu cys lys lys
agt ccg ttg cgc aca cgc ttc gta tac cac ctg tca gat ctg tgt aag aag
tca ggc aac gcg tgt gcg aag cat atg gtg gac agt cta gac aca ttc ttc 92  93  94  95  96  97  99  100 101
asp glu asp ser ala thr glu thr cys OPA Eco RI
gat gag gac agc gct aca gaa acc tgc tg
cta ctc ctg tcg cga tgt ctt tgg acg act taa
```

45

TABLE IX

DNA Sequence and Primary Amino Acid
Structure of a Representative TM

```
 9   10  11  12  13  14  15  16  17  18  19
asp gln lys cys lys cys ala arg ile thr ser
gat cag aag tgc aag tgt gct cgt att act tct
cta gtc ttc acg ttc aca cga gca taa tga aga 20  21  22  23  24  25  26  27  28  29  30  31  32  33  34  35  36
arg ile ile arg ser ser glu asp pro asn glu asp ile val glu arg asn
aga atc atc cgt agc tca gag gac cca aat gaa gat ata gtc gaa cgt aac
tct tag tag gca tcg agt ctc ctg ggt tta ctt cta tat cag ctt gca ttg 37  38  39  40  41  42  43  44  45  46  47  48  49  50  51  52  53
ile arg ile ile val pro leu asn asn arg glu asn ile ser asp pro thr
atc cgt atc atc gtc cca ctg aat aac cgg gag aat atc tca gat cct aca
tag gca tag tag cag ggt gac tta ttg gcc ctc tta tag agt cta gga tgt
```

TABLE IX-continued

DNA Sequence and Primary Amino Acid Structure of a Representative TM

| 54  | 55  | 56  | 57  | 58  | 59  | 60  | 61  | 62  | 63  | 64  | 65  | 66  | 67  | 68  | 69  | 70  |
|-----|-----|-----|-----|-----|-----|-----|-----|-----|-----|-----|-----|-----|-----|-----|-----|-----|
| ser | pro | leu | arg | thr | arg | phe | val | tyr | his | leu | ser | asp | leu | cys | lys | lys |
| agt | ccg | ttg | cgc | aca | cgc | ttc | gta | tac | cac | ctg | tca | gat | ctg | tgt | aag | aag |
| tca | ggc | aac | gcg | tgt | gcg | aag | cat | atg | gtg | gac | agt | cta | gac | aca | ttc | ttc |

| 71  | 72  | 73  | 74  | 75  | 76  | 77  | 78  | 79  | 80  | 81  | 82  | 83  | 84  | 85  | 86  | 87  |
|-----|-----|-----|-----|-----|-----|-----|-----|-----|-----|-----|-----|-----|-----|-----|-----|-----|
| cys | asp | pro | thr | glu | val | glu | leu | asp | asn | gln | ile | val | thr | ala | thr | gln |
| tgt | gat | cca | aca | gag | gta | gag | ctg | gac | aat | cag | ata | gtc | act | gcg | act | caa |
| aca | cta | ggt | tgt | ctc | cat | ctc | gac | ctg | tta | gtc | tat | cag | tga | cgc | tga | gtt |

| 88  | 89  | 90  | 91  | 92  | 93  | 94  | 95  | 96  | 97  | 99  | 100 | 101 | 102 |
|-----|-----|-----|-----|-----|-----|-----|-----|-----|-----|-----|-----|-----|-----|
| ser | asn | ile | cys | asp | glu | asp | ser | ala | thr | glu | thr | cys | tyr | OPA |
| agc | aac | att | tgc | gat | gag | gac | agc | gct | aca | gaa | acc | tgc | tac | tga attc |
| tcg | ttg | taa | acg | cta | ctc | ctg | tcg | cga | tgt | ctt | tgg | acg | atg | act |

TABLE X

DNA and Primary Amino Acid Sequence of TpS2

| 101 | 102 |     |     |     |     |     |     |     |     |     |     |     |     |     |
|-----|-----|-----|-----|-----|-----|-----|-----|-----|-----|-----|-----|-----|-----|-----|
| cys | ser | asp | asp | asp | asp | lys | ala | qln | thr | qlu | thr | cys | thr | val | ala | pro |
|     | gc  | gat | gac | gac | gat | aag | gcc | caa | acg | gag | acc | tgt | act | gtt | gcg | cct |
| act | tcg | cta | ctg | ctg | cta | ttc | cgg | gtt | tgc | ctc | tgg | aca | tga | caa | cgc | gga |

| arg | glu | arg | gln | asn | cys | gly | phe | pro | gly | val | thr | pro | ser | gln | cys | ala |
|-----|-----|-----|-----|-----|-----|-----|-----|-----|-----|-----|-----|-----|-----|-----|-----|-----|
| cgt | gaa | cgg | caa | aac | tgc | gga | ttc | ccg | gaa/gta | aca | ccc | tct | cag | tgc | gct |
| gca | ctt | gcc | gtt | ttg/acg | cct | aag | ggc | ctt | cat | tgt | ggg | aga | gtc | acg | cga |

| asn | lys | gly | cys | cys | phe | asp | asp | thr | val | arg | gly | val | pro | trp | cys | phe |
|-----|-----|-----|-----|-----|-----|-----|-----|-----|-----|-----|-----|-----|-----|-----|-----|-----|
| aat | aaa | ggc | tgc | tgt | ttt | gat | gac | acg | gta | cgg | ggc | gtt | ccg | tgg | tgc | ttc/ |
| tta | ttt | ccg | acg | aca | aaa | cta | ctg | tgc | cat | gcc | ccg/caa | ggc | acc | acg | aag |

| tyr | pro | asn | thr | ile | asp | val | pro | pro | glu | glu | glu | cys | glu | phe |
|-----|-----|-----|-----|-----|-----|-----|-----|-----|-----|-----|-----|-----|-----|-----|
| tac | ccc | aat | aca | att | gac | gtt | ccg | cct | gaa | gaa | gag | tgc | gag | ccg | taa g |
| atg | ggg | tta | tgt | taa | ctg | caa | ggc | gga | ctt | ctt | ctc | acg | ctc | ggc | att cttaa |

Example 2

Linkage of Imaging Agents to TM

This Example illustrates the preparation of dimeric IgA and TM linked to fluorescent and magnetic resonance imaging agents.

A. Dimeric IgA Directly Attached to Imaging Compounds

Native dimeric IgA isolated from biological sources as described above is reacted with the N-hydroxysuccinamide esters of (a) cyanine fluorochromes (Biological Detection Systems, Pittsburgh, Pa.) and (b) a manganese derivative of a sulfocyanine fluorochrome ($MnPcS_4$) prepared as described (Saini et al., *Magnetic Resonance Imaging* 13:985–990, 1995; Webber and Busch, *Inorg. Chem.* 4:469–471, 1965). The linkage reactions are performed as follows. Dimeric IgA is equilibrated with 0.1M sodium bicarbonate, and pH adjusted to 8.7 using NaOH. The dIgA solution is then added directly to dyes either dried under vacuum onto the surface of the reaction vessel or previously dissolved in water. The NHS-diesters react spontaneously with protein amino groups at neutral or basic pH. When commercially available kits (Biological Detection Systems, Pittsburgh, Pa.) are used according to the manufacturer's instructions, conjugates having 2–5 mol imaging compound per mol dIgA are obtained. To obtain higher or lower levels of conjugation, the ratio of the dye to protein is empirically adjusted to give a desired level of substitution. Typically, protein concentration is 20 mg/ml, while dye concentration varied from 1 to 10 mg/ml. Coupling is for 4 hours at room temperature or overnight at 4–6° C., with slow rotation of the mixture. Unreacted dye is blocked by addition of glycine to 0.1M and adjustment of the pH to 8.7 followed by incubation at room temperature for 1–3 hours. Dye is removed and conjugates are equilibrated in PBS by three to four cycles of centrifugation and resuspension in Centricon-30 centrifugal ultrafilters (Amicon, Beverly, Mass.). If necessary, aggregates, typically less than 5% of the total dIgA, are removed by passage over Superose 12 (Pharmacia, Piscataway, N.J.). The dye/protein ratio is estimated by taking the extinction coefficient of dIgA to be 1.5 A/mg protein/ml and assuming the extinction coefficients of the dye conjugates to be those of the free dyes. The compounds are referred to as dIgA-cyanine and dIgA-$MnPcS_4$.

The important properties of the dye s are summarized in Tables X and XI.

TABLE X

Optical Properties of Cyanine Dyes

| Dye | Absorption max. nm (PBS) | E at absorption max. | E280/Emax | Emission max., nm |
|---|---|---|---|---|
| Cy3.18 | 550 | 150,000 | 0.05 | 565 |
| Cy5.18 | 652 | 250,000 | 0.05 | 667 |
| Cy5.5.18 | 674 | 250,000 | 0.08 | 694 |

TABLE XI

Molar Relaxivities $1/T1(mMs)^{-1}$ of Paramagnetic Compounds

| Compound | Relaxation rate |
|---|---|
| MnTPPS4 | 10.39* |
| MnC12 | 9.32* |
| MriDTP A | 6.93* |
| GdC1 | 14.67* |
| GDDTP A | 5.05* |
| MnPcS4 | 10.10 |

*$1/T1$ $(mMs)^{-1}$, in water at 10.7 MHz, 37° C.

B. TM Directly Attached to Imaging Compounds

TM is synthesized by phosphoramidite coupling as described above and contains no free sulfhydryl groups. The TM is purified from transgenic insect cells using procedures described above. The amino terminal as well as accessible lysines are available for attachment of NHS-imaging compound. When the commercially available kits (Biological Detection Systems, Pittsburgh, Pa.) are used according to the manufacturer's instructions, conjugates having 0.3–0.9 mol imaging compound per mol TM are obtained. These compounds are referred to as TM-cyanine and TM-MnPcS$_4$.

C. Dimeric IgA Linked by a Epithelial Cell Specific Scissile Peptide to Imaging Compounds The polyimmunoglobulin receptor sequence from residues 585–600 (AIQDPRLFAEEKAVAD; SEQ ID NO:45), which is the substrate for an intracellular processing protease of epithelial cells, is synthesized by peptide coupling as described above. This peptide is reacted with the N-hydroxysuccinamide esters of cyanine imaging compounds (Biological Detection Systems, Pittsburgh, Pa.) as described above. The ratio of peptide to activated imaging compound is varied to optimize coupling reactions occurring at the amino terminal.

The peptide-imaging compound complex is further reacted with native dIgA purified from biological sources. The following solutions were prepared for linking peptide-imaging compound to dIgA: peptide-imaging compound stock solution—100 μg peptide-imaging compound, 0.2 mL water, 0.3 mL dimethylsulfoxide; peptide-imaging compound/NHS—100 μL peptide-imaging compound stock solution, 0.4 mg N-hydroxysulfosuccinimide, 2 mL water; EDC solution—2.46 mg 1-ethyl-3-(3-dimethylaminpropyl) carbodiimide-HCl; dIgA solution: 5 mg per mL in water. Fifty μL of peptide-imaging compound-NHS was added to 50 μL of EDC solution followed by 50 μL of dIgA solution. The reaction was allowed to proceed at room temperature for 10 minutes to 2 hours and resulted in the conjugation of the peptide imaging compound via its carboxyl terminal to free amine groups of dimeric IgA. Reaction conditions were identified which enhance the derivatization and linkage at the terminal carboxyl group rather than the internal carboxyl of aspartate. The compounds are referred to as dIgA-pIgR-cyanine.

Control preparations are performed in identical fashion except the synthetic peptide linker had no cleavage site: VAVQSAGTPASGS (SEQ ID NO:93).

D. TM Linked by an Epithelial Cell Specific Scissile Peptide to Imaging Compounds TM (extended) is synthesized by phosphoramidite coupling as described in C above and contains no free sulfhydryl groups. The TM is purified from transgenic insect cells using procedures described above. The amino terminal as well as accessible lysines are available for attachment of peptide-imaging compound.

The peptide-imaging compound complexes are prepared and further reacted with TM as described in C, above. The compounds are referred to as TM-pIgR-cyanine.

E. Dimeric IgA Linked by a Cancer Cell Specific Scissile Peptide to Imaging Compounds The procedure described in C, above, is repeated except the pro-cathepsin sequence (KAHKVDMVQYT; SEQ ID NO:39) is used instead of the pIgR processing site. In this case, the peptide-imaging compound preparation contains one, two or three imaging compounds per peptide. The compounds are referred to as dIgA-cath-cyanine.

F. TM Linked by a Cancer Cell Specific Scissile Peptide to Imaging Compounds

The same procedure as described in D is repeated except the pro-cathepsin sequence (KAHKVDMVQYT; SEQ ID NO:39) is used instead of the pIgR processing site. In this case, the peptide-imaging compound preparation contains one, two or three imaging compounds per peptide. The compound is referred to as TM-cathcyanine.

G. Fluorescent Compounds Targeted to the Endoplasmic Reticulum

Fluorescent Compound with a Scissile Linker Attachment to Synthetic TM

The polyimmunoglobulin receptor sequence from residues 585–600 (AIQDPRLFAEEKAVAD) (SEQ ID NO:45), which is the substrate for an intracellular processing protease, is synthesized by peptide coupling as described above. This peptide is reacted with Texas Red hydrazide (Pierce) in dimethylformamide according to the instructions provided by the manufacturer. The ratio of peptide to hydrazide is varied to optimize coupling reactions occurring only at the carboxyl terminal. This population of reaction products is separated from other reaction products (i.e., reactions at the internal aspartyl residue) by HPLC chromatography. The peptide-Texas Red complex is further reacted with SPDP (Pierce) according to the instructions provided by the manufacturer and is purified as above. The final reaction links the SPDP-peptide-Texas Red to the sulfhydryl groups of synthetic TM to form TM-peptide-TR. The TM structure used in these preparations is described in Table II as variation C. Control preparations are performed in identical fashion except the synthetic peptide linker has no cleavage site: VAVQSAGTPASGS (SEQ ID NO:93). The ER retention signal KDEL (SEQ ID NO:44) is synthesized as part of the TM core protein by phosphoramidite oligonucleotide coupling as described above and ligated into an insect expression vector to create pTM. The final compound is referred to as TM(kdel)-peptide-TR. Control preparations are performed in identical fashion except the synthetic peptide linker has no cleavage site: VAVQSAGTPASGS (SEQ ID NO:93).

Fluorescent Compound Targeted to the Nucleus

Two nuclear targeting sequences CAAPKKKRKV (SEQ ID NO:84) and CAAKRPAAIKKAGQAKKKK (SEQ ID NO:85) are synthesized by peptide coupling as described above. Each peptide is reacted with Texas Red hydrazide (Pierce Chemical Co.) in dimethylformamide according to the instructions provided by the manufacturer. The ratio of peptide to hydrazide is varied to optimize coupling reactions occurring only at the carboxyl terminal. This population of reaction products is separated from other reaction products by HPLC chromatography. The peptide-Texas Red complex is further reacted with MBPH (Pierce Chemical Co.) according to the instructions provided by the manufacturer and is purified as above. The final reaction links the MBPH-peptide-Texas Red to the carbohydrate groups of native TM isolated from biological sources as described above. Control preparations are performed in identical fashion except the synthetic peptide linker has no targeting function: VAVQSAGTPASGS (SEQ ID NO:93). The final compound is referred to as TM-peptide(nuc)-TR.

Example 3

Delivery of Imaging Agents

A. Delivery of Imaging Compounds to Cells In vitro

Transcytosis of Fluorescent Imaging Agents using Dimeric IgA

Confluent pIgR$^+$ MDCK cell monolayer filters are incubated at the basolateral surface for twenty-four hours with dIgA attached directly to imaging agents (digA-cyanine) prepared as described above. Cells are then detached with trypsin (0.25% in 0.02% EDTA) (JRH Biosciences, Lenexa, Kans.), cytocentrifuged onto glass slides, and fixed with acetone. Fluorescence microscopy is used to detect the presence of the imaging agent in cells. Fluorescence in the upper chamber (apical) fluid was also measured. Cells incubated with the dIgA conjugates yield fluorescence only in the apical chamber and not inside the cells indicating the quantitative transcytosis of fluorescent compounds. In contrast, the free fluorescent compounds (unconjugated) partition inside the cells but no transcytosis to the apical surface is detected.

Transcytosis of Fluorescent Imaging Agents Using TM

The experiments as described above are performed using the TM conjugates (TM-cyanine). Cells incubated with the TM conjugates also yield fluorescence only in the apical chamber and not inside the cells indicating the quantitative transcytosis of fluorescent compounds. The free fluorescent compounds (unconjugated) partition inside the cells but no transcytosis to the apical surface is detected.

Delivery to Epithelial Cells of Imaging Agents Linked to Dimeric IgA via the pIgR Peptide Confluent pIgR$^+$ MDCK cell monolayer filters are incubated at the basolateral surface for twenty-four hours with dIgA-peptide conjugates (AIQDPRLFAEEKAVAD (SEQ ID NO:45); dIgA-pIgR-cyanine) prepared as described above. Cells are then detached with trypsin (0.25% in 0.02% EDTA) (JRH Biosciences, Lenexa, Kans.), cytocentrifuged onto glass slides, and fixed with acetone. Fluorescence microscopy is used to detect the presence of imaging compounds. Fluorescence in the upper chamber (apical) fluid was also measured. Cells incubated with dIgA-peptide conjugates yield a significant level of intracellular fluorescence. Apical fluorescence (transcytosis) is also apparent using scissile peptides. In contrast, the control conjugates, containing a non-scissile peptide, had no detectable intracellular fluorescence but significant levels of transcytosed fluorescence.

Delivery to Epithelial Cells of Imaging Agents Linked to TM via the pIgR Peptide The above experiments are performed using the TM peptide conjugates (TM-pIgR-cyanine). Cells incubated with TM-peptide conjugates yield a significant level of intracellular fluorescence. Apical fluorescence (transcytosis) is also apparent using scissile peptides. In contrast, the control conjugates, containing a non-scissile peptide, had no detectable intracellular fluorescence but significant levels of transcytosed fluorescence.

Delivery of a Fluorescent Compound Targeted for Retention in the Endoplasmic Reticulum Confluent pIgR$^+$ MDCK cell monolayer filters are incubated at the basolateral surface for twenty-four hours with TM(kdel)-peptide-TR prepared as described above. Cells are then detached with trypsin (0.25% in 0.02% EDTA) (JRH Biosciences, Lenexa, Kans.), cytocentrifuged onto glass slides, and fixed with acetone. Fluorescence microscopy (580 nm excitation, 604 nm emission wavelengths) is used to detect the presence of Texas Red. Cells incubated with TM(kdel)-peptide-TR yielded a detectable level of fluorescence whereas the control construct, containing a non-scissile peptide, had no detectable fluorescence. Fluorescence is further localized to intracellular structures consistent with endomembrane organelles.

Delivery of a Fluorescent Compound to Nuclei

MDCK cells stably transfected with cDNA encoding the rabbit pIgR are cultured on nitrocellulose filters in microwell chambers (Millicell; Millipore, Bedford, Mass.). Confluent pIgR$^+$ MDCK cell monolayer filters are incubated with TM-peptide(nuc)-TR containing nuclear targeting sequences or the control TM-peptide-TR with no sequences, via the lower compartment. Twenty-four hours after the addition of TM, cells are detached with trypsin (0.25% in 0.02% EDTA) (JRH Biosciences, Lenexa, Kans.), cytocentrifuged onto glass slides, and fixed with acetone. Immunofluorescence is used to detect Texas Red.

TM-peptide(nuc)-TR localizes nuclei as documented by immunofluorescence. These observations indicate that during epithelial transcytosis, specific TM-peptide(nuc)-TR antibody can interact with cytoplasmic or endomembrane receptors and undergo transport to the nucleus. In contrast, infected monolayers treated with TM-peptide-TR containing no nuclear targeting signal do not demonstrate nuclear fluorescence localization. These studies document that MDCK cells transport specific TM-peptide(nuc)-TR containing nuclear targeting sequences to the nucleus, but do not transport TM-peptide-TR without these sequences.

Delivery to Cancer Cells of Imaging Agents Linked to Dimeric IgA via the Cathepsin Peptide Confluent pIgR$^+$ HT-29 colon carcinoma cell monolayer filters are incubated at the basolateral surface for twenty-four hours with dIgA-peptide conjugates (KAHKVDMVQYT peptide (SEQ ID NO:39); dIgA-cath-cyanine) prepared as described above. Cells are then detached with trypsin (0.25% in 0.02% EDTA) (JRH Biosciences, Lenexa, Kans.), cytocentrifuged onto glass slides, and fixed with acetone. Fluorescence microscopy is used to detect the presence of imaging compounds. Fluorescence in the upper chamber (apical) fluid was also measured. Cells incubated with dIgA-peptide conjugates yield a significant level of intracellular fluorescence. Apical fluorescence (transcytosis) is also apparent using scissile peptides. In contrast, the control conjugates, containing a non-scissile peptide, had no detectable intracellular fluorescence but significant levels of transcytosed fluorescence.

Delivery to Cancer Cells of Imaging Agents Linked to TM via the Cathepsin Peptide The same experiments are performed using the TM peptide conjugates (TM-cath-cyanine). Cells incubated with TM-peptide conjugates yield a significant level of intracellular fluorescence. Apical fluorescence (transcytosis) is also apparent using scissile peptides. In contrast, the control conjugates, containing a non-scissile peptide, had no detectable intracellular fluorescence but significant levels of transcytosed fluorescence.

B. Delivery of Imaging Compounds to Epithelial Cells In vivo

Fluorescence Imaging with Dimeric IgA Directly Attached to Cyanine Conjugates

Mice are tail-vein injected using 10–100 μg dIgA-cyanine. Immediately after injection, and typically at 12 hour intervals thereafter, mice are anesthetized using sodium pentobarbital, 65 mg/kg. Mice are imaged using one of three camera systems: a Photometrics C200 12-bit cooled CCD (Photometrics, Tucson, Ariz.), a Hamamatsu C2400 8-bit CCD with microchannel-plate enhancer, or a Hamamatsu C4480 cooled 12-bit CCD (Hamamatsu Photonics, Bridgewater, N.J.). Illumination is provided by 35-W fiber-optic illuminators (Model 190, Dolan-Jenner, Woburn, Mass.) with filters attached to the fiber output, a Storz 484C halogen illuminator equipped with a filter adapter and a 495FL light conducting cable (Karl Storz, Culver City, Calif.), or handheld diode lasers, having maximum output at 635 nm (for Cy5) or 672 nm (for Cy5.5). All illuminators performed satisfactorily, although some background emission from the exciting light is visible at high intensification or after long exposure, even when lasers are used.

Three different lens systems are used: a Nikon 50 mm f1.8 AF Nikkor for full-sized views of the animals, a Storz 27015A Hopkins Telescope to investigate endoscopic viewing, and an Olympus SZH-ILLD dissecting microscope equipped with a camera port for close-UPS. Interference filters are from Omega Optical (Brattleboro, Vt.). The filter combinations used are:

| Fluorochrome | Excitation filter | Emission filter |
|---|---|---|
| Cy3 | 535DF20 | 590DF30 |
| Cy5 | 610DF20 | 670DF40 |
| Cy5.5 | 670DF20 | 700EFLP |

Free dye is rapidly excreted in the urine, with only kidneys and bladder showing any significant fluorescence. Most of the dye is excreted within 4 hours, and there is no detectable retention at 24–48 hours. The pattern of conjugated dye retention is quite different. Immediately after injection, blood vessels were very bright and readily resolved through the skin. Liver, kidneys, spleen and bladder were next brightest, and could also be seen through the animal's skin. After 4–6 hours, while fluorescence of major organs persisted, the brightest normal organ in the animal is the gallbladder. This high concentration of fluorescence is presumably caused by uptake and catabolism of antibody by the liver, followed by deposition of the catabolites in the gallbladder. After 2 days, the brightest normal organ in the mouse is the intestine, which is particularly clear when viewed from the animal's ventral aspect. The label persists, remaining clearly detectable 5 days after injection; at the same dose and at ten-fold higher dose than the conjugate, free dye is not retained by the intestine. Microscopic examination showed that fluorescence is concentrated in the lamina propria.

Fluorescence Imaging with TM Directly Attached to Cyanine Conjugates

The procedures described above for dimeric IgA are used. Animals are tail vein injected as described above with TM-cyanine. The results are similar to those obtained using dimeric IgA. Immediately after injection, blood vessels were very bright and readily resolved through the skin. Liver, kidneys, spleen, lung and bladder were bright, and could also be seen through the animal's skin. After 2 hours, while fluorescence of major organs persisted, the brightest normal organ in the animal is the gallbladder. After 1 day, the brightest normal organ in the mouse is the intestine. Maximal distribution to normal tissue is observed at 24 hours post injection rather than at 48 hours. This result may be due to the relatively small size of the TM conjugate compared to the dIgA conjugate indicating a more rapid transendothelial tissue distribution.

Fluorescence Imaging with Dimeric IgA Attached to Cyanine Conjugates via the pIgR Peptide The procedures described above are used. Animals are tail vein injected as described above with dIgA-pIgR-cyanine. The results are similar to those obtained using dimeric IgA conjugated directly to fluorochromes. Immediately after injection, blood vessels are very bright and readily resolved through the skin. Liver, kidneys, spleen, lung and bladder are bright, and can also be seen through the animal's skin. After 4–6 hours, while fluorescence of major organs persisted, the brightest normal organ in the animal is the gallbladder. After 2 days, the brightest normal organ in the mouse is the intestine however with the pIgR peptide linker the fluorescence intensity is far less diffuse and appears to be confined to a discrete population of intestinal cells. This is indicative of fluorochrome release during transcytosis with subsequent intracellular retention of fluorochrome in epithelial cells.

Fluorescence Imaging with TM Attached to Cyanine Conjugates via the pIgR Peptide The procedures described above are used. Animals are tail vein injected as described above with TM-pIgR-cyanine. The results are similar to those obtained using TM conjugated directly to fluorochromes. Immediately after injection, blood vessels are very bright and readily resolved through the skin. Liver, kidneys, spleen, lung and bladder are bright, and can also be seen through the animal's skin. After 2–4 hours, while fluorescence of major organs persisted, the brightest normal organ in the animal is the gallbladder. After 1 day, the brightest normal organ in the mouse is the intestine however with the pIgR peptide linker the fluorescence intensity is far less diffuse and appears to be confined to a discrete population of intestinal cells. This is indicative of fluorochrome release during transcytosis with subsequent intracellular retention of fluorochrome in epithelial cells. Maximal distribution to normal tissue is observed at 24 hours post injection rather than at 48 hours. This result may be due to the relatively small size of the TM conjugate compared to the dIgA conjugate indicating a more rapid transendothelial tissue distribution.

Fluorescence Imaging with Dimeric IgA Attached to Cyanine Conjugates via the Cathepsin Peptide The human HT-29 colon carcinoma was purchased from American Type Culture Collection. Tumors are grown in nude (BALB/c background) mice; the tumor was also grown in BALB/c mice. Typically $10^6$ cells are inoculated s.c. or i.m. Tumors are selected because these are well-studied systems containing pIgR receptors, and a comparison with previous results obtained using, radioactive or therapeutic drug-antibody conjugates was possible.

Immediately after injection with dIgA-cath-cyanine (10–100 μg), blood vessels were very bright and readily resolved through the skin. Liver, kidneys, spleen and bladder were next brightest, and could also be seen through the animal's skin. After 4–6 hours, while fluorescence of major organs persisted, the brightest normal organ in the animal is the gallbladder. After 2 days, the brightest normal organ in the mouse is the intestine, which is particularly clear when viewed from the animal's ventral aspect.

Tumors are initially less fluorescent than the surrounding tissues, as expected. By 2 hours after injection, the situation is reversed. Visibility and contrast are best at 24–48 hours; tumors could be imaged through millimeter thicknesses of skin and muscle. Considerable structure could be imaged through the skin. Visibility of the tumors did not improve further after 48 hours. Small tumors are readily imaged through the skin. Non-specific conjugates labeled using the cyanine fluorochromes Cy3 or Cy5 (Biological Detection Systems, Pittsburgh, Pa.) showed no targeting to the tumors.

Cy5-dIgA conjugate is extremely persistent in tumors. One mouse was imaged for 5 days after dye injection using Cy5-dIgA and euthanized, after which its tumor was removed and frozen thin sections prepared.

To demonstrate that Cy5 conjugation by itself causes no tumor localization of dIgA, the non-specific plasmacytoma immunoglobulin MOPC-104E was conjugated to Cy5, while dIgA was conjugated to Cy5.5. The CY5.5-specific dIgA conjugate was retained by the tumor, but not the non-specific Cy5 antibody conjugate.

Fluorescence Imaging with TM Attached to Cyanine Conjugates via the Cathepsin Peptide The procedures described above are used. Immediately after injection with TM-cath-cyanine (10–100 $\mu$g), blood vessels were very bright and readily resolved through the skin. Liver, kidneys, spleen, lung and bladder were bright, and could also be seen through the animal's skin. After 2 hours, while fluorescence of major organs persisted, the brightest normal organ in the animal is the gallbladder. After 1 day, the brightest normal organ in the mouse is the intestine.

Tumors are initially less fluorescent than the surrounding tissues, as expected. By 1 hour after injection, the situation was reversed. Visibility and contrast are best at 12–24 hours; tumors could be imaged through millimeter thicknesses of skin and muscle. Considerable structure could be imaged through the skin. Visibility of the tumors did not improve further after 48 hours. Small tumors are readily imaged through the skin. Non-specific conjugates labeled using Cy3 or Cy5 showed no targeting to the tumors. Maximal distribution to tumors is observed at 24 hours post injection rather than at 48 hours. This result may be due to the relatively small size of the TM conjugate compared to the dIgA conjugate indicating a more rapid transendothelial tissue distribution.

MRI Imaging with Dimeric IgA Attached to Cyanine Conjugates via the Cathepsin Peptide C3HJax mice (4–6 weeks) are implanted with 2.6×10$^6$ tumor cells (human mammary carcinoma) subcutaneously in the region of the hind limb. A solid tumor of approximately 1 cm in diameter is apparent at the time of administration of the dye (metal complex). A calculated dose of dIgA-MnPCS4 (96 mg/kg body weight) solubilised in sterile water at pH 6.2, is injected into the lateral vein of the tail of the mice for biodistribution studies and MR imaging. For toxicity experiments, the C3H Jacks mice in a group of 10 animals each are taken, MnPCS4 dye is injected (IP) at a varying concentration of from 100 to 650 mg/kg of body weight. All the animals are put under observation for 30 days post injection.

For in vivo MR imaging, each animal is anaesthetized by subcutaneous injection of 0.1 ml (20 mg/kg) of ketamine and 0.02 ml (4 mg/kg) of diazepam sodium. The dose is repeated before each set of imaging experiments during the study. MR images are taken before and then at 1 hour and 24 hours after intravenous administration of the dye. The animal is positioned in a rat trap and placed in a thermostat enclosure during the study to avoid hypothermia in the imaging room. MR images are taken in a 1.5 Tesla superconducting clinical MRI system (MAGNETOM, Siemens, Germany) using 15 cm surface RF coil in the prone position. Continuous 4 mm slices are taken in the coronal plane with T1 weighted spin echo sequence (TE 17/TR 500 ms) with 2 averages using 256×256 matrix size. This provided an intrinsic resolution of 0.7 mm in the image plane. Care is taken to reproduce the slice position in serial studies by fixing the light localizer to coincide with predefined external markers over the animal and the surface coil. Copper nitrate solution (0.046 mol) in a glass tube placed adjacent to the animal during the imaging experiment provided a reference standard of image incalculated by drawing a region of interest (ROI) on the tumor, normal muscle in the contralateral hind limb, liver, spleen, and kidney are recorded in each set of images before and at various time intervals after administration of the dye for evaluation. Relative change in the average image intensity and image intensity normalized with the standard at various time intervals over the preinjection value provided information regarding relative concentration and transit of the injected dye.

For tumor imaging, all the animals (n=5) tolerated well the intravenous dose of 96 mg/kg. Blueish discoloration of the skin is evident immediately following intravenous administration of the dye, which clears off with time during the next 3 to 5 days. Visual difference in image intensity in the tumor, muscle, liver, and kidney between the control and treated animals at various time intervals are quantitated using the mean intensity value measured over identical regions of interest (ROI) and normalized to a corresponding value of the working standard. A significant increase in the intensity in the tumor is observed over the control value up to 48 hours post injection. Tumor-to-muscle ratio of normalized signal intensity is maximum at 48 hours compared to the control value. Maximum image intensity in the liver is found at 48 hours. Maximal image intensity at 48 hours indicates substantial uptake and retention of dIgA-MnPCS4 in the normal liver tissue. Kidneys showed the maximum value of percent increase in the signal intensity at 6 hours followed by a gradual decrease over 48 hours. Serial MR images of the mice before and after 1 and 24 hours postinjection show diffuse enhancement of the tumor in the right hind limb at 1 hour, which further increases with improved tumor-to-muscle background at 24 hours. In the case of large tumors associated with areas of necrosis, enhancement is confined to the solid areas of the tumor leaving the necrotic areas unenhanced and giving the tumor a mottled appearance. However, there is gradual filling in of the unenhanced zones with over the course of three days.

MRI Imaging with TM Attached to Cyanine Conjugates via the Cathepsin Peptide

Results substantially similar to dIgA conjugates are observed using TM conjugates (TM-MnPcS4); however maximal distribution to tumor tissue is observed at 10–20 hours post injection rather than at 48 hours. This result may be due to the relatively small size of the TM conjugate compared to the dIgA conjugate indicating a more rapid transendothelial tissue distribution.

From the foregoing, it will be appreciated that, although specific embodiments of the invention have been described herein for the purpose of illustration, various modifications may be made without deviating from the spirit and scope of the invention.

Summary of Sequence Listing

SEQ ID NO:1 is amino acid sequence of human J chain
SEQ ID NO:2 is amino acid sequence of mouse J chain
SEQ ID NO:3 is amino acid sequence of rabbit J chain
SEQ ID NO:4 is amino acid sequence of bovine J chain
SEQ ID NO:5 is amino acid sequence of bull frog J chain
SEQ ID NO:6 is amino acid sequence of earth worm J chain
SEQ ID NO:7 is nucleotide sequence of "full length" TM cDNA (Table II)
SEQ ID NO:8 is nucleotide sequence of Core TM cDNA (Table VIII)
SEQ ID NO:9 is nucleotide sequence of C2 fragment (Table IV)
SEQ ID NO:10 is nucleotide sequence of D1.1 fragment (Table V)
SEQ ID NO:11 is nucleotide sequence of L3D fragment (Table VI)
SEQ ID NO:12 is nucleotide sequence of T4 fragment (Table VII)
SEQ ID NO:13 is nucleotide sequence of Core TM cDNA using L3 (Table IX)
SEQ ID NO:14 is nucleotide sequence of L3 fragment (Table VI.A)
SEQ ID NO:15 is nucleotide sequence of D1 fragment (Table V.A)
SEQ ID NO:16 is nucleotide sequence of TpS2 (Table X)
SEQ ID NO:17 is amino acid sequence of "full length" TM cDNA (Table II)
SEQ ID NO:18 is amino acid sequence of Core TM cDNA (Table VII)
SEQ ID NO:19 is amino acid sequence of C2 fragment (Table IV)
SEQ ID NO:20 is amino acid sequence of D1.1 fragment (Table V)
SEQ ID NO:21 is amino acid sequence of L3D fragment (Table VI)
SEQ ID NO:22 is amino acid sequence of T4 fragment (Table VII)
SEQ ID NO:23 is amino acid sequence of Core TM cDNA using L3 (Table IX)
SEQ ID NO:24 is amino acid sequence of L3 fragment (Table VI.A)
SEQ ID NO:25 is amino acid sequence of D1 fragment (Table V.A)
SEQ ID NO:26 is amino acid sequence of TpS2 (Table X)
SEQ ID NO:27 is complementary nucleotide sequence of "full length" TM cDNA (Table II)
SEQ ID NO:28 is complementary nucleotide sequence of Core TM cDNA (Table VIII)
SEQ ID NO:29 is complementary nucleotide sequence of C2 fragment (Table IV)
SEQ ID NO:30 is complementary nucleotide sequence of D1.1 fragment (Table V)
SEQ ID NO:31 is complementary nucleotide sequence of L3D fragment (Table VI)
SEQ ID NO:32 is complementary nucleotide sequence of T4 fragment (Table VII)
SEQ ID NO:33 is complementary nucleotide sequence of Core TM cDNA using L3 (Table IX)
SEQ ID NO:34 is complementary nucleotide sequence of L3 fragment (Table VI.A)
SEQ ID NO:35 is complementary nucleotide sequence of D1 fragment (Table V.A)
SEQ ID NO:36 is complementary nucleotide sequence of TpS2 (Table X)
SEQ ID NO:37 is Domain 1, 13 amino acid peptide with substantial β-sheet character
SEQ ID NO:38 is peptide recognized by the tobacco etch virus protease Nia
SEQ ID NO:39 is amino acid residues from pro-cathepsin E
SEQ ID NO:40 is linker from procathepsin
SEQ ID NO:41 is linker from polyimmunoglobulin receptor
SEQ ID NO:42 is nucleotide sequence of secretion signal from pMelBac
SEQ ID NO:43 is amino acid sequence of secretion signal from pMelBac
SEQ ID NO:44 is endomembrane retention signal
SEQ ID NO:45 is residues 585–600 of polyimmunoglobulin receptor
SEQ ID NO:46 is Oligonucleotide 1
SEQ ID NO:47 is Oligonucleotide 2
SEQ ID NO:48 is Oligonucleotide 1.1
SEQ ID NO:49 is Oligonucleotide 1.2
SEQ ID NO:50 is Oligonucleotide 1.2ser
SEQ ID NO:51 is Oligonucleotide 2.2ser
SEQ ID NO:52 is Oligonucleotide 1.2val
SEQ ID NO:53 is Oligonucleotide 2.2val
SEQ ID NO:54 is Oligonucleotide 3
SEQ ID NO:55 is Oligonucleotide 4
SEQ ID NO:56 is Oligonucleotide 5
SEQ ID NO:57 is Oligonucleotide 5.1dg
SEQ ID NO:58 is Oligonucleotide 6
SEQ ID NO:59 is Oligonucleotide 6.1dg
SEQ ID NO:60 is Oligonucleotide 7
SEQ ID NO:61 is Oligonucleotide 8
SEQ ID NO:62 is Oligonucleotide 9
SEQ ID NO:63 is Oligonucleotide 9L3Δ
SEQ ID NO:64 is Oligonucleotide 10L3Δ
SEQ ID NO:65 is Oligonucleotide 9L3ΔKDEL
SEQ ID NO:66 is Oligonucleotide 10L3ΔKDEL
SEQ ID NO:67 is Oligonucleotide 9.2Δ3
SEQ ID NO:68 is Oligonucleotide 10.2Δ3
SEQ ID NO:69 is Oligonucleotide 9.3Δ3/ser68
SEQ ID NO:70 is Oligonucleotide 10.3Δ3/ser68
SEQ ID NO:71 is Oligonucleotide 9.3Δ3/val68
SEQ ID NO:72 is Oligonucleotide 10.3Δ3/val68
SEQ ID NO:73 is Oligonucleotide 10
SEQ ID NO:74 is Oligonucleotide 11
SEQ ID NO:75 is Oligonucleotide 12
SEQ ID NO:76 is Oligonucleotide 13
SEQ ID NO:77 is Oligonucleotide 14
SEQ ID NO:78 is Oligonucleotide 15
SEQ ID NO:79 is Oligonucleotide 16
SEQ ID NO:80 is Oligonucleotide 15KDEL
SEQ ID NO:81 is Oligonucleotide 16KDEL
SEQ ID NO:82 is Oligonucleotide P1
SEQ ID NO:83 is Oligonucleotide P2
SEQ ID NO:84 is nuclear targeting sequence 1
SEQ ID NO:85 is nuclear target sequence 2
SEQ ID NO:86 is HDEL linker sequence for intracellular targeting
SEQ ID NO:87 is Oligonucleotide Tp1
SEQ ID NO:88 is Oligonucleotide Tp2
SEQ ID NO:89 is Oligonucleotide Tp3
SEQ ID NO:90 is Oligonucleotide Tp4
SEQ ID NO:91 is Oligonucleotide Tp5
SEQ ID NO:92 is Oligonucleotide Tp6
SEQ ID NO:93 is synthetic peptide linker

We claim:

1. A targeting molecule linked to at least one imaging agent, wherein said targeting molecule is a polypeptide that:
   (a) forms a closed covalent loop;
   (b) contains at least three peptide domains having β-sheet character, each of the domains being separated by domains lacking β-sheet character; and
   (c) specifically binds to a basolateral factor attached to a basolateral domain of an epithelial surface, causing uptake of the linked imaging agent into cells of the epithelial surface;
   wherein said polypeptide is (i) a J chain, or a portion thereof such that the ability of the portion to specifically bind to a basolateral factor attached to a basolateral domain of an epithelial surface causing uptake of the linked imaging agent into cells of the epithelial surface, is not substantially reduced; or (ii) a J chain, or portion thereof, that is linked to an immunoglobulin heavy chain or a portion thereof,
   wherein the targeting molecule does not comprise an immunoglobulin light chain.

2. A targeting molecule linked to at least one imaging agent according to claim 1, wherein said targeting molecule is covalently linked to at least one imaging agent.

3. A targeting molecule linked to at least one imaging agent according to claim 2, wherein said molecule contains at least one cysteine residue linked to the imaging agent(s).

4. A targeting molecule linked to at least one imaging agent according to claim 2, wherein said molecule is linked to an imaging agent via a peptide bond.

5. A targeting molecule linked to at least one imaging agent according to claim 1, wherein said molecule is non-covalently linked to at least one imaging agent.

6. A targeting molecule linked to at least one imaging agent according to claim 1 wherein said polypeptide comprises amino acid residues 13–71 and 93–101 of SEQ ID NO:1, amino acid residues 13–71 and 93–99 of SEQ ID NO:2, amino acid residues 12–70 and 92–101 of SEQ ID NO:3, amino acid residues 12–70 and 92–100 of SEQ ID NO:4, amino acid residues 11–69 and 89–96 of SEQ ID NO:5 and/or amino acid residues 3–61 and 79–88 of SEQ ID NO:6.

7. A targeting molecule linked to at least one imaging agent according to claim 1, wherein said polypeptide comprises the amino acid sequence recited in SEQ ID NO:7.

8. A targeting molecule linked to at least one imaging agent according to claim 1, wherein said polypeptide comprises the amino acid sequence recited in SEQ ID NO:8.

9. A targeting molecule linked to at least one imaging agent according to claim 1, wherein said polypeptide comprises the amino acid sequence recited in SEQ ID NO:13.

10. A targeting molecule linked to at least one imaging agent according to claim 1, wherein said polypeptide contains at least four peptide domains having β-sheet character, separated by domains lacking β-sheet character.

11. A targeting molecule linked to at least one imaging agent according to claim 1, wherein said polypeptide further comprises a linear N-terminal domain.

12. A targeting molecule linked to at least one imaging agent according to claim 1 wherein said N-terminal domain comprises amino acid residues 1–12 of SEQ ID NO:1, amino acid residues 1–12 of SEQ ID NO:2, amino acid residues 1–11 of SEQ ID NO:3, amino acid residues 1–11 of SEQ ID NO:4, amino acid residues 1–10 of SEQ ID NO:5, and/or amino acid residues 1–2 of SEQ ID NO:6.

13. A targeting molecule linked to at least one imaging agent according to claim 1, wherein said polypeptide further comprises a C-terminal domain.

14. A targeting molecule linked to at least one imaging agent according to claim 13, wherein said C-terminal domain comprises a linear peptide having β-sheet character.

15. A targeting molecule linked to at least one imaging agent according to claim 11 wherein said N-terminal domain comprises amino acid residues 102–108 of SEQ ID NO:1, amino acid residues 100–106 of SEQ ID NO:2, amino acid residues 102–108 of SEQ ID NO:3, amino acid residues 101–107 of SEQ ID NO:4 and/or amino acid residues 89–99 of SEQ ID NO:6.

16. A targeting molecule according linked to at least one imaging agent to claim 13, wherein said C-terminal domain comprises a covalently closed loop.

17. A targeting molecule linked to at least one imaging agent according to claim 16 wherein the covalently closed loop within said C-terminal domain comprises amino acid residues 109–137 of SEQ ID NO:1, amino acid residues 107–135 of SEQ ID NO:2, amino acid residues 109–137 of SEQ ID NO:3, amino acid residues 108–136 of SEQ ID NO:4, amino acid residues 96–119 of SEQ ID NO:5, and/or amino acid residues 100–128 of SEQ ID NO:6.

18. A targeting molecule linked to at least one imaging agent according to claim 1, wherein:
(a) at least one imaging agent comprises an antibody or antigen-binding fragment thereof; and
(b) said targeting molecule is linked to a side chain of amino acids in an antigen combining site of the antibody or antigen-binding fragment thereof.

19. A targeting molecule linked to at least one imaging agent according to claim 1, wherein the imaging agent is not naturally linked to the targeting molecule.

20. A targeting molecule linked to at least one imaging agent according to claim 1, wherein said targeting molecule is linked to at least one imaging agent by a substrate for an intracellular or extracellular enzyme associated an an epithelial surface.

21. A targeting molecule linked to at least one imaging agent, wherein said targeting molecule specifically binds to a basolateral factor attached to a basolateral domain of an epithelial surface, causing uptake of the linked imaging agent into cells of the epithelial surface; and wherein said targeting molecule is (i) a J chain polypeptide, or a portion thereof such that the ability of the portion to specifically bind to a basolateral factor attached to a basolateral domain of an epithelial surface, is not substantially reduced; or (ii) a J chain polypeptide, or portion thereof, that is linked to an immunoglobulin heavy chain or a portion thereof,
wherein the targeting molecule does not comprise an immunoglobulin light chain.

22. A targeting molecule linked to at least one imaging agent according to claim 1 or claim 21, wherein said imaging agent is selected from the group consisting of metals, radioactive isotopes, radioopaque agents, radiolucent agents, contrast agents, dyes and enzymes.

23. A pharmaceutical composition comprising a targeting molecule linked to at least one imaging agent, according to claim 1 or claim 21 in combination with a pharmaceutically acceptable carrier.

24. A method for diagnosing a disease in a patient, comprising administering to a patient a pharmaceutical composition according to claim 23 and detecting the presence of imaging agent within the patient.

25. A targeting molecule linked to at least one imaging agent according to claim 21, wherein:
(a) at least one imaging agent comprises an antibody or antigen-binding fragment thereof, and
(b) said targeting molecule is linked to a side chain of amino acids in an antigen combining site of the antibody or antigen-binding fragment thereof.

26. A targeting molecule linked to at least one imaging agent according to claim 21, wherein the imaging agent is not naturally linked to the targeting molecule.

27. A targeting molecule linked to at least one imaging agent according to claim 21, wherein said targeting molecule is linked to at least one imaging agent by a substrate for an intracellular or extracellular enzyme associated with an epithelial surface.

28. A targeting molecule linked to at least one imaging agent, wherein said targeting molecule is a polypeptide comprising a sequence recited in any one of SEQ ID NO:1–SEQ ID NO:6;
wherein said polypeptide:
(a) forms a closed covalent loop;
(b) contains at least three peptide domains having β-sheet character, each of the domains being separated by domains lacking β-sheet character; and
(c) specifically binds to a basolateral factor attached to a basolateral domain of an epithelial surface, causing uptake of the linked imaging agent into cells of the epithelial surface; and
wherein said polypeptide is (i) a J chain, or a portion thereof such that the ability of the portion to specifically bind to a basolateral factor attached to a basolateral domain of an epithelial surface causing uptake of the linked imaging agent into cells of the epithelial surface, is not substantially reduced; or (ii) a J chain, or portion thereof, that is linked to an immunoglobulin heavy chain or a portion thereof,
wherein the targeting molecule does not comprise an immunoglobulin light chain.

29. A targeting molecule linked to at least one imaging agent, wherein said targeting molecule is a polypeptide comprising a sequence recited in SEQ ID NO:7;
wherein said polypeptide:
(a) forms a closed covalent loop;
(b) contains at least three peptide domains having β-sheet character, each of the domains being separated by domains lacking β-sheet character; and
(c) specifically binds to a basolateral factor attached to a basolateral domain of an epithelial surface, causing uptake of the linked imaging agent into cells of the epithelial surface; and
wherein said polypeptide is (i) a J chain, or a portion thereof such that the ability of the portion to specifically bind to a basolateral factor attached to a basolateral domain of an epithelial surface causing uptake of the linked imaging agent into cells of the epithelial surface, is not substantially reduced; or (ii) a J chain, or portion thereof, that is linked to an immunoglobulin heavy chain or a portion thereof,
wherein the targeting molecule does not comprise an immunoglobulin light chain.

30. A targeting molecule linked to at least one imaging agent, wherein said targeting molecule is a polypeptide comprising a sequence recited in SEQ ID NO:8;
wherein said polypeptide:

(a) forms a closed covalent loop;
(b) contains at least three peptide domains having β-sheet character, each of the domains being separated by domains lacking β-sheet character; and
(c) specifically binds to a basolateral factor attached to a basolateral domain of an epithelial surface, causing uptake of the linked imaging agent into cells of the epithelial surface; and wherein said polypeptide is (i) a J chain, or a portion thereof such that the ability of the portion to specifically bind to a basolateral factor attached to a basolateral domain of an epithelial surface causing uptake of the linked imaging agent into cells of the epithelial surface, is not substantially reduced; or (ii) a J chain, or portion thereof, that is linked to an immunoglobulin heavy chain or a portion thereof, wherein the targeting molecule does not comprise an immunoglobulin light chain.

31. A targeting molecule linked to at least one imaging agent, wherein said targeting molecule is a polypeptide comprising a sequence recited in SEQ ID NO:13;

wherein said polypeptide:

(a) forms a closed covalent loop;

(b) contains at least three peptide domains having β-sheet character, each of the domains being separated by domains lacking β-sheet character; and (c) specifically binds to a basolateral factor attached to a basolateral domain of an epithelial surface, causing uptake of the linked imaging agent into cells of the epithelial surface; and wherein said polypeptide is (i) a J chain, or a portion thereof such that the ability of the portion to specifically bind to a basolateral factor attached to a basolateral domain of an epithelial surface causing uptake of the linked imaging agent into cells of the epithelial surface, is not substantially reduced; or (ii) a J chain, or portion thereof, that is linked to an immunoglobulin heavy chain or a portion thereof, wherein the targeting molecule dose not comprise an immunoglobulin light chain.

32. A targeting molecule linked to at least one imaging agent according to any one of claims 28, 31 wherein said targeting molecule is covalently linked to at least one imaging agent.

33. A targeting molecule linked to at least one imaging agent according to claim 32, wherein said targeting molecule contains at least one cysteine residue linked to the imaging agents(s).

34. A targeting molecule linked to at least one imaging agent according to claim 32, wherein said molecule is linked to an imaging agent via a peptide bond.

35. A targeting molecule linked to at least one imaging agent according to claim 32 wherein said molecule is linked to a biological agent via a glycoside bond.

36. A targeting molecule linked to at least one imaging agent according to claim 32 wherein said molecule is linked to a biological agent via a phosphodiester bond.

37. A targeting molecule linked to at least one imaging agent according to any one of claims 28, 31, wherein said molecule is noncovalently linked to at least one imaging agent.

* * * * *

UNITED STATES PATENT AND TRADEMARK OFFICE
CERTIFICATE OF CORRECTION

PATENT NO : 6,045,774
DATED : Apr. 4, 2000
INVENTOR(S) : Andrew C Hiatt, Mich B. Hein, John H. Fitchen It is certified that errors appear in the above-identified patent and that said Letters Patent are hereby corrected as shown below:

Claim 20, column 93, lines 42-43, "associated an an epithelial" should read --associated with an epithelial--.
Claim 21, column 93, line 52, "surface, is not" should read --surface causing uptake of the linked imaging agent into cells of the epithelial surface, is not--.
Claim 25, column 94, line 6, "fragment thereof, and" should read --fragment thereof; and--.
Claim 31, column 96, line 7, "molecule dose not" should read --molecule does not--.
Claim 32, column 96, line 11, "claims 28, 31" should read --claims 28-31--.
Claim 33, column 96, line 17, "agents(s)" should read --agent(s)--.
Claim 37, column 96, line 29, "claims 28, 31" should read --claims 28-31--.

Signed and Sealed this

First Day of May, 2001

Attest:

NICHOLAS P. GODICI

Attesting Officer    Acting Director of the United States Patent and Trademark Office

UNITED STATES PATENT AND TRADEMARK OFFICE
CERTIFICATE OF CORRECTION

PATENT NO. : 6,045,774
DATED : April 4, 2000
INVENTOR(S) : Andrew C. Hiatt, Mich B. Hein and John H. Fitchen It is certified that error appears in the above-identified patent and that said Letters Patent is hereby corrected as shown below:

<u>Title page,</u>
Item [73], Assignee: "EPlcyte Pharmaceutical, Inc." should read
-- Epicyte Pharmaceutical, Inc. --.

Signed and Sealed this

Fourth Day of March, 2003

JAMES E. ROGAN
*Director of the United States Patent and Trademark Office*

SEQUENCE LISTING (1) GENERAL INFORMATION:

(iii) NUMBER OF SEQUENCES: 93

(2) INFORMATION FOR SEQ ID NO:1:

(i) SEQUENCE CHARACTERISTICS:
       (A) LENGTH: 137 amino acids
       (B) TYPE: amino acid
       (C) STRANDEDNESS:
       (D) TOPOLOGY: linear (xi) SEQUENCE DESCRIPTION: SEQ ID NO:1:

```
Gln Glu Asp Glu Arg Ile Val Leu Val Asp Asn Lys Cys Lys Cys Ala
1               5                   10                  15

Arg Ile Thr Ser Arg Ile Ile Arg Ser Ser Glu Asp Pro Asn Glu Asp
            20                  25                  30

Ile Val Glu Arg Asn Ile Arg Ile Ile Val Pro Leu Asn Asn Arg Glu
        35                  40                  45

Asn Ile Ser Asp Pro Thr Ser Pro Leu Arg Thr Arg Pro Val Tyr His
    50                  55                  60

Leu Ser Asp Leu Cys Lys Lys Cys Asp Pro Thr Glu Val Glu Leu Asp
65                  70                  75                  80

Asn Gln Ile Val Thr Ala Thr Gln Ser Asn Ile Cys Asp Glu Asp Ser
                85                  90                  95

Ala Thr Glu Thr Cys Tyr Thr Tyr Asp Arg Asn Lys Cys Tyr Thr Ala
            100                 105                 110

Val Val Pro Leu Val Tyr Gly Gly Glu Thr Lys Met Val Glu Thr Ala
        115                 120                 125

Leu Thr Pro Asp Ala Cys Tyr Pro Asp
    130                 135
```

(2) INFORMATION FOR SEQ ID NO:2:

(i) SEQUENCE CHARACTERISTICS:
       (A) LENGTH: 135 amino acids
       (B) TYPE: amino acid
       (C) STRANDEDNESS:
       (D) TOPOLOGY: linear (xi) SEQUENCE DESCRIPTION: SEQ ID NO:2:

```
Gln Asp Glu Asn Glu Arg Ile Val Val Asp Asn Lys Cys Lys Cys Ala
1               5                   10                  15

Arg Ile Thr Ser Arg Ile Ile Pro Ser Ala Glu Asp Pro Ser Gln Asp
            20                  25                  30

Ile Val Glu Arg Asn Val Arg Ile Ile Val Pro Leu Asn Ser Arg Glu
        35                  40                  45

Asn Ile Ser Asp Pro Thr Ser Pro Met Arg Thr Lys Pro Val Tyr His
    50                  55                  60

Leu Ser Asp Leu Cys Lys Lys Cys Asp Thr Thr Glu Val Glu Leu Glu
65                  70                  75                  80

Asp Gln Val Val Thr Ala Ser Gln Ser Asn Ile Cys Asp Ser Asp Ala
                85                  90                  95

Glu Thr Cys Tyr Thr Tyr Asp Arg Asn Lys Cys Tyr Thr Asn Arg Val
            100                 105                 110
```

```
Lys Leu Ser Tyr Arg Gly Gln Thr Lys Met Val Glu Thr Ala Leu Thr
        115                 120                 125

Pro Asp Ser Cys Tyr Pro Asp
    130                 135

(2) INFORMATION FOR SEQ ID NO:3:

(i) SEQUENCE CHARACTERISTICS:
        (A) LENGTH: 137 amino acids
        (B) TYPE: amino acid
        (C) STRANDEDNESS:
        (D) TOPOLOGY: linear (xi) SEQUENCE DESCRIPTION: SEQ ID NO:3:

Asp Asp Glu Ala Thr Ile Leu Ala Asp Asn Lys Cys Met Cys Thr Arg
1               5                   10                  15

Val Thr Ser Arg Ile Ile Pro Ser Thr Glu Asp Pro Asn Glu Asp Ile
            20                  25                  30

Val Glu Arg Asn Ile Arg Ile Val Val Pro Leu Asn Asn Arg Glu Asn
            35                  40                  45

Ile Ser Asp Pro Thr Ser Pro Leu Arg Arg Asn Pro Val Tyr His Leu
50                  55                  60

Ser Asp Val Cys Lys Lys Cys Asp Pro Val Glu Val Glu Leu Glu Asp
65                  70                  75                  80

Gln Val Val Thr Ala Thr Gln Ser Asn Ile Cys Asn Glu Asp Asp Gly
                85                  90                  95

Val Pro Glu Thr Cys Tyr Met Tyr Asp Arg Asn Lys Cys Tyr Thr Thr
            100                 105                 110

Met Val Pro Leu Arg Tyr His Gly Glu Thr Lys Met Val Gln Ala Ala
            115                 120                 125

Leu Thr Pro Asp Ser Cys Tyr Pro Asp
130                 135

(2) INFORMATION FOR SEQ ID NO:4:

(i) SEQUENCE CHARACTERISTICS:
        (A) LENGTH: 136 amino acids
        (B) TYPE: amino acid
        (C) STRANDEDNESS:
        (D) TOPOLOGY: linear (xi) SEQUENCE DESCRIPTION: SEQ ID NO:4:

Glu Asp Glu Ser Thr Val Leu Val Asp Asn Lys Cys Gln Cys Val Arg
1               5                   10                  15

Ile Thr Ser Arg Ile Ile Arg Asp Pro Asp Asn Pro Ser Glu Asp Ile
            20                  25                  30

Val Glu Arg Asn Ile Arg Ile Ile Val Pro Leu Asn Thr Arg Glu Asn
            35                  40                  45

Ile Ser Asp Pro Thr Ser Pro Leu Arg Thr Glu Pro Lys Tyr Asn Leu
50                  55                  60

Ala Asn Leu Cys Lys Lys Cys Asp Pro Thr Glu Ile Glu Leu Asp Asn
65                  70                  75                  80

Gln Val Phe Thr Ala Ser Gln Ser Asn Ile Cys Pro Asp Asp Tyr
                85                  90                  95

Ser Glu Thr Cys Tyr Thr Tyr Asp Arg Asn Lys Cys Tyr Thr Thr Leu
            100                 105                 110

Val Pro Ile Thr His Arg Gly Val Thr Arg Met Val Lys Ala Thr Leu
            115                 120                 125
```

```
Thr Pro Asp Ser Cys Tyr Pro Asp
    130                 135
```

(2) INFORMATION FOR SEQ ID NO:5:

(i) SEQUENCE CHARACTERISTICS:
        (A) LENGTH: 119 amino acids
        (B) TYPE: amino acid
        (C) STRANDEDNESS:
        (D) TOPOLOGY: linear (xi) SEQUENCE DESCRIPTION: SEQ ID NO:5:

```
Glu Gln Glu Tyr Ile Leu Ala Asn Asn Lys Cys Lys Cys Val Lys Ile
1               5                   10                  15

Ser Ser Arg Phe Val Pro Ser Thr Glu Arg Pro Gly Glu Glu Ile Leu
            20                  25                  30

Glu Arg Asn Ile Gln Ile Thr Ile Pro Thr Ser Ser Arg Met Xaa Ile
            35                  40                  45

Ser Asp Pro Tyr Ser Pro Leu Arg Thr Gln Pro Val Tyr Asn Leu Trp
50                  55                  60

Asp Ile Cys Gln Lys Cys Asp Pro Val Gln Leu Glu Ile Gly Gly Ile
65                  70                  75                  80

Pro Val Leu Ala Ser Gln Pro Xaa Xaa Ser Xaa Pro Asp Asp Glu Cys
                85                  90                  95

Tyr Thr Thr Glu Val Asn Phe Lys Lys Lys Val Pro Leu Thr Pro Asp
                100                 105                 110

Ser Cys Tyr Glu Tyr Ser Glu
            115
```

(2) INFORMATION FOR SEQ ID NO:6:

(i) SEQUENCE CHARACTERISTICS:
        (A) LENGTH: 128 amino acids
        (B) TYPE: amino acid
        (C) STRANDEDNESS:
        (D) TOPOLOGY: linear (xi) SEQUENCE DESCRIPTION: SEQ ID NO:6:

```
Asn Lys Cys Met Cys Thr Arg Val Thr Ala Arg Ile Arg Gly Thr Arg
1               5                   10                  15

Glu Asp Pro Asn Glu Asp Ile Val Glu Arg Tyr Ile Arg Ile Asn Val
            20                  25                  30

Pro Leu Lys Asn Arg Gly Asn Ile Ser Asp Pro Thr Ser Pro Leu Arg
            35                  40                  45

Asn Gln Pro Val Tyr His Leu Ser Pro Ser Cys Lys Lys Cys Asp Pro
50                  55                  60

Tyr Glu Asp Gly Val Val Thr Ala Thr Glu Thr Asn Ile Cys Tyr Pro
65                  70                  75                  80

Asp Gln Gly Val Pro Gln Ser Cys Arg Asp Tyr Cys Pro Glu Leu Asp
                85                  90                  95

Arg Asn Lys Cys Tyr Thr Val Leu Val Pro Pro Gly Tyr Thr Gly Glu
                100                 105                 110

Thr Lys Met Val Gln Asn Ala Leu Thr Pro Asp Ala Cys Tyr Pro Asp
            115                 120                 125
```

(2) INFORMATION FOR SEQ ID NO:7:

(i) SEQUENCE CHARACTERISTICS:
        (A) LENGTH: 421 base pairs
        (B) TYPE: nucleic acid (C) STRANDEDNESS: single
        (D) TOPOLOGY: linear (ix) FEATURE:
        (A) NAME/KEY: CDS
        (B) LOCATION: 1..414

(xi) SEQUENCE DESCRIPTION: SEQ ID NO:7:

```
GAT CAG GAA GAT GAA CGT ATT GTT CTG GTT GAC AAC AAG TGC AAG TGT           48
Asp Gln Glu Asp Glu Arg Ile Val Leu Val Asp Asn Lys Cys Lys Cys
 1               5                  10                  15

GCT CGT ATT ACT TCT AGA ATC ATC CGT AGC TCA GAG GAC CCA AAT GAA           96
Ala Arg Ile Thr Ser Arg Ile Ile Arg Ser Ser Glu Asp Pro Asn Glu
             20                  25                  30

GAT ATA GTC GAA CGT AAC ATC CGT ATC ATC GTC CCA CTG AAT AAC CGG          144
Asp Ile Val Glu Arg Asn Ile Arg Ile Ile Val Pro Leu Asn Asn Arg
         35                  40                  45

GAG AAT ATC TCA GAT CCT ACA AGT CCG TTG CGC ACA CGC TTC GTA TAC          192
Glu Asn Ile Ser Asp Pro Thr Ser Pro Leu Arg Thr Arg Phe Val Tyr
     50                  55                  60

CAC CTG TCA GAT CTG TGT AAG AAG TGT GAT CCA ACA GAG GTA GAG CTG          240
His Leu Ser Asp Leu Cys Lys Lys Cys Asp Pro Thr Glu Val Glu Leu
 65                  70                  75                  80

GAC AAT CAG ATA GTC ACT GCG ACT CAA AGC AAC ATT TGC GAT GAG GAC          288
Asp Asn Gln Ile Val Thr Ala Thr Gln Ser Asn Ile Cys Asp Glu Asp
                 85                  90                  95

AGC GCT ACA GAA ACC TGC AGC ACC TAC GAT AGG AAC AAA TGC TAC ACG          336
Ser Ala Thr Glu Thr Cys Ser Thr Tyr Asp Arg Asn Lys Cys Tyr Thr
            100                 105                 110

GCC GTG GTT CCG CTC GTG TAT GGT GGA GAG ACA AAA ATG GTG GAA ACT          384
Ala Val Val Pro Leu Val Tyr Gly Gly Glu Thr Lys Met Val Glu Thr
        115                 120                 125

GCC CTT ACG CCC GAT GCA TGC TAT CCG GAC TGAATTC                          421
Ala Leu Thr Pro Asp Ala Cys Tyr Pro Asp
    130                 135
```

(2) INFORMATION FOR SEQ ID NO:8:

(i) SEQUENCE CHARACTERISTICS:
        (A) LENGTH: 215 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..213

(xi) SEQUENCE DESCRIPTION: SEQ ID NO:8:

```
GAT CAG AAG TGC AAG TGT GCT CGT ATT ACT TCT AGA ATC ATC CGT AGC           48
Asp Gln Lys Cys Lys Cys Ala Arg Ile Thr Ser Arg Ile Ile Arg Ser
 1               5                  10                  15

TCA GAG GAC CCA AAT GAA GAT ATA GTC GAA CGT AAC ATC CGT ATC ATC           96
Ser Glu Asp Pro Asn Glu Asp Ile Val Glu Arg Asn Ile Arg Ile Ile
             20                  25                  30

GTC CCA CTG AAT AAC CGG GAG AAT ATC TCA GAT CCT ACA AGT CCG TTG          144
Val Pro Leu Asn Asn Arg Glu Asn Ile Ser Asp Pro Thr Ser Pro Leu
         35                  40                  45

CGC ACA CGC TTC GTA TAC CAC CTG TCA GAT CTG TGT AAG AAG GAT GAG          192
Arg Thr Arg Phe Val Tyr His Leu Ser Asp Leu Cys Lys Lys Asp Glu
     50                  55                  60

GAC AGC GCT ACA GAA ACC TGC TG                                           215
Asp Ser Ala Thr Glu Thr Cys
 65                  70
```

(2) INFORMATION FOR SEQ ID NO:9:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (xi) SEQUENCE DESCRIPTION: SEQ ID NO:9:

```
CTAGAATCAT CCGTAGCTCA GAGGACCCAA ATGAAGATAT AGTCGAACGT AACATCCGTA      60

TCATCGTCCC ACTGAATAAC CGGGAGAATA TCTCAGATCC TACAAGTCCG TTGCGCACAC     120

GCTTCGTATA CCACCTGTCA                                                 140
```

(2) INFORMATION FOR SEQ ID NO:10:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:10:

```
GATCAGAAGT GCAAGTGTGC TCGTATTACT T                                    31
```

(2) INFORMATION FOR SEQ ID NO:11:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..42

(xi) SEQUENCE DESCRIPTION: SEQ ID NO:11:

```
GAT CTG TGT AAG AAG GAT GAA GAT TCC GCT ACA GAA ACC TGC               42
Asp Leu Cys Lys Lys Asp Glu Asp Ser Ala Thr Glu Thr Cys
             75                  80                  85

TG                                                                    44
```

(2) INFORMATION FOR SEQ ID NO:12:

(i) SEQUENCE CHARACTERISTICS:
        (A) LENGTH: 109 base pairs
        (B) TYPE: nucleic acid
        (C) STRANDEDNESS: single
        (D) TOPOLOGY: linear (xi) SEQUENCE DESCRIPTION: SEQ ID NO:12:

```
GCACCTACGA TAGGAACAAA TGCTACACGG CCGTGGTTCC GCTCGTGTAT GGTGGAGAGA      60

CAAAAATGGT GGAAACTGCC CTTACGCCCG ATGCATGCTA CCCTGACTG                 109
```

(2) INFORMATION FOR SEQ ID NO:13:

(i) SEQUENCE CHARACTERISTICS:
        (A) LENGTH: 286 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..282

(xi) SEQUENCE DESCRIPTION: SEQ ID NO:13:

| | | | | | | | | | | | | | | | | |
|---|---|---|---|---|---|---|---|---|---|---|---|---|---|---|---|---|
| GAC | AAC | AAG | TGC | AAG | TGT | GCT | CGT | ATT | ACT | TCT | AGA | ATC | ATC | CGT | AGC | 48 |
| Asp | Asn | Lys | Cys | Lys | Cys | Ala | Arg | Ile | Thr | Ser | Arg | Ile | Ile | Arg | Ser | |
| 15 | | | | 20 | | | | | 25 | | | | | 30 | | |

| | | | | | | | | | | | | | | | | |
|---|---|---|---|---|---|---|---|---|---|---|---|---|---|---|---|---|
| TCA | GAG | GAC | CCA | AAT | GAA | GAT | ATA | GTC | GAA | CGT | AAC | ATC | CGT | ATC | ATC | 96 |
| Ser | Glu | Asp | Pro | Asn | Glu | Asp | Ile | Val | Glu | Arg | Asn | Ile | Arg | Ile | Ile | |
| | | | | 35 | | | | | 40 | | | | | 45 | | |

| | | | | | | | | | | | | | | | | |
|---|---|---|---|---|---|---|---|---|---|---|---|---|---|---|---|---|
| GTC | CCA | CTG | AAT | AAC | CGG | GAG | AAT | ATC | TCA | GAT | CCT | ACA | AGT | CCG | TTG | 144 |
| Val | Pro | Leu | Asn | Asn | Arg | Glu | Asn | Ile | Ser | Asp | Pro | Thr | Ser | Pro | Leu | |
| | | 50 | | | | | 55 | | | | | 60 | | | | |

| | | | | | | | | | | | | | | | | |
|---|---|---|---|---|---|---|---|---|---|---|---|---|---|---|---|---|
| CGC | ACA | CGC | TTC | GTA | TAC | CAC | CTG | TCA | GAT | CTG | TGT | AAG | AAG | TGT | GAT | 192 |
| Arg | Thr | Arg | Phe | Val | Tyr | His | Leu | Ser | Asp | Leu | Cys | Lys | Lys | Cys | Asp | |
| | | 65 | | | | | 70 | | | | | 75 | | | | |

| | | | | | | | | | | | | | | | | |
|---|---|---|---|---|---|---|---|---|---|---|---|---|---|---|---|---|
| CCA | ACA | GAG | GTA | GAG | CTG | GAC | AAT | CAG | ATA | GTC | ACT | GCG | ACT | CAA | AGC | 240 |
| Pro | Thr | Glu | Val | Glu | Leu | Asp | Asn | Gln | Ile | Val | Thr | Ala | Thr | Gln | Ser | |
| | 80 | | | | | 85 | | | | | 90 | | | | | |

| | | | | | | | | | | | |
|---|---|---|---|---|---|---|---|---|---|---|---|
| AAC | ATT | TGC | GAT | GAG | GAC | AGC | GCT | ACA | GAA | ACC | TGC | TAC | TGA | 282 |
| Asn | Ile | Cys | Asp | Glu | Asp | Ser | Ala | Thr | Glu | Thr | Cys | Tyr | * | |
| 95 | | | | | 100 | | | | | 105 | | | | |

ATTC                                                                                                            286

(2) INFORMATION FOR SEQ ID NO:14:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 1..105

(xi) SEQUENCE DESCRIPTION: SEQ ID NO:14:

| | | | | | | | | | | | | | | | | |
|---|---|---|---|---|---|---|---|---|---|---|---|---|---|---|---|---|
| GAT | CTG | TGT | AAG | AAG | TGT | GAT | CCA | ACA | GAG | GTA | GAG | CTG | GAC | AAT | CAG | 48 |
| Asp | Leu | Cys | Lys | Lys | Cys | Asp | Pro | Thr | Glu | Val | Glu | Leu | Asp | Asn | Gln | |
| 95 | | | | 100 | | | | | 105 | | | | | 110 | | |

| | | | | | | | | | | | | | | | | |
|---|---|---|---|---|---|---|---|---|---|---|---|---|---|---|---|---|
| ATA | GTC | ACT | GCG | ACT | CAA | AGC | AAC | ATT | TGC | GAT | GAG | GAC | AGC | GCT | ACA | 96 |
| Ile | Val | Thr | Ala | Thr | Gln | Ser | Asn | Ile | Cys | Asp | Glu | Asp | Ser | Ala | Thr | |
| | | | 115 | | | | | 120 | | | | | 125 | | | |

CTT TGG ACG                                                                                                     105
Leu Trp Thr (2) INFORMATION FOR SEQ ID NO:15:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:15:

GATCAGGAAG ATGAACGTAT TGTTCTGGTT GACAACAAGT GCAAGTGTGC TCGTATTACT          60
T                                                                         61

(2) INFORMATION FOR SEQ ID NO:16:

(i) SEQUENCE CHARACTERISTICS:
        (A) LENGTH: 198 base pairs
        (B) TYPE: nucleic acid
        (C) STRANDEDNESS: single
        (D) TOPOLOGY: linear (xi) SEQUENCE DESCRIPTION: SEQ ID NO:16:

```
GCGATGACGA CGATAAGGCC CAAACGGAGA CCTGTACTGT TGCGCCTCGT GAACGGCAAA      60

ACTGCGGATT CCCGGAAGTA ACACCCTCTC AGTGCGCTAA TAAAGGCTGC TGTTTTGATG     120

ACACGGTACG GGGCGTTCCG TGGTGCTTCT ACCCCAATAC AATTGACGTT CCGCCTGAAG     180

AAGAGTGCGA GCCGTAAG                                                    198
```

(2) INFORMATION FOR SEQ ID NO:17:

(i) SEQUENCE CHARACTERISTICS:
        (A) LENGTH: 138 amino acids
        (B) TYPE: amino acid
        (D) TOPOLOGY: linear (ii) MOLECULE TYPE: protein (xi) SEQUENCE DESCRIPTION: SEQ ID NO:17:

```
Asp Gln Glu Asp Glu Arg Ile Val Leu Val Asp Asn Lys Cys Lys Cys
 1               5                  10                  15

Ala Arg Ile Thr Ser Arg Ile Ile Arg Ser Ser Glu Asp Pro Asn Glu
            20                  25                  30

Asp Ile Val Glu Arg Asn Ile Arg Ile Ile Val Pro Leu Asn Asn Arg
        35                  40                  45

Glu Asn Ile Ser Asp Pro Thr Ser Pro Leu Arg Thr Arg Phe Val Tyr
     50                  55                  60

His Leu Ser Asp Leu Cys Lys Lys Cys Asp Pro Thr Glu Val Glu Leu
 65                  70                  75                  80

Asp Asn Gln Ile Val Thr Ala Thr Gln Ser Asn Ile Cys Asp Glu Asp
                85                  90                  95

Ser Ala Thr Glu Thr Cys Ser Thr Tyr Asp Arg Asn Lys Cys Tyr Thr
            100                 105                 110

Ala Val Val Pro Leu Val Tyr Gly Gly Glu Thr Lys Met Val Glu Thr
        115                 120                 125

Ala Leu Thr Pro Asp Ala Cys Tyr Pro Asp
    130                 135
```

(2) INFORMATION FOR SEQ ID NO:18:

(i) SEQUENCE CHARACTERISTICS:
        (A) LENGTH: 71 amino acids
        (B) TYPE: amino acid
        (D) TOPOLOGY: linear (ii) MOLECULE TYPE: protein (xi) SEQUENCE DESCRIPTION: SEQ ID NO:18:

```
Asp Gln Lys Cys Lys Cys Ala Arg Ile Thr Ser Arg Ile Ile Arg Ser
 1               5                  10                  15

Ser Glu Asp Pro Asn Glu Asp Ile Val Glu Arg Asn Ile Arg Ile Ile
            20                  25                  30

Val Pro Leu Asn Asn Arg Glu Asn Ile Ser Asp Pro Thr Ser Pro Leu
        35                  40                  45

Arg Thr Arg Phe Val Tyr His Leu Ser Asp Leu Cys Lys Lys Asp Glu
     50                  55                  60

Asp Ser Ala Thr Glu Thr Cys
 65                  70
```

(2) INFORMATION FOR SEQ ID NO:19:

(i) SEQUENCE CHARACTERISTICS:
        (A) LENGTH: 49 amino acids
        (B) TYPE: amino acid
        (C) STRANDEDNESS:
        (D) TOPOLOGY: linear (xi) SEQUENCE DESCRIPTION: SEQ ID NO:19:

Ser Arg Ile Ile Arg Ser Ser Glu Asp Pro Asn Glu Asp Ile Val Glu
1               5                   10                  15

Arg Asn Ile Arg Ile Ile Val Pro Leu Asn Asn Arg Glu Asn Ile Ser
                20                  25                  30

Asp Pro Thr Ser Pro Leu Arg Thr Arg Phe Val Tyr His Leu Ser Asp
            35                  40                  45

Leu (2) INFORMATION FOR SEQ ID NO:20:

(i) SEQUENCE CHARACTERISTICS:
        (A) LENGTH: 12 amino acids
        (B) TYPE: amino acid
        (C) STRANDEDNESS:
        (D) TOPOLOGY: linear (xi) SEQUENCE DESCRIPTION: SEQ ID NO:20:

Asp Gln Lys Cys Lys Cys Ala Arg Ile Thr Ser Arg
1               5                   10

(2) INFORMATION FOR SEQ ID NO:21:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:21:

Asp Leu Cys Lys Lys Asp Glu Asp Ser Ala Thr Glu Thr Cys
1               5                   10

(2) INFORMATION FOR SEQ ID NO:22:

(i) SEQUENCE CHARACTERISTICS:
        (A) LENGTH: 36 amino acids
        (B) TYPE: amino acid
        (C) STRANDEDNESS:
        (D) TOPOLOGY: linear (xi) SEQUENCE DESCRIPTION: SEQ ID NO:22:

Ser Thr Tyr Asp Arg Asn Lys Cys Tyr Thr Ala Val Val Pro Leu Val
1               5                   10                  15

Tyr Gly Gly Glu Thr Lys Met Val Glu Thr Ala Leu Thr Pro Asp Ala
                20                  25                  30

Cys Tyr Pro Asp
            35

(2) INFORMATION FOR SEQ ID NO:23:

(i) SEQUENCE CHARACTERISTICS:
        (A) LENGTH: 93 amino acids
        (B) TYPE: amino acid
        (D) TOPOLOGY: linear (ii) MOLECULE TYPE: protein (xi) SEQUENCE DESCRIPTION: SEQ ID NO:23:

```
Asp Asn Lys Cys Lys Cys Ala Arg Ile Thr Ser Arg Ile Ile Arg Ser
 1               5                  10                  15

Ser Glu Asp Pro Asn Glu Asp Ile Val Glu Arg Asn Ile Arg Ile Ile
                20                  25                  30

Val Pro Leu Asn Asn Arg Glu Asn Ile Ser Asp Pro Thr Ser Pro Leu
            35                  40                  45

Arg Thr Arg Phe Val Tyr His Leu Ser Asp Leu Cys Lys Lys Cys Asp
        50                  55                  60

Pro Thr Glu Val Glu Leu Asp Asn Gln Ile Val Thr Ala Thr Gln Ser
65                  70                  75                  80

Asn Ile Cys Asp Glu Asp Ser Ala Thr Glu Thr Cys Tyr
                85                  90
```

(2) INFORMATION FOR SEQ ID NO:24:

(i) SEQUENCE CHARACTERISTICS:
        (A) LENGTH: 35 amino acids
        (B) TYPE: amino acid
        (D) TOPOLOGY: linear (ii) MOLECULE TYPE: protein (xi) SEQUENCE DESCRIPTION: SEQ ID NO:24:

```
Asp Leu Cys Lys Lys Cys Asp Pro Thr Glu Val Glu Leu Asp Asn Gln
 1               5                  10                  15

Ile Val Thr Ala Thr Gln Ser Asn Ile Cys Asp Glu Asp Ser Ala Thr
                20                  25                  30

Leu Trp Thr
        35
```

(2) INFORMATION FOR SEQ ID NO:25:

(i) SEQUENCE CHARACTERISTICS:
        (A) LENGTH: 22 amino acids
        (B) TYPE: amino acid
        (C) STRANDEDNESS:
        (D) TOPOLOGY: linear (xi) SEQUENCE DESCRIPTION: SEQ ID NO:25:

```
Asp Gln Glu Asp Glu Arg Ile Val Leu Val Asp Asn Lys Cys Lys Cys
 1               5                  10                  15

Ala Arg Ile Thr Ser Arg
                20
```

(2) INFORMATION FOR SEQ ID NO:26:

(i) SEQUENCE CHARACTERISTICS:
        (A) LENGTH: 66 amino acids
        (B) TYPE: amino acid
        (C) STRANDEDNESS:
        (D) TOPOLOGY: linear (xi) SEQUENCE DESCRIPTION: SEQ ID NO:26:

```
Cys Ser Asp Asp Asp Asp Lys Ala Gln Thr Glu Thr Cys Thr Val Ala
 1               5                  10                  15

Pro Arg Glu Arg Gln Asn Cys Gly Phe Pro Gly Val Thr Pro Ser Gln
                20                  25                  30

Cys Ala Asn Lys Gly Cys Cys Phe Asp Asp Thr Val Arg Gly Val Pro
            35                  40                  45

Trp Cys Phe Tyr Pro Asn Thr Ile Asp Val Pro Pro Glu Glu Glu Cys
        50                  55                  60
```

Glu Phe
65

(2) INFORMATION FOR SEQ ID NO:27:

(i) SEQUENCE CHARACTERISTICS:
        (A) LENGTH: 421 base pairs
        (B) TYPE: nucleic acid
        (C) STRANDEDNESS: single
        (D) TOPOLOGY: linear (xi) SEQUENCE DESCRIPTION: SEQ ID NO:27:

```
CTAGTCCTTC TACTTGCATA ACAAGACCAA CTGTTGTTCA CGTTCACACG AGCATAATGA      60

AGATCTTAGT AGGCATCGAG TCTCCTGGGT TTACTTCTAT ATCAGCTTGC ATTGTAGGCA     120

TAGTAGCAGG GTGACTTATT GGCCCTCTTA TAGAGTCTAG GATGTTCAGG CAACGCGTGT     180

GCGAAGCATA TGGTGGACAG TCTAGACACA TTCTTCACAC TAGGTTGTCT CCATCTCGAC     240

CTGTTAGTCT ATCAGTGACG CTGAGTTTCG TTGTAAACGC TACTCCTGTC GCGATGTCTT     300

TGGACGTCGT GGATGCTATC CTTGTTTACG ATGTGCCGGC ACCAAGGCGA GCACATACCA     360

CCTCTCTGTT TTTACCACCT TGACGGGAA TGCGGGCTAC GTACGATAGG CCTGACTTAA      420

G                                                                    421
```

(2) INFORMATION FOR SEQ ID NO:28:

(i) SEQUENCE CHARACTERISTICS:
        (A) LENGTH: 219 base pairs
        (B) TYPE: nucleic acid
        (C) STRANDEDNESS: single
        (D) TOPOLOGY: linear (xi) SEQUENCE DESCRIPTION: SEQ ID NO:28:

```
CTAGTCTTCA CGTTCACACG AGCATAATGA AGATCTTAGT AGGCATCGAG TCTCCTGGGT      60

TTACTTCTAT ATCAGCTTGC ATTGTAGGCA TAGTAGCAGG GTGACTTATT GGCCCTCTTA     120

TAGAGTCTAG GATGTTCAGG CAACGCGTGT GCGAAGCATA TGGTGGACAG TCTAGACACA     180

TTCTTCCTAC TCCTGTCGCG ATGTCTTTGG ACGACTTAA                             219
```

(2) INFORMATION FOR SEQ ID NO:29:

(i) SEQUENCE CHARACTERISTICS:
        (A) LENGTH: 140 base pairs
        (B) TYPE: nucleic acid
        (C) STRANDEDNESS: single
        (D) TOPOLOGY: linear (xi) SEQUENCE DESCRIPTION: SEQ ID NO:29:

```
TTAGTAGGCA TCGAGTCTCC TGGGTTTACT TCTATATCAG CTTGCATTGT AGGCATAGTA      60

GCAGGGTGAC TTATTGGCCC TCTTATAGAG TCTAGGATGT TCAGGCAACG CGTGTGCGAA     120

GCATATGGTG GACAGTCTAG                                                 140
```

(2) INFORMATION FOR SEQ ID NO:30:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:30:

```
TCTTCACGTT CACACGAGCA TAATGAAGAT C                                     31
```

(2) INFORMATION FOR SEQ ID NO:31:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:31:

```
ACACATTCTT CCTACTTCTC AGGCGATGTC TTTGGACGAC TTAA                44
```

(2) INFORMATION FOR SEQ ID NO:32:

(i) SEQUENCE CHARACTERISTICS:
        (A) LENGTH: 117 base pairs
        (B) TYPE: nucleic acid
        (C) STRANDEDNESS: single
        (D) TOPOLOGY: linear (xi) SEQUENCE DESCRIPTION: SEQ ID NO:32:

```
ACGTCGTGGA TGCTATCCTT GTTTACGATG TGCCGGCACC AAGGCGAGCA CATACCACCT      60

CTCTGTTTTT ACCACCTTTG ACGGGAATGC GGGCTACGTA CGATGGGACT GACTTAA        117
```

(2) INFORMATION FOR SEQ ID NO:33:

(i) SEQUENCE CHARACTERISTICS:
        (A) LENGTH: 282 base pairs
        (B) TYPE: nucleic acid
        (C) STRANDEDNESS: single
        (D) TOPOLOGY: linear (xi) SEQUENCE DESCRIPTION: SEQ ID NO:33:

```
CTGTTGTTCA CGTTCACACG AGCATAATGA AGATCTTAGT AGGCATCGAG TCTCCTGGGT      60

TTACTTCTAT ATCAGCTTGC ATTGTAGGCA TAGTAGCAGG GTGACTTATT GGCCCTCTTA     120

TAGAGTCTAG GATGTTCAGG CAACGCGTGT GCGAAGCATA TGGTGGACAG TCTAGACACA     180

TTCTTCACAC TAGGTTGTCT CCATCTCGAC CTGTTAGTCT ATCAGTGACG CTGAGTTTCG     240

TTGTAAACGC TACTCCTGTC GCGATGTCTT TGGACGATGA CT                       282
```

(2) INFORMATION FOR SEQ ID NO:34:

(i) SEQUENCE CHARACTERISTICS:
        (A) LENGTH: 105 base pairs
        (B) TYPE: nucleic acid
        (C) STRANDEDNESS: single
        (D) TOPOLOGY: linear (xi) SEQUENCE DESCRIPTION: SEQ ID NO:34:

```
GATCTGTGTA AGAAGTGTGA TCCAACAGAG GTAGAGCTGG ACAATCAGAT AGTCACTGCG      60

ACTCAAAGCA ACATTTGCGA TGAGGACAGC GCTACACTTT GGACG                    105
```

(2) INFORMATION FOR SEQ ID NO:35:

(i) SEQUENCE CHARACTERISTICS:
        (A) LENGTH: 65 base pairs
        (B) TYPE: nucleic acid
        (C) STRANDEDNESS: single
        (D) TOPOLOGY: linear (xi) SEQUENCE DESCRIPTION: SEQ ID NO:35:

```
CTAGTCCTTC TACTTGCATA ACAAGACCAA CTGTTGTTCA CGTTCACACG AGCATAATGA      60

AGATC                                                                 65
```

(2) INFORMATION FOR SEQ ID NO:36:

(i) SEQUENCE CHARACTERISTICS:
        (A) LENGTH: 206 base pairs
        (B) TYPE: nucleic acid
        (C) STRANDEDNESS: single
        (D) TOPOLOGY: linear (xi) SEQUENCE DESCRIPTION: SEQ ID NO:36:

```
ACTTCGCTAC TGCTGCTATT CCGGGTTTGC CTCTGGACAT GACAACGCGG AGCACTTGCC     60

GTTTTGACGC CTAAGGGCCT TCATTGTGGG AGAGTCACGC GATTATTTCC GACGACAAAA    120

CTACTGTGCC ATGCCCCGCA AGGCACCACG AAGATGGGGT TATGTTAACT GCAAGGCGGA    180

CTTCTTCTCA CGCTCGGCAT TCTTAA                                        206
```

(2) INFORMATION FOR SEQ ID NO:37:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:37:

```
Asp Gln Glu Asp Glu Arg Ile Val Leu Val Asp Asn Lys
1               5                   10
```

(2) INFORMATION FOR SEQ ID NO:38:

(i) SEQUENCE CHARACTERISTICS:
        (A) LENGTH: 7 amino acids
        (B) TYPE: amino acid
        (C) STRANDEDNESS:
        (D) TOPOLOGY: linear (xi) SEQUENCE DESCRIPTION: SEQ ID NO:38:

```
Glu Asn Leu Tyr Phe Gln Ser
1               5
```

(2) INFORMATION FOR SEQ ID NO:39:

(i) SEQUENCE CHARACTERISTICS:
        (A) LENGTH: 11 amino acids
        (B) TYPE: amino acid
        (C) STRANDEDNESS:
        (D) TOPOLOGY: linear (xi) SEQUENCE DESCRIPTION: SEQ ID NO:39:

```
Lys Ala His Lys Val Asp Met Val Gln Tyr Thr
1               5                   10
```

(2) INFORMATION FOR SEQ ID NO:40:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO:40:

```
Val Gln Tyr Thr
1
```

(2) INFORMATION FOR SEQ ID NO:41:

(i) SEQUENCE CHARACTERISTICS:
            (A) LENGTH: 6 amino acids
            (B) TYPE: amino acid
            (C) STRANDEDNESS:
            (D) TOPOLOGY: linear (xi) SEQUENCE DESCRIPTION: SEQ ID NO:41:

Glu Lys Ala Val Ala Asp
1               5

(2) INFORMATION FOR SEQ ID NO:42:

(i) SEQUENCE CHARACTERISTICS:
            (A) LENGTH: 131 base pairs
            (B) TYPE: nucleic acid
            (C) STRANDEDNESS: single
            (D) TOPOLOGY: linear (ix) FEATURE:
            (A) NAME/KEY: CDS
            (B) LOCATION: 1..78

(xi) SEQUENCE DESCRIPTION: SEQ ID NO:42:

ATG AAA TTC TTA GTC AAC GTT GCC CTT TTT ATG GTC GTA TAC ATT TCT         48
Met Lys Phe Leu Val Asn Val Ala Leu Phe Met Val Val Tyr Ile Ser
                 40                  45                  50

TAC ATC TAT GCG GAT CCG AGC TCG AGT GCT CTAGATCTGC AGCTGGTACC            98
Tyr Ile Tyr Ala Asp Pro Ser Ser Ser Ala
             55                  60

ATGGAATTCG AAGCTTGGAG TCGACTCTGC TGA                                    131

(2) INFORMATION FOR SEQ ID NO:43:

(i) SEQUENCE CHARACTERISTICS:
            (A) LENGTH: 26 amino acids
            (B) TYPE: amino acid
            (D) TOPOLOGY: linear (ii) MOLECULE TYPE: protein (xi) SEQUENCE DESCRIPTION: SEQ ID NO:43:

Met Lys Phe Leu Val Asn Val Ala Leu Phe Met Val Val Tyr Ile Ser
1               5                   10                  15

Tyr Ile Tyr Ala Asp Pro Ser Ser Ser Ala
            20                  25

(2) INFORMATION FOR SEQ ID NO:44:

(i) SEQUENCE CHARACTERISTICS:
            (A) LENGTH: 4 amino acids
            (B) TYPE: amino acid
            (C) STRANDEDNESS:
            (D) TOPOLOGY: linear (xi) SEQUENCE DESCRIPTION: SEQ ID NO:44:

Lys Asp Glu Leu
1

(2) INFORMATION FOR SEQ ID NO:45:

(i) SEQUENCE CHARACTERISTICS:
            (A) LENGTH: 16 amino acids
            (B) TYPE: amino acid
            (C) STRANDEDNESS:
            (D) TOPOLOGY: linear (xi) SEQUENCE DESCRIPTION: SEQ ID NO:45:

```
Ala Ile Gln Asp Pro Arg Leu Phe Ala Glu Glu Lys Ala Val Ala Asp
1               5                   10                  15
```

(2) INFORMATION FOR SEQ ID NO:46:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:46:

```
GATCAGGAAG ATGAACGTAT TGTTCTGGTT GACAACAAGT GCAAGTGTGC TCGTATTACT      60
T                                                                     61
```

(2) INFORMATION FOR SEQ ID NO:47:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:47:

```
CTAGAAGTAA TACGAGCACA CTTGCACTTG TTGTCAACCA GAACAATACG TTCATCTTCC      60
T                                                                     61
```

(2) INFORMATION FOR SEQ ID NO:48:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:48:

```
GATCAGAAGT GCAAGTGTGC TCGTATTACT T                                    31
```

(2) INFORMATION FOR SEQ ID NO:49:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:49:

```
CTAGAAGTAA TACGAGCACA CTTGCACTTC T                                    31
```

(2) INFORMATION FOR SEQ ID NO:50:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:50:

```
GATCAGGAAG ATGAACGTAT TGTTCTGGTT GACAACAAGT GCAAGTCCGC TCGTATTACT      60
T                                                                     61
```

(2) INFORMATION FOR SEQ ID NO:51:

(i) SEQUENCE CHARACTERISTICS:
        (A) LENGTH: 61 base pairs

```
        (B) TYPE: nucleic acid
        (C) STRANDEDNESS: single
        (D) TOPOLOGY: linear (xi) SEQUENCE DESCRIPTION: SEQ ID NO:51:

CTAGAAGTAA TACGAGCGGA CTTGCACTTG TTGTCAACCA GAACAATACG TTCATCTTCC    60

T                                                                   61

(2) INFORMATION FOR SEQ ID NO:52:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:52:

GATCAGGAAG ATGAACGTAT TGTTCTGGTT GACAACAAGT GCAAGGTTGC TCGTATTACT    60

T                                                                   61

(2) INFORMATION FOR SEQ ID NO:53:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:53:

CTAGAAGTAA TACGAGCAAC CTTGCACTTG TTGTCAACCA GAACAATACG TTCATCTTCC    60

T                                                                   61

(2) INFORMATION FOR SEQ ID NO:54:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:54:

CTAGAATCAT CCGTAGCTCA GAGGACCCAA ATGAAGATAT AGTCGAA                  47

(2) INFORMATION FOR SEQ ID NO:55:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (xi) SEQUENCE DESCRIPTION: SEQ ID NO:55:

GATACGGATG TTACGTTCGA CTATATCTTC ATTTGGGTCC TCTGAGCTAC GGATGATT      58

(2) INFORMATION FOR SEQ ID NO:56:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:56:

CGTAACATCC GTATCATCGT CCCACTGAAT AACCGGGAGA ATATCTCAG                49
```

(2) INFORMATION FOR SEQ ID NO:57:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:57:

```
CGTAACATCC GTATCATCGT CCCACTGAAT AACCGGGAGC ACATCTCAG          49
```

(2) INFORMATION FOR SEQ ID NO:58:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:58:

```
ACGGACTTGT AGGATCTGAG ATATTCTCCC GGTTATTCAG TGGGACGAT          49
```

(2) INFORMATION FOR SEQ ID NO:59:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:59:

```
ACGGACTTGT AGGATCTGAG ATGTGCTCCC GGTTATTCAG TGGGACGAT          49
```

(2) INFORMATION FOR SEQ ID NO:60:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:60:

```
ATCCTACAAG TCCGTTGCGC ACACGCTTCG TATACCACCT GTCA               44
```

(2) INFORMATION FOR SEQ ID NO:61:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:61:

```
GATCTGACAG GTGGTATACG AAGCGTGTGC GCA                           33
```

(2) INFORMATION FOR SEQ ID NO:62:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (xi) SEQUENCE DESCRIPTION: SEQ ID NO:62:

```
GATCTGTGTA AGAAGTGTGA TCCAACAGAG GTAGAGCTGG ACAATCAGAT AGTCACTGCA    60
```

```
(2) INFORMATION FOR SEQ ID NO:63:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:63:

GATCTGTGTA AGAAGGATGA GGACAGCGCT ACAGAAACCT GCTG            44

(2) INFORMATION FOR SEQ ID NO:64:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:64:

AATTCAGCAG GTTTCTGTAG CGCTGTCCTC ATCCTTCTTA CACA            44

(2) INFORMATION FOR SEQ ID NO:65:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:65:

GATCTGTGTA AGAAGGATGA GGACAGCGCT ACAGAAACCT GCTACGAGAA GGATGAGCTG   60

TG                                                         62

(2) INFORMATION FOR SEQ ID NO:66:

(i) SEQUENCE CHARACTERISTICS:
        (A) LENGTH: 62 base pairs
        (B) TYPE: nucleic acid
        (C) STRANDEDNESS: single
        (D) TOPOLOGY: linear (xi) SEQUENCE DESCRIPTION: SEQ ID NO:66:

AATTCACAGC TCATCCTTCG CGTCGCAGGT TTCTGTAGCG CTGTCCTCAT CCTTCTTACA   60

CA                                                         62

(2) INFORMATION FOR SEQ ID NO:67:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO:67:

GATCTGTGTA AGAAGTCTGA TATCGATGAA GATTCCGCTA CAGAAACCTG CAGCACATG    59

(2) INFORMATION FOR SEQ ID NO:68:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO:68:
```

```
AATTCATGTG CTGCAGGTTT CTGTAGCGGA ATCTTCATCG ATATCAGACT TCTTACACA        59

(2) INFORMATION FOR SEQ ID NO:69:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:69:

GATCTGTCTA AGAAGTCTGA TATCGATGAA GATTACAGAT TCTTCAGACT ATAGCTACTT        60

CTAA                                                                    64

(2) INFORMATION FOR SEQ ID NO:70:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:70:

AATCTTCATC GATATCAGAC TTCTTAGACA                                        30

(2) INFORMATION FOR SEQ ID NO:71:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (xi) SEQUENCE DESCRIPTION: SEQ ID NO:71:

GATCTGGTTA AGAAGTCTGA TATCGATGAA GATTACCAAT TCTTCAGACT ATAGCTACTT        60

CTAA                                                                    64

(2) INFORMATION FOR SEQ ID NO:72:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:72:

AATCTTCATC GATATCAGAC TTCTTAACCA                                        30

(2) INFORMATION FOR SEQ ID NO:73:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:73:

ATTGTCCAGC TCTACCTCTG TTGGATCACA CTTCTTACAC A                           41

(2) INFORMATION FOR SEQ ID NO:74:

(i) SEQUENCE CHARACTERISTICS:
        (A) LENGTH: 46 base pairs
        (B) TYPE: nucleic acid
        (C) STRANDEDNESS: single
        (D) TOPOLOGY: linear
```

(xi) SEQUENCE DESCRIPTION: SEQ ID NO:74:

ACTCAAAGCA ACATTTGCGA TGAGGACAGC GCTACAGAAA CCTGCA                46

(2) INFORMATION FOR SEQ ID NO:75:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (xi) SEQUENCE DESCRIPTION: SEQ ID NO:75:

GGTTTCTGTA GCGCTCTGCT CATCGCAAAT GTTGCTTTGA GTCGCAGTGA CTATCTG        57

(2) INFORMATION FOR SEQ ID NO:76:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO:76:

GCACCTACGA TAGGAACAAA TGCTACACGG CCGTGGTTCC GCTCGTGTAT GGTGGAGAG       59

(2) INFORMATION FOR SEQ ID NO:77:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (xi) SEQUENCE DESCRIPTION: SEQ ID NO:77:

GAGCGGAACC ACGGCCGTGT AGCATTTGTT CCTATCGTAG GTGCTGCA                  48

(2) INFORMATION FOR SEQ ID NO:78:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:78:

ACAAAAATGG TGGAAACTGC CCTTACGCCC GATGCATGCT ATCCGGACTG                50

(2) INFORMATION FOR SEQ ID NO:79:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (xi) SEQUENCE DESCRIPTION: SEQ ID NO:79:

AATTCAGTCC GGATAGCATG CATCGGGCGT AAGGGCAGTT TCCACCATTT TTGTCTCTCC      60

ACCATACAC                                                            69

(2) INFORMATION FOR SEQ ID NO:80:

(i) SEQUENCE CHARACTERISTICS:
        (A) LENGTH: 62 base pairs
        (B) TYPE: nucleic acid
        (C) STRANDEDNESS: single (D) TOPOLOGY: linear (xi) SEQUENCE DESCRIPTION: SEQ ID NO:80:

ACAAAAATGG TGGAAACTGC CCTTACGCCC GATGCATGCT ATCCGGACAA GGATGAATTG    60

TG                                                                 62

(2) INFORMATION FOR SEQ ID NO:81:

(i) SEQUENCE CHARACTERISTICS:
          (A) LENGTH: 81 base pairs
          (B) TYPE: nucleic acid
          (C) STRANDEDNESS: single
          (D) TOPOLOGY: linear (xi) SEQUENCE DESCRIPTION: SEQ ID NO:81:

AATTCACAAT TCATCCTTGT CCGGATAGCA TGCATCGGGC GTAAGGGCAG TTTCCACCAT    60

TTTTGTCTCT CCACCATACA C                                            81

(2) INFORMATION FOR SEQ ID NO:82:

(i) SEQUENCE CHARACTERISTICS:
          (A) LENGTH: 88 base pairs
          (B) TYPE: nucleic acid
          (C) STRANDEDNESS: single
          (D) TOPOLOGY: linear (xi) SEQUENCE DESCRIPTION: SEQ ID NO:82:

GATCAGGTCG CTGCCATCCA AGACCCGAGG CTGTTCGCCG AAGAGAAGGC CGTCGCTGAC    60

TCCAAGTGCA AGTGTGCTCG TATTACTT                                     88

(2) INFORMATION FOR SEQ ID NO:83:

(i) SEQUENCE CHARACTERISTICS:
          (A) LENGTH: 88 base pairs
          (B) TYPE: nucleic acid
          (C) STRANDEDNESS: single
          (D) TOPOLOGY: linear (xi) SEQUENCE DESCRIPTION: SEQ ID NO:83:

CTAGAAGTAA TACGAGCACA CTTGCACTTG GAGTCAGCGA CGGCCTTCTC TTCGGCGAAC    60

AGCCTCGGGT CTTGGATGGC AGCGACCT                                     88

(2) INFORMATION FOR SEQ ID NO:84:

(i) SEQUENCE CHARACTERISTICS:
          (A) LENGTH: 10 amino acids
          (B) TYPE: amino acid
          (C) STRANDEDNESS: single
          (D) TOPOLOGY: linear (xi) SEQUENCE DESCRIPTION: SEQ ID NO:84:

Cys Ala Ala Pro Lys Lys Lys Arg Lys Val
1               5                   10

(2) INFORMATION FOR SEQ ID NO:85:

(i) SEQUENCE CHARACTERISTICS:
          (A) LENGTH: 22 amino acids
          (B) TYPE: amino acid
          (C) STRANDEDNESS:
          (D) TOPOLOGY: linear (xi) SEQUENCE DESCRIPTION: SEQ ID NO:85:

Cys Ala Ala Lys Arg Pro Pro Ala Ala Ile Lys Lys Ala Ala Ala Gly

```
1               5                   10                  15
```

Gln Ala Lys Lys Lys Lys
            20

(2) INFORMATION FOR SEQ ID NO:86:

(i) SEQUENCE CHARACTERISTICS:
        (A) LENGTH: 4 amino acids
        (B) TYPE: amino acid
        (C) STRANDEDNESS:
        (D) TOPOLOGY: linear (xi) SEQUENCE DESCRIPTION: SEQ ID NO:86:

His Asp Glu Leu
1

(2) INFORMATION FOR SEQ ID NO:87:

(i) SEQUENCE CHARACTERISTICS:
        (A) LENGTH: 77 base pairs
        (B) TYPE: nucleic acid
        (C) STRANDEDNESS: single
        (D) TOPOLOGY: linear (xi) SEQUENCE DESCRIPTION: SEQ ID NO:87:

GCGATGACGA CGATAAGGCC CAAACGGAGA CCTGTACTGT TGCGCCTCGT GAACGGCAAA           60

ACTGCGGATT CCCGGAA                                                         77

(2) INFORMATION FOR SEQ ID NO:88:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (xi) SEQUENCE DESCRIPTION: SEQ ID NO:88:

GTTTTGCCGT TCACGAGGCG CAACAGTACA GGTCTCCGTT TGGGCCTTAT CGTCGTCATC           60

GCTTCA                                                                     66

(2) INFORMATION FOR SEQ ID NO:89:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:89:

GTAACACCCT CTCAGTGCGC TAATAAAGGC TGCTGTTTTG ATGACACGGT ACGGGGCGTT           60

CCGTGGTGCT TC                                                              72

(2) INFORMATION FOR SEQ ID NO:90:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (xi) SEQUENCE DESCRIPTION: SEQ ID NO:90:

GCCCCGTACC GTGTCATCAA AACAGCAGCC TTTATTAGCG CACTGAGAGG GTGTTACTTC           60

CGGGAATCCG CA                                                              72

(2) INFORMATION FOR SEQ ID NO:91:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (xi) SEQUENCE DESCRIPTION: SEQ ID NO:91:

TACCCCAATA CAATTGACGT TCCGCCTGAA GAAGAGTGCG AGCCGTAAG           49

(2) INFORMATION FOR SEQ ID NO:92:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (xi) SEQUENCE DESCRIPTION: SEQ ID NO:92:

AATTCTTACG GCTCGCACTC TTCTTCAGGC GGCAAGTCAA TTGTATTGGG GTAGAAGCAC    60

CACGGAAC                                                             68

(2) INFORMATION FOR SEQ ID NO:93:

(i) SEQUENCE CHARACTERISTICS:
        (A) LENGTH: 13 amino acids
        (B) TYPE: amino acid
        (C) STRANDEDNESS:
        (D) TOPOLOGY: linear (xi) SEQUENCE DESCRIPTION: SEQ ID NO:93:

Val Ala Val Gln Ser Ala Gly Thr Pro Ala Ser Gly Ser
1               5                   10